(12) United States Patent
Felber et al.

(10) Patent No.: US 7,833,754 B2
(45) Date of Patent: Nov. 16, 2010

(54) IL-12 FOR EXPRESSION IN MAMMALIAN CELL

(75) Inventors: Barbara Felber, Rockville, MD (US); George N. Pavlakis, Rockville, MD (US); Margherita Rosati, Frederick, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 12/160,422

(22) PCT Filed: Jan. 12, 2007

(86) PCT No.: PCT/US2007/000825
§ 371 (c)(1), (2), (4) Date: Jul. 9, 2008

(87) PCT Pub. No.: WO2007/084364
PCT Pub. Date: Jul. 26, 2007

(65) Prior Publication Data
US 2009/0137005 A1      May 28, 2009

Related U.S. Application Data

(60) Provisional application No. 60/758,680, filed on Jan. 13, 2006.

(51) Int. Cl.
| C12N 15/63 | (2006.01) |
| C12N 15/64 | (2006.01) |
| C12N 15/66 | (2006.01) |
| C12N 15/67 | (2006.01) |
| C12N 5/02  | (2006.01) |
| C12N 5/10  | (2006.01) |
| C12P 21/02 | (2006.01) |

(52) U.S. Cl. ............... 435/69.52; 435/320.1; 435/325; 435/471; 536/23.5; 530/351

(58) Field of Classification Search ............. None
See application file for complete search history.

(56) References Cited

U.S. PATENT DOCUMENTS 5,922,685 A * 7/1999 Rakhmilevich et al. ....... 514/44
2003/0181405 A1  9/2003 Nordstrom et al.

FOREIGN PATENT DOCUMENTS

| WO | WO 98/17814    | 4/1998  |
| WO | WO 99/47678    | 9/1999  |
| WO | WO 2005/118874 | 12/2005 |

OTHER PUBLICATIONS

Crystal R, Science, 1995. vol. 270, pp. 404-410.*
Anderson W, Nature, 1998. vol. 392, pp. 25-30.*
Verma et al. Nature, 1997. vol. 389, p. 239-242, col. 3, paragraph 2.*
Gabor M. Rubanyi, Mol Aspects Med, 2001 vol. 22, pp. 113-142.*
Jayaray et al., "GeMS: an advanced software package for designing synthetic genes," 2005, Nucleic Acids Res.,; 33: 3011-3016.

* cited by examiner

*Primary Examiner*—Bridget E Bunner
*Assistant Examiner*—Fozia M Hamud
(74) *Attorney, Agent, or Firm*—Townsend and Townsend and Crew LLP

(57) ABSTRACT

The present invention provides for nucleic acids improved for the expression of interleukin-12 (IL-12) in mammalian cells. The invention further provides for methods of expressing IL-12 in mammalian cells by transfecting the cell with a nucleic acid sequence encoding an improved IL-12 sequence.

18 Claims, 21 Drawing Sheets

Figure 5

```
huIL12p35     atg tgt cca gcg cgc agc ctc ctt gtg ct  acc ctg ctc gtc ctg gac cac ctc agt
huIL12p35opt  atg tgc ccg gcg cgc tcc ctg ctc gtc gtg gcg acg ctg ctg gtg ctg gac cac ctg agc
              *   *   * * *   *** *      *   *   *** *   *** *   * * huIL12p35     ttg gcc aga aac ctc ccc gtg gcc act cca gac ctg gga atg ttc cca ctt cac cac
huIL12p35opt  ctg gcg cgg aac ctg ccg gtg gcg acg ccg gac ggg atg ttc ccg ctg cac cac
                  *   *   *   *       * *       * * * *** huIL12p35     tcc caa aac ctg ctg agg gcc gtc agc aac atg ctc cag aag aag ctg gac aga caa act cta gaa
huIL12p35opt  agc cag aac ctg ctg cgg gcg gtg tcg aac atg ctg cag aag aag gcg cgg cag acg ctg gag
              *     * * * *        *  * *   * * * *   *       ** huIL12p35     ttt tac cct tgc act tct gaa gag att gat cat gaa gat atc aca aaa gat aaa acc agc
huIL12p35opt  ttc tac ccg tgc acg agc gag gag atc gac cac gag gac atc acc aag gac aag acc agc
                *   * **  *   * * **  *     * *   *   **  *     * *** huIL12p35     aca gtt gag gcc tgt tta cca tta acc aag aat ttc ctg aga agt aag aaa gat gat ttt tcc aga
huIL12p35opt  acg gtg gag gcg tgc ctg ccg ctg acc aag aat ttc ctg cgg acg agc aag aag gcg gcc cgg
                  *   **  *   **   *  * * * * *** *   **  *   *   *   *   ** huIL12p35     gag acc tct ttc ata act aat ggg agt tgc ctg ctg aag gcc aga acc tct ttt ttt atg atg
huIL12p35opt  gag acg tcg ttc atc acg aac ggg agc tgc ctg cgg tgg gcg aag ctg ctg ttc ttc atg atg
              *   *   *       *   * * *   *               * * huIL12p35     gcc ctg tgc ctt agt agt att tat gaa gac ttg aag atg tac cag gtg gag ttc aag acc
huIL12p35opt  gcg ctg tgc ctg tcg tcg atc tac gag gac ctg aag atg tac cag gtg gag ttc aag acg
                * *   *   *       * * *   * * * * * * * * ** huIL12p35     atg aat gca aag ctt ctg atg gat cct aag agg cag atc ttt cta gat caa aac atg ctg
huIL12p35opt  atg aac gcg aag ctg ctg atg gac ccg aag cgg cag atc ctc gac cag aac atg ctg
              *     *   * *** *     * *   * * *   *** *   * * * * huIL12p35     gca gtt att gat gag ctg atg cag gcc ctg aat ttc aac agt gag act gtg cca caa aaa
huIL12p35opt  gcg gtg atc gag gag ctg atg cag gcg ctg aac ttc aac agc gag acg gtg ccg cag aag
                  *   *   * * * *   *   * *** *   *   * huIL12p35     tcc tcc ctt gaa gaa ccg gat ttt tat aaa act acg aag atc aaa agc tgc ata ctt ctt cat
huIL12p35opt  tcg tcg ctc gag gag ccg gac ttc tac aaa acg acg aag atc aag tcg tgc atc ctg cat
              *   *   *   * * *** *       *     * *    *  *   *** huIL12p35     gct ttc aga att cgg gca gtg aca att gat aga atg atg tat tgc taa tcc taa tag
huIL12p35opt  gct ttc cgg atc cgg gcg gtg acg atc gac cgg atg atg tcg tgc ctg taa tcg taa
              *** *** *   *   *** **  *** **  *   **  *   *** *** *   *** **   ** ***
```

```
              1                                              10                                              20
huIL12p40     atg tgt cac cag cag ttg gtc atc tct tgg ttt tcc ctg gtt ttt ctg gca tct ccc ctc
huIL12p40opt  atg tgc cac cag cag ctg gtc atc agc tgg ttc agc ctc gtt ttc ctc gcc tcg ccg ctg
              *** **  *** *** *** **  *** *** **  *** **  **  *** *** **  *** **  **  **  **

21                                             30                                              40
huIL12p40     gtg gcc ata tgg gaa ctg aaa aag gat gtt cct gtc gta gaa ttg gat tgg tat ccg gat
huIL12p40opt  gtc gcc ata tgg gag ctc aag aag gac gta gtg gtg gag ctg gac tgg tac ccc gac
              **  *** *** *** **  **  **  *** **  **  **  **  **  **  *** **  *** **  ***

41                                             50                                              60
huIL12p40     gcc cct gga gaa atg gtg gtc ctc acc tgt gac acc cct gaa gaa gat ggt atc acc tgg
huIL12p40opt  gcg ccg gga gag atg gtc gtc ctg acg tgc gac acg ccg gag gag gac ggc atc acg tgg
              **  **  *** **  *** **  *** **  **  **  *** **  **  **  **  *** **  *** **  ***

61                                             70                                              80
huIL12p40     acc ttg gac cag agc agt gag gtc tta ggc tct cac aaa acc ctg aaa gtt cta agc aaa
huIL12p40opt  acg ctg gac cag agc tcc gag gtc ctc ggc tcc cac aag acg ctg acg gtc ctg agc aag
              **  **  *** *** *** **  *** *** *   *** **  *** **  **  *** **  **  **  *** **

81                                             90                                              100
huIL12p40     gag ttt gga gat gct ggc cag tac acc tgt cac aaa gga gga gag gtt cta agc cat tcg
huIL12p40opt  gag ttc ggc gac gcg ggc cag tac acg tgc cac aag ggc ggc gag gtc ctg agc cac tcc
              *** **  **  **  **  *** *** *** **  **  *** **  **  **  *** **  *** **  **

101                                            110                                             120
huIL12p40     ctc ctg ctg ctt cac aaa aag gaa gga gat att tgg tcc act gat att tta aag gac cag
huIL12p40opt  ctc ctc ctg cta cac aag aag gag ggg atc gac atc tgg agc acg gac atc ctc aag gac cag
              *** **  *** *   *** **  *** **  *   **  *   **  **  **  *** **  **  *   *** *** ***

121                                            130                                             140
huIL12p40     aaa gaa ccc aaa aat aag acc ttt cta aga tgc gag gcc aag aat tat tct gga cgt ttc
huIL12p40opt  aag gag ccg aag aac aag acc ttc ctg agg tgc gag gcg aag aat tac tcg ggc cgg ttc
              **  **  **  **  **  *** *** **  **  *   *** *** **  *** *** **  **  **  **  ***

141                                            150                                             160
huIL12p40     acc tgc tgg tgg ctg acg aca atc agt act gat ttg aca ttc agt gtc aaa agc aga
huIL12p40opt  acg tgc tgg tgg ctc acc acg atc agc agc gac ctg acg ttc tcg gtc aag agc cgg
              **  *** *** *** *   **  **  *** **  *   **  *   **  *** *   *** **  *** *
```

Figure 7B

```
            161                                                                        180
huIL12p40   ggc tct tct gac ccc caa ggg gtg acg tgc gga gct gct aca ctc tct gca gag aga gtc
huIL12p40opt ggc tcg gac ccc cag ggg gtg acc tgc ggc gcg gcg acg ctg tcg gcg gag cgg gtg
             ***  *   *  ***  *  ** *** *** ***  **  *  *** *** *** *** *** *** *   **   *
            181                                                                        200
huIL12p40   aga ggg gac aac aag gag tat gag tca gtg gag tgc cag gag gac agt gcc tgc cca
huIL12p40opt cgg ggc gac aac aag gag tac gag tcg gtc gag tgc cag gag gac tcg gcg tgc ccg
              *   *  *** *** *** ***  *  ***  *   *  *** *** *** *** *** **   **  **   *
            201                                                                        220
huIL12p40   gct gct gag gag agt ctg ccc att gag gtc atg gtg gat gtt gcc cac aag ctc tat
huIL12p40opt gcg gcg gag gag gag tcg ccg atc gag gtc atg gtc gac gcg gcg cac aag ctg tac
             **   **  *** ***  **  *   **   *  *** *** ***  **   *   *  *** *** **   *
            221                                                                        240
huIL12p40   gaa aac tac acc agc ttc atc agg gac atc atc aaa cct gac ccc cca aag aac
huIL12p40opt gag aac tac acg tcg ttc atc cgg gac atc atc aag ccg gac ccg ccg aag aac
              *  *** *** **   *  *** ***  **  *** *** ***  *   *  *** **   **  *** ***
            241                                                                        260
huIL12p40   ttg cag ctg aag aat tct cgg ttc tcc ctg aca ttc gtt cag agc gtg gag tac cct gac
huIL12p40opt ctg cag ctg aag aac tcg cgg ttc tcc ctg acg ttc gtc caa tgc gtc tgg gag tac ccg gac
              *  *** ***  **  **   *  *** *** *** ***  **  *** **   **   *  **   *  *** ***  **  ***
            261                                                                        280
huIL12p40   acc tgg agt act cca cat tcc tac aga ctg aca acg aag aag ttc gtt cag agc gtc cag ggc gtc atc tgc
huIL12p40opt acg tgg tcg acg ccg cac tcg tac cgg ctg acc aag aag ttc acg gtc caa tgc gtc tgg ggc gtg atc tgc
              *  *** *   **   **   *   *  *** **  *** **   *  *** ***   *  **   *   *  **   *  ***  **  *** ***
            281                                                                        300
huIL12p40   agc aag aag aga gat aga ttc acg gtc ttc acc tca gcc acg gtc atc tgc
huIL12p40opt tcg aag cgg aag agc cgg ttc acg gtc tcg acc agc gcg acg gtg atc tgc
              *  ***  *  ***  **   *  *** *** ***  **  *** ***  **  *** **  *** ***
            301                                                                        320
huIL12p40   cgc aaa aat gcc att agc gtg cgg gcc tac cgc tac tat agc tca tct tgg agc
huIL12p40opt cgg aag aac gcg agc tcg atc tcg gcg gtg cgg tac cgg tac tac tcg tcg tgg tcg
              *   *  **   *  *** **   *   *  ***  *  *** *** **  *** ***  **   **  ***  *
            321                                328
huIL12p40wt  gaa tgg gca tct gtg ccc tgc agt tag taa
huIL12p40opt gag tgg gcg tcg gtg ccg tgc agc tag
              *  *** **   *  *** **  *** **  ***
```

```
              10        20        30        40        50        60        70
rhIL12p35     ATGTGTCCAGCGCGCAGCCTCCTCCTTGTGGCCACCCTAGTCCTCCTGGACTACCTCAGTTTGGCCAGAAACCTCTCC
              :::::  ::  ::::::    :::  ::  ::  :::::  ::  ::  :::::  ::  ::::::::  ::   ::::    :  :::::  ::
rhIL12p35opt  ATGTGCCCGGCGCGCTCCCTGCTGCTCGTGGCGACGCTGGTCCTGCTCGACTACCTGAGCCTGGCGCGGAACCTGTCG 80        90       100       110       120       130       140       150      1
rhIL12p35     GGCCACCCCAGGCCCAGAAATGTTCCCGTGCCTTCACCACTCCCAAAACCTGCTGAAGGCCGCCAGCAACACGCTTCA
              :::  :::::  ::  ::  ::  ::::::::::::::::.::::::   :::  :::::::::::::::  ::   :::::::::.::
rhIL12p35opt  GGCGACCCCGGGACCGGAGATGTTCCCGTGCCTGCACCACAGCCAGAACCTGCTGAAGGCGGCGTCGAACACGCTGCA 160       170       180       190       200       210       220       230      2
rhIL12p35     AGGCCAGACAAATTCTAGAATTTTACCCTTGCACTTCTGAAGAGATTGATCATGAAGATATCACAAAAGATAAAACCA
              ::::   ::   ::  ::  ::  ::  :::::.:::::.         ::  :::::  ::  ::  ::  ::  :::::  ::  ::  ::  ::::
rhIL12p35opt  AGGCGCGGCAGATCCTGGAGTTCTACCCGTGCACGAGCGAGGAGATCGACCACGAGGACATCACGAAGGACAAGACCA 240       250       260       270       280       290       300       310      3
rhIL12p35     ACAGTAGAGGCCTGTTTACCATTGGAATTAATCAAGAATGAGAGTTGCCTAAATTCCAGAGAGACTTCTTTCATAACT.
              ::  ::  :::::  ::    :  ::  ::::   :   :::::::::  :::     .:::::  ::  ::  ::  :::::       :::::  ::
rhIL12p35opt  ACGGTGGAGGCGTGCCTGCCGCTGGAGCTGATCAAGAACGAGTCGTGCCTGAACTCGAGGGAGACCAGCTTCATCACC 320       330       340       350       360       370       380       390      4
rhIL12p35     TGGGAGTTGCCTGGCCTCCAGAAAGACCTCTTTTATGATGGCCCTGTGCCTTAGGAGTATTTATGAAGACTTGAAGAT
              ::  ::  :::::::::     :::::::::::::  ::  ::::::::::::  ::::::::::.:::::  ::  ::  ::  :::  :::::::
rhIL12p35opt  CGGCAGCTGCCTGGCCAGCAGAAAGACCTCCTTCATGATGGCCCTGTGCCTGAGGAGCATCTACGAGGACCTGAAGAT 410       420       430       440       450       460       470              4
rhIL12p35     ACCAAGTGGAGTTCAAGACCATGAATGCAAAGCTTCTGAGGGATCCTAAGAGGCAGATCTTTCTAGATCAAAACATAC
              ::::   ::::::::::::::::::::::::::  ::  :::::.::::::::::  ::  :::::::::::::::  ::  ::  ::  :::::    :
rhIL12p35opt  ACCAGGTGGAGTTCAAGACCATGAACGCCAAGCTGCTGAGGGACCCCAAGAGGCAGATCTTCCTGGACCAGAACATCC 490       500       510       520       530       540       550              5
rhIL12p35     GGAGTTATTGATGAGCTGATGCAGGCCCTGAATTTCAACAGTGAGACTGTGCCACAAAAATCCTCCCTTGAAGAACCG
              ::  ::..::  ::  :::::::::::::::::::  ::::::::::  ::::::  :::::  :::::      :  :::.::  ::  ::
rhIL12p35opt  GGCGTGATCGACGAGCTGATGCAGGCCCTGAACTTCAACAGCGAGACCGTGCCTCAGAAGAGCAGCCTGGAGGAGCCC 570       580       590       600       610       620       630              6
rhIL12p35     TTTTTATAAAACTAAAATCAAGCTCTGCATACTTCTTCATGCTTTCAGAATTCGGGCAGTGACTATTGATAGAGTGAT
              ::  ::  ::  ::  ::  :::::::::  :::::  ::.::.-::  ::  :::  :  ::  ::::  :::::  ::  ::  :::::::::
rhIL12p35opt  CTTCTACAAGACCAAGATCAAGCTGTGCATCCTGCTGCACGCCTTCCGGATCAGGGCCGTGACCATCGACAGAGTGAT 650       660
rhIL12p35     GCTATCTGAATGCTTCCTAATAG
              ::::  :::::  ::    ::  :::
rhIL12p35opt  GCTACCTGAACGCCAGCTGATAA
```

*Figure 11*

```
              10         20         30         40         50         60         70         80
p40wt    ATGTGTCACCAGCAGCTGGTCATCTCTTGGTTTTCCCTGGTTTTTCTGGCATCTCCCCTCATGGCCATATGGGAACTGAA
         :::::  :::::::::::::  :::    :::::  ::::::: ::  :::::    :::::  ::::::::  :::::  :::::
p40opt   ATGTGCCACCAGCAGCTGGTGATCAGCTGGTTCAGCCTGGTGTTCCTGGCCAGCCCCCTGATGGCCATCTGGGAGCTGAA
              90        100        110        120        130        140        150        160
p40wt    GAAAGACGTTTATGTTGTAGAATTGGACTGGTACCCGGATGCCCCTGGAGAAATGGTGGTCCTCACCTGTGACACCCTG
         :::  :::::  ::  ::.:: ::  ::::::::::::  ::  ::  :::::  ::  ::::::::::  ::  :::::  ::::::::::  :
p40opt   GAAGGACGTATACGTGGTGGAGCTGGACTGGTATCCCGACGCGCCTGGCGAGATGGTGGTGCTGACCTGCGACACCCCG
              170        180        190        200        210        220        230        240
p40wt    AAGAAGATGGTATCACCTGGACCTTGGACCAGAGTGGTGAGGTCTTAGGCTCTGGCAAAACCCTGACCATCCAAGTCAAA
         :  ::  ::  ::  :::::::::::::  ::::::::::::  ::  ::  :  :::    :::::  ::::::::::  :::::  :::::
p40opt   AGGAGGACGGCATCACCTGGACCCTGGACCAGAGCGGCGAAGTGCTGGGCAGCGGCAAGACCCTGACGATCCAGGTCAAG
              250        260        270        280        290        300        310        320
p40wt    GAGTTTGGAGATGCTGGCCAGTACACCTGTCACAAAGGAGGCGAGGCTCTAAGCCATTCACTCCTGCTGCTTCACAAAAA
         :::::  ::  ::  ::  :::::::::::::::::::  :::::  ::  ::::::::::  ::  :::::      ::  :::::::::.:::::  ::
p40opt   GAGTTCGGCGACGCCGGCCAGTACACCTGCCACAAGGGCGGCGAGGCCCTGAGCCACAGCCTGCTGCTGCTGCACAAGAA
              330        340        350        360        370        380        390        400
p40wt    GGAAGATGGAATTTGGTCCACTGATGTTTTAAAGGACCAGAAAGAACCCAAAAATAAGACCTTTCTAAGATGTGAGGCCA
         :::  ::  ::  ::  :::    :::  ::  ::.  :  :::::::::::::  ::  :::::  ::  ::::::::::  ::    ::  :::::::.
p40opt   GGAGGACGGGATCTGGAGCACCGACGTGCTGAAGGACCAGAAGGAGCCCAAGAACAAGACCTTCCTGCGCTGCGAGGCCA
              410        420        430        440        450        460        470        480
p40wt    AAAATTATTCTGGACGTTTCACCTGCTGGTGGCTGACGACAATCAGTACTGATCTGACATTCAGTGTCAAAAGCAGCAGA
         :  :::::     ::  ::.:::::::::  :::::::::::  ::  :::::  ::  ::  :::::  :::::  ::  ::  :::::::::::
p40opt   AGAATTACAGCGGCCGGTTCACCTGTTGGTGGCTGACCACCATCAGCACCGACCTGACCTTCAGCGTGAAGAGCAGCAGA
              490        500        510        520        530        540        550        560
p40wt    GGC-TCTTCTAACCCCCAAGGGGTGACATGTGGAGCCGTTACACTCTCTGCAGAGAGGGTCAGAGGGGACAATAAGGAGT
         :::  .:  .:  :::::::::  ::  :::::  :::::  ::::::.::  ::       ::  :::::  ::  :::::  :::::  :::::::
p40opt   GGCAGCAGC-AACCCCCAGGGCGTGACCTGTGGCGCCGTGACCCTGAGCGCCGAGAGAGTGAGAGGCGACAACAAGGAGT
              570        580        590        600        610        620        630        640
p40wt    ATGAGTACTCAGTGGAGTGCCAGGAGGACAGTGCCTGCCCAGCCGCTGAGGAGAGGCTGCCCATTGAGGTCATGGTGGAT
         :  :::::::  ::::::::::::::  ::::::::::::::::  :::::  :::::::::  ::::::::::  ::  ::  :::::::::::
p40opt   ACGAGTACAGCGTGGAGTGCCAGGAGGACAGCGCCTGCCCTGCCGCCGAGGAGAGACTGCCCATCGAAGTGATGGTGGAC
              650        660        670        680        690        700        710        720
p40wt    GCCATTCACAAGCTCAAGTATGAAAACTACACCAGCAGCTTCTTCATCAGGGACATCATCAAACCCGACCCACCCAAGAA
         :::::  ::::::::  :::::  ::  ::::::::::::::       ::::::::  :::::::::::::  ::::::::::  :::::::::::
p40opt   GCCATCCACAAGCTGAAGTACGAGAACTACACCAGCTCCTTCTTCATCCGGGACATCATCAAGCCCGACCCCCCCAAGAA
              730        740        750        760        770        780        790        800
p40wt    CTTGCAGCTGAAGCCATTAAAGAATTCTCGGCAGGTGGAGGTCAGCTGGGAGTACCCTGACACCTGGAGTACTCCACATT
         :  :::::::::::::::  :  :::::    :::::::::::::  ::  :::::::::::::::  ::::::::::::::::  ::  ::
p40opt   CCTGCAGCTGAAGCCCCTGAAGAACAGCAGGCAGGTGGAAGTGAGCTGGGAGTACCCCGACACCTGGAGCACCCCTCACA
              810        820        830        840        850        860        870        880
p40wt    CCTACTTCTCCCTGACATTCTGCATCCAGGTCCAGGGCAAGAGCAAGAGAGAAAAGAAAGATAGAATCTTCACAGACAAG
         ::::::    :::::  :::::::::::  ::  :::::::::::::::  :  ::  :::::  ::    :  ::::::::::  ::  :::
p40opt   GCTACTTCAGCCTGACCTTCTGCATCCAAGTGCAGGGCAAGAGCAAGCGGGAGAAGAAGGACCGGATCTTCACCGATAAG
              890        900        910        920        930        940        950        960
p40wt    ACCTCAGCCACGGTCATCTGCCGCAAAAATGCCAGCTTTAGCGTGCAGGCCCAGGACCGCTACTATAGC-TCATCTTGGA
         :::       :::::  ::  :::::::::  ::  ::  ::::::::  :::::::::::::::::::::  :  :::::  :::    .::.:  ::::
p40opt   ACCAGCGCCACCGTGATCTGCCGGAAGAACGCCAGCTTCAGCGTGCAGGCCCAGGACAGATACTACAGCAGC-TGGA
              970        980
p40wt    GCGAATGGGCATCTGTGCCCTGCAGTTAG
         ::::  :::::       :::::  :::::  :
p40opt   GCGAGTGGGCCAGCGTGCCTTGCAGCTGATGA
```

*Figure 13*

```
              10         20         30         40         50         60         70         80
p35wt   MCPARSLLLVATIVLIDHLSLARNLPVATPDPGMFPCLHHSQNLLRAVSNMLQKARQTLEFYPCTSEEIDHEDITKDKTS
        ::::::::::::::::::::::::::::::::::::::::::::::::::::::::::::::::::::::::::::::::
p35opt  MCPARSLLLVATIVLIDHLSLARNLPVATPDPGMFPCLHHSQNLLRAVSNMLQKARQTLEFYPCTSEEIDHEDITKDKTS
              10         20         30         40         50         60         70         80

90        100        110        120        130        140        150        160
p35wt   TVEACLPLELTKNESCLNSRETSFITNGSCLASRKTSFMMALCLSSIYEDLKMYQVEFKTMNAKLLMDPKRQIFLDQNML
        ::::::::::::::::::::::::::::::::::::::::::::::::::::::::::::::::::::::::::::::::
p35opt  TVEACLPLELTKNESCLNSRETSFITNGSCLASRKTSFMMALCLSSIYEDLKMYQVEFKTMNAKLLMDPKRQIFLDQNML
              90        100        110        120        130        140        150        160

170        180        190        200        210        220
p35wt   AVIDELMQALNFNSETVPQKSSLEEPDFYKTKIKLCILLHAFRIRAVTIDRVMSYLNAS
        :::::::::::::::::::::::::::::::::::::::::::::::::::::::::::
p35opt  AVIDELMQALNFNSETVPQKSSLEEPDFYKTKIKLCILLHAFRIRAVTIDRVMSYLNAS
             170        180        190        200        210        220
```

Figure 14

```
              10         20         30         40         50         60         70         80
p40wt    MCHQQLVISWFSLVFTLASPLVAIWELKKDVYVVELDWYPDAPGEMVLTCDTPEEDGITWTLDQSSEVLGSGKTLTIQVK
         ::::::::::::::::::::::::::::::::::::::::::::::::::::::::::::::::::::::::::::::::
p40opt   MCHQQLVISWFSLVFTLASPLVAIWELKKDVYVVELDWYPDAPGEMVLTCDTPEEDGITWTLDQSSEVLGSGKTLTIQVK
              10         20         30         40         50         60         70         80

90        100        110        120        130        140        150        160
p40wt    EFGDAGQYTCHKGGEVLSHSLLLLHKKEDGIWSTDILKDQKEPKNKTFLRCEAKNYSGRFTCWWLTTISTDLTFSVKSSR
         ::::::::::::::::::::::::::::::::::::::::::::::::::::::::::::::::::::::::::::::::
p40opt   EFGDAGQYTCHKGGEVLSHSLLLLHKKEDGIWSTDILKDQKEPKNKTFLRCEAKNYSGRFTCWWLTTISTDLTFSVKSSR
              90        100        110        120        130        140        150        160

170        180        190        200        210        220        230        240
p40wt    GSSDPQGVTCGAATLSAERVRGDNKEYEYSVECQEDSACPAAEESLPIEVMVDAVHKLKYENYTSSFFIRDIIKPDPPKN
         ::::::::::::::::::::::::::::::::::::::::::::::::::::::::::::::::::::::::::::::::
p40opt   GSSDPQGVTCGAATLSAERVRGDNKEYEYSVECQEDSACPAAEESLPIEVMVDAVHKLKYENYTSSFFIRDIIKPDPPKN
             170        180        190        200        210        220        230        240

250        260        270        280        290        300        310        320
p40wt    LQLKPLKNSRQVEVSWEYPDTWSTPHSYFSLTFCVQVQGKSKREKKDRVFTDKTSATVICRKNASISVRAQDRYYSSSWS
         ::::::::::::::::::::::::::::::::::::::::::::::::::::::::::::::::::::::::::::::::
p40opt   LQLKPLKNSRQVEVSWEYPDTWSTPHSYFSLTFCVQVQGKSKREKKDRVFTDKTSATVICRKNASISVRAQDRYYSSSWS
             250        260        270        280        290        300        310        320 p40wt    EWASVPCS
         ::::::::
p40opt   EWASVPCS
```

Figure 15

Comparison of rhesus IL12p35 proteins expressed from wild type and opt cDNAs
Identity 100%

```
              10         20         30         40         50         60         70         80
rhp35w MCPARSLLIVATLVLLDYLSLARNLSVATPGPEMFPCLHHSQNLLKAASNTLQKARQILEFYPCTSEEIDHEDITKDKTS
       ::::::::::::::::::::::::::::::::::::::::::::::::::::::::::::::::::::::::::::::::
rhp35o MCPARSLLIVATLVLLDYLSLARNLSVATPGPEMFPCLHHSQNLLKAASNTLQKARQILEFYPCTSEEIDHEDITKDKTS
              10         20         30         40         50         60         70         80

90        100        110        120        130        140        150        160
rhp35w TVEACLPLELIKNESCLNSRETSFITNGSCLASRKTSFMMALCLRSIYEDLKMYQVEFKTMNAKLLRDPKRQIFLDQNIL
       ::::::::::::::::::::::::::::::::::::::::::::::::::::::::::::::::::::::::::::::::
rhp35o TVEACLPLELIKNESCLNSRETSFITNGSCLASRKTSFMMALCLRSIYEDLKMYQVEFKTMNAKLLRDPKRQIFLDQNIL
              90        100        110        120        130        140        150        160

170        180        190        200        210        220
rhp35w GVIDELMQALNFNSETVPQKSSLEEPDFYKTKIKLCILLHAFRIRAVTIDRVMSYLNAS
       :::::::::::::::::::::::::::::::::::::::::::::::::::::::::::
rhp35o GVIDELMQALNFNSETVPQKSSLEEPDFYKTKIKLCILLHAFRIRAVTIDRVMSYLNAS
             170        180        190        200        210        220
```

Figure 16

Comparison of rhesus IL12p40 proteins expressed from wild type and opt cDNAs
Identity 100%

```
            10         20         30         40         50         60         70         80
rhp40w  MCHQQLVISWFSLVFLASPLMAIWELKKDVYVVELDWYPDAPGEMVVLTCDTPEEDGITWTLDQSGEVLGSGKTLTIQVK
        ::::::::::::::::::::::::::::::::::::::::::::::::::::::::::::::::::::::::::::::::
rhp40o  MCHQQLVISWFSLVFLASPLMAIWELKKDVYVVELDWYPDAPGEMVVLTCDTPEEDGITWTLDQSGEVLGSGKTLTIQVK
            10         20         30         40         50         60         70         80

90        100        110        120        130        140        150        160
rhp40w  EFGDAGQYTCHKGGEALSHSLLLLHKKEDGIWSTDVLKDQKEPKNKTFLRCEAKNYSGRFTCWWLTTISTDLTFSVKSSR
        ::::::::::::::::::::::::::::::::::::::::::::::::::::::::::::::::::::::::::::::::
rhp40o  EFGDAGQYTCHKGGEALSHSLLLLHKKEDGIWSTDVLKDQKEPKNKTFLRCEAKNYSGRFTCWWLTTISTDLTFSVKSSR
            90        100        110        120        130        140        150        160

170        180        190        200        210        220        230        240
rhp40w  GSSNPQGVTCGAVTLSAERVRGDNKEYEYSVECQEDSACPAAEERLPIEVMVDAIHKLKYENYTSSFFIRDIIKPDPPKN
        ::::::::::::::::::::::::::::::::::::::::::::::::::::::::::::::::::::::::::::::::
rhp40o  GSSNPQGVTCGAVTLSAERVRGDNKEYEYSVECQEDSACPAAEERLPIEVMVDAIHKLKYENYTSSFFIRDIIKPDPPKN
           170        180        190        200        210        220        230        240

250        260        270        280        290        300        310        320
rhp40w  LQLKPLKNSRQVEVSWEYPDTWSTPHSYFSLTFCIQVQGKSKREKKDRIFTDKTSATVICRKNASFSVQAQDRYYSSSWS
        ::::::::::::::::::::::::::::::::::::::::::::::::::::::::::::::::::::::::::::::::
rhp40o  LQLKPLKNSRQVEVSWEYPDTWSTPHSYFSLTFCIQVQGKSKREKKDRIFTDKTSATVICRKNASFSVQAQDRYYSSSWS
           250        260        270        280        290        300        310        320 rhp40w  EWASVPCS
        ::::::::
rhp40o  EWASVPCS
           330
```

*Figure 17A*

Dual Promoter Vector

CCTGGCCATTGCATACGTTGTATCCATATCATAATATGTACATTTATATTGGCTCA
TGTCCAACATTACCGCCATGTTGACATTGATTATTGACTAGTTATTAATAGTAATC
AATTACGGGGTCATTAGTTCATAGCCCATATATGGAGTTCCGCGTTACATAACTT
ACGGTAAATGGCCCGCCTGGCTGACCGCCCAACGACCCCCGCCCATTGACGTCA
ATAATGACGTATGTTCCCATAGTAACGCCAATAGGGACTTTCCATTGACGTCAAT
GGGTGGAGTATTTACGGTAAACTGCCCACTTGGCAGTACATCAAGTGTATCATAT
GCCAAGTACGCCCCCTATTGACGTCAATGACGGTAAATGGCCCGCCTGGCATTAT
GCCCAGTACATGACCTTATGGGACTTTCCTACTTGGCAGTACATCTACGTATTAG
TCATCGCTATTACCATGGTGATGCGGTTTTGGCAGTACATCAATGGGCGTGGATA
GCGGTTTGACTCACGGGGATTTCCAAGTCTCCACCCCATTGACGTCAATGGGAGT
TTGTTTTGGCACCAAAATCAACGGGACTTTCCAAAATGTCGTAACAACTCCGCCC
CATTGACGCAAATGGGCGGTAGGCGTGTACGGTGGGAGGTCTATATAAGCAGAG
CTCGTTTAGTGAACCGTCAGATCGCCTGGAGACGCCATCCACGCTGTTTTGACCT
CCATAGAAGACACCGGGACCGATCCAGCCTCCGCGGGCGCGCGTCGAGGAATTC
GCTAGCGGCGCGCCAGATCTGATATCGGATCTGCTGTGCCTTCTAGTTGCCAGCC
ATCTGTTGTTTGCCCCTCCCCGTGCCTTCCTTGACCCTGGAAGGTGCCACTCCCA
CTGTCCTTTCCTAATAAAATGAGGAAATTGCATCGCATTGTCTGAGTAGGTGTCA
TTCTATTCTGGGGGGTGGGGTGGGGCAGGACAGCAAGGGGGAGGATTGGGAAGA
CAATAGCAGGCATGCTGGGGATGCGGTGGGCTCTATGGGTACCCAGGTGCTGAA
GAATTGACCCGGTTCCTCCTGGGCCAGAAAGAAGCAGGCACATCCCCTTCTCTGT
GACACACCCTGTCCACGCCCCTGGTTCTTAGTTCCAGCCCCACTCATAGGACACT
CATAGCTCAGGAGGGCTCCGCCTTCAATCCCACCCGCTAAAGTACTTGGAGCGGT
CTCTCCCTCCCTCATCAGCCCACCAAACCAAACCTAGCCTCCAAGAGTGGGAAGA
AATTAAAGCAAGATAGGCTATTAAGTGCAGAGGGAGAGAAAATGCCTCCAACAT
GTGAGGAAGTAATGAGAGAAATCATAGAATTTCTTCCGCTTCCTCGCTCACTGAC
TCGCTGCGCTCGGTCGTTCGGCTGCGGCGAGCGGTATCAGCTCACTCAAAGGCGG
TAATACGGTTATCCACAGAATCAGGGGATAACGCAGGAAAGAACATGTGAGCAA
AAGGCCAGCAAAAGGCCAGGAACCGTAAAAAGGCCGCGTTGCTGGCGTTTTTCC
ATAGGCTCCGCCCCCCTGACGAGCATCACAAAAATCGACGCTCAAGTCAGAGGT
GGCGAAACCCGACAGGACTATAAAGATACCAGGCGTTTCCCCCTGGAAGCTCCC
TCGTGCGCTCTCCTGTTCCGACCCTGCCGCTTACCGGATACCTGTCCGCCTTTCTC
CCTTCGGGAAGCGTGGCGCTTTCTCAATGCTCACGCTGTAGGTATCTCAGTTCGG
TGTAGGTCGTTCGCTCCAAGCTGGGCTGTGTGCACGAACCCCCCGTTCAGCCCGA
CCGCTGCGCCTTATCCGGTAACTATCGTCTTGAGTCCAACCCGGTAAGACACGAC
TTATCGCCACTGGCAGCAGCCACTGGTAACAGGATTAGCAGAGCGAGGTATGTA
GGCGGTGCTACAGAGTTCTTGAAGTGGTGGCCTAACTACGGCTACACTAGAAGG
ACAGTATTTGGTATCTGCGCTCTGCTGAAGCCAGTTACCTTCGGAAAAAGAGTTG
GTAGCTCTTGATCCGGCAAACAAACCACCGCTGGTAGCGGTGGTTTTTTTGTTTG
CAAGCAGCAGATTACGCGCAGAAAAAAGGATCTCAAGAAGATCCTTTGATCTT
TTCTACGGGGTCTGACGCTCAGTGGAACGAAAACTCACGTTAAGGGATTTTGGTC
ATGAGATTATCAAAAAGGATCTTCACCTAGATCCTTTTAAATTAAAAATGAAGTT
TTAAATCAATCTAAAGTATATATGAGTAAACTTGGTCTGACAGTTACCAATGCTT
AATCAGTGAGGCACCTATCTCAGCGATCTGTCTATTTCGTTCATCCATAGTTGCCT
GACTCGGGGGGGGGGGCGCTGAGGTCTGCCTCGTGAAGAAGGTGTTGCTGACT
CATACCAGGCCTGAATCGCCCCATCATCCAGCCAGAAAGTGAGGGAGCCACGGT

*Figure 17B*

TGATGAGAGCTTTGTTGTAGGTGGACCAGTTGGTGATTTTGAACTTTTGCTTTGCC
ACGGAACGGTCTGCGTTGTCGGGAAGATGCGTGATCTGATCCTTCAACTCAGCAA
AAGTTCGATTTATTCAACAAAGCCGCCGTCCCGTCAAGTCAGCGTAATGCTCTGC
CAGTGTTACAACCAATTAACCAATTCTGATTAGAAAAACTCATCGAGCATCAAAT
GAAACTGCAATTTATTCATATCAGGATTATCAATACCATATTTTTGAAAAAGCCG
TTTCTGTAATGAAGGAGAAAACTCACCGAGGCAGTTCCATAGGATGGCAAGATC
CTGGTATCGGTCTGCGATTCCGACTCGTCCAACATCAATACAACCTATTAATTTCC
CCTCGTCAAAAATAAGGTTATCAAGTGAGAAATCACCATGAGTGACGACTGAAT
CCGGTGAGAATGGCAAAAGCTTATGCATTTCTTTCCAGACTTGTTCAACAGGCCA
GCCATTACGCTCGTCATCAAAATCACTCGCATCAACCAAACCGTTATTCATTCGT
GATTGCGCCTGAGCGAGACGAAATACGCGATCGCTGTTAAAAGGACAATTACAA
ACAGGAATCGAATGCAACCGGCGCAGGAACACTGCCAGCGCATCAACAATATTT
TCACCTGAATCAGGATATTCTTCTAATACCTGGAATGCTGTTTTCCCGGGGATCG
CAGTGGTGAGTAACCATGCATCATCAGGAGTACGGATAAAATGCTTGATGGTCG
GAAGAGGCATAAATTCCGTCAGCCAGTTTAGTCTGACCATCTCATCTGTAACATC
ATTGGCAACGCTACCTTTGCCATGTTTCAGAAACAACTCTGGCGCATCGGGCTTC
CCATACAATCGATAGATTGTCGCACCTGATTGCCCGACATTATCGCGAGCCCATT
TATACCCATATAAATCAGCATCCATGTTGGAATTTAATCGCGGCCTCGAGCAAGA
CGTTTCCCGTTGAATATGGCTCATAACACCCCTTGTATTACTGTTTATGTAAGCAG
ACAGTTTTATTGTTCATGATGATATATTTTTATCTTGTGCAATGTAACATCAGAGA
TTTTGAGACACAACGTGGATCATCCAGACATGATAAGATACATTGATGAGTTTGG
ACAAACCACAACTAGAATGCAGTGAAAAAAATGCTTTATTTGTGAAATTTGTGAT
GCTATTGCTTTATTTGTAACCATTATAAGCTGCAATAAACAAGTTAACAACAACA
ATTGCATTCATTTTATGTTTCAGGTTCAGGGGGAGGTGTGGGAGGTTTTTTAAAG
CAAGTAAAACCTCTACAAATGTGGTATGGCTGATTATGATCGTCGAGGATCTGGA
TCTGGATCCGGCGCGCCTCTAGAGTTTAAACGTCGACACTCGACAGATCCAAACG
CTCCTCCGACGTCCCCAGGCAGAATGGCGGTTCCCTAAACGAGCATTGCTTATAT
AGACCTCCCATTAGGCACGCCTACCGCCCATTTACGTCAATGGAACGCCCATTTG
CGTCATTGCCCCTCCCCATTGACGTCAATGGGGATGTACTTGGCAGCCATCGCGG
GCCATTTACCGCCATTGACGTCAATGGGAGTACTGCCAATGTACCCTGGCGTACT
TCCAATAGTAATGTACTTGCCAAGTTACTATTAATAGATATTGATGTACTGCCAA
GTGGGCCATTTACCGTCATTGACGTCAATAGGGGGCGTGAGAACGGATATGAAT
GGGCAATGAGCCATCCCATTGACGTCAATGGTGGGTGGTCCTATTGACGTCAATG
GGCATTGAGCCAGGCGGGCCATTTACCGTAATTGACGTCAATGGGGGAGGCGCC
ATATACGTCAATAGGACCGCCCATATGACGTCAATAGGAAAGACCATGAGGCCC
TTTCGTCTCGCGCGTTTCGGTGATGACGGTGAAAACCTCTGACACATGCAGCTCC
CGGAGACGGTCACAGCTTGTCTGTAAGCGGATGCCGGGAGCAGACAAGCCCGTC
AGGGCGCGTCAGCGGGTGTTGGCGGGTGTCGGGGCTGGCTTAACTATGCGGCAT
CAGAGCAGATTGTACTGAGAGTGCACCATATGCGGTGTGAAATACCGCACAGAT
GCGTAAGGAGAAAATACCGCATCAGATTGGCTATTGG hCMV promoter
1 CCTGGCCATT GCATACGTTG TATCCATATC ATAATATGTA CATTTATATT GGCTCATGTC CAACATTACC

71 GCCATGTTGA CATTGATTAT TGACTAGTTA TTAATAGTAA TCAATTACGG GGTCATTAGT TCATAGCCCA

141 TATATGGAGT TCCGCGTTAC ATAACTTACG GTAAATGGCC CGCCTGGCTG ACCGCCCAAC GACCCCCGCC

211 CATTGACGTC AATAATGACG TATGTTCCCA TAGTAACGCC AATAGGGACT TTCCATTGAC GTCAATGGGT

281 GGAGTATTTA CGGTAAACTG CCCACTTGGC AGTACATCAA GTGTATCATA TGCCAAGTAC GCCCCCTATT

351 GACGTCAATG ACGGTAAATG GCCCGCCTGG CATTATGCCC AGTACATGAC CTTATGGGAC TTTCCTACTT

421 GGCAGTACAT CTACGTATTA GTCATCGCTA TTACCATGGT GATGCGGTTT TGGCAGTACA TCAATGGGCG

491 TGGATAGCGG TTTGACTCAC GGGGATTTCC AAGTCTCCAC CCCATTGACG TCAATGGGAG TTTGTTTTGG

561 CACCAAAATC AACGGGACTT TCCAAAATGT CGTAACAACT CCGCCCCATT GACGCAAATG GGCGGTAGGC

631 GTGTACGGTG GGAGGTCTAT ATAAGCAGAG CTCGTTTAGT GAACCGTCAG ATCGCCTGGA GACGCCATCC polylinker       Nhel (7
                                                                        SacII (749)     EcoRI (764)
701 ACGCTGTTTT GACCTCCATA GAAGACACCG GGACCGATCC AGCCTCCGCG GCGCGCGTC GAGGAATTCG EcoRV (792)
       BglII (784)         bovine growth hormone pA signal
771 CTAGCGGCGC GCCAGATCTG ATATCGGATC TGCTGTGCCT TCTAGTTGCC AGCCATCTGT TGTTTGCCCC

841 TCCCCCGTGC CTTCCTTGAC CCTGGAAGGT GCCACTCCCA CTGTCCTTTC CTAATAAAAT GAGGAAATTG

911 CATCGCATTG TCTGAGTAGG TGTCATTCTA TTCTGGGGGG TGGGGTGGGG CAGGACAGCA AGGGGGAGGA

981 TTGGGAAGAC AATAGCAGGC ATGCTGGGGA TGCGGTGGGC TCTATGGGTA CCCAGGTGCT GAAGAATTGA

1051 CCCGGTTCCT CCTGGGCCAG AAAGAAGCAG GCACATCCCC TTCTCTGTGA CACACCCTGT CCACGCCCCT

1121 GGTTCTTAGT TCCAGCCCCA CTCATAGGAC ACTCATAGCT CAGGAGGGCT CCGCCTTCAA TCCCACCCGC

1191 TAAAGTACTT GGAGCGGTCT CTCCCTCCCT CATCAGCCCA CCAAACCAAA CCTAGCCTCC AAGAGTGGGA

1261 AGAAATTAAA GCAAGATAGG CTATTAAGTG CAGAGGGAGA GAAAATGCCT CCAACATGTG AGGAAGTAAT

1331 GAGAGAAATC ATAGAATTTC TTCCGCTTCC TCGCTCACTG ACTCGCTGCG CTCGGTCGTT CGGCTGCGGC

1401 GAGCGGTATC AGCTCACTCA AAGGCGGTAA TACGGTTATC CACAGAATCA GGGGATAACG CAGGAAAGAA
                            ori of replication
1471 CATGTGAGCA AAAGGCCAGC AAAAGGCCAG GAACCGTAAA AAGGCCGCGT TGCTGGCGTT TTTCCATAGG 1541 CTCCGCCCCC CTGACGAGCA TCACAAAAAT CGACGCTCAA GTCAGAGGTG GCGAAACCCG ACAGGACTAT 1611 AAAGATACCA GGCGTTTCCC CCTGGAAGCT CCCTCGTGCG CTCTCCTGTT CCGACCCTGC CGCTTACCGG
1681 ATACCTGTCC GCCTTTCTCC CTTCGGGAAG CGTGGCGCTT TCTCAATGCT CACGCTGTAG GTATCTCAGT
1751 TCGGTGTAGG TCGTTCGCTC CAAGCTGGGC TGTGTGCACG AACCCCCCGT TCAGCCCGAC CGCTGCGCCT
1821 TATCCGGTAA CTATCGTCTT GAGTCCAACC CGGTAAGACA CGACTTATCG CCACTGGCAG CAGCCACTGG
1891 TAACAGGATT AGCAGAGCGA GGTATGTAGG CGGTGCTACA GAGTTCTTGA AGTGGTGGCC TAACTACGGC
1961 TACACTAGAA GGACAGTATT TGGTATCTGC GCTCTGCTGA AGCCAGTTAC CTTCGGAAAA AGAGTTGGTA
2031 GCTCTTGATC CGGCAAACAA ACCACCGCTG GTAGCGGTGG TTTTTTTGTT TGCAAGCAGC AGATTACGCG
2101 CAGAAAAAAA GGATCTCAAG AAGATCCTTT GATCTTTTCT ACGGGGTCTG ACGCTCAGTG GAACGAAAAC
2171 TCACGTTAAG GGATTTTGGT CATGAGATTA TCAAAAAGGA TCTTCACCTA GATCCTTTTA AATTAAAAAT
2241 GAAGTTTTAA ATCAATCTAA AGTATATATG AGTAAACTTG GTCTGACAGT TACCAATGCT TAATCAGTGA
2311 GGCACCTATC TCAGCGATCT GTCTATTTCG TTCATCCATA GTTGCCTGAC TCGGGGGGGG GGGGCGCTGA
2381 GGTCTGCCTC GTGAAGAAGG TGTTGCTGAC TCATACCAGG CCTGAATCGC CCCATCATCC AGCCAGAAAG
2451 TGAGGGAGCC ACGGTTGATG AGAGCTTTGT TGTAGGTGGA CCAGTTGGTG ATTTTGAACT TTTGCTTTGC
2521 CACGGAACGG TCTGCGTTGT CGGGAAGATG CGTGATCTGA TCCTTCAACT CAGCAAAAGT TCGATTTATT
2591 CAACAAAGCC GCCGTCCCGT CAAGTCAGCG TAATGCTCTG CCAGTGTTAC AACCAATTAA CCAATTCTGA
                                                                                                                                                                                                                           2724
2661 TTAGAAAAAC TCATCGAGCA TCAAATGAAA CTGCAATTTA TTCATATCAG GATTATCAAT ACCATATTTT
2724  • F  F    E  D  L  M    L  H  F    Q  L  K    N  M  D  P    N  D  I    G  Y  K
2731 TGAAAAAGCC GTTTCTGTAA TGAAGGAGAA AACTCACCGA GGCAGTTCCA TAGGATGGCA AGATCCTGGT
2484 Q  F  L  R    K  Q  L    S  P  S    F  E  G  L    C  N  W    L  I  A    L  D  Q  Y
2801 ATCGGTCTGC GATTCCGACT CGTCCAACAT CAATACAACC TATTAATTTC CCCTCGTCAA AAATAAGGTT
2254 R  D  A    I  G  V    R  G  V  D    I  C  G    I  L  K    E  D  F    I  L  N
2871 ATCAAGTGAG AAATCACCAT GAGTGACGAC TGAATCCGGT GAGAATGGCA AAAGCTTATG CATTTCTTTC
2024 D  L  S    F  D  G  H    T  V  V    S  D  P    S  F  P  L    L  K  H    M  E  K
2941 CAGACTTGTT CAACAGGCCA GCCATTACGC TCGTCATCAA AATCACTCGC ATCAACCAAA CCGTTATTCA
1784 W  V  Q  E    V  P  W    G  N  R    E  D  D  F    D  S  A    D  V  L    G  N  N  M
3011 TTCGTGATTG CGCCTGAGCG AGACGAAATA CGCGATCGCT GTTAAAGGA CAATTACAAA CAGGAATCGA
1554 R  S  Q    A  Q  A    L  R  F  V    R  D  S    N  F  P    C  N  C  V    P  I  S
3081 ATGCAACCGG CGCAGGAACA CTGCCAGCGC ATCAACAATA TTTTCACCTG AATCAGGATA TTCTTCTAAT
1324 H  L  R    R  L  F  V    A  L  A    D  V  I    N  E  G  S    D  P  Y    E  E  L
3151 ACCTGGAATG CTGTTTTCCC GGGGATCGCA GTGGTGAGTA ACCATGCATC ATCAGGAGTA CGGATAAAAT
1084 V  Q  F  A    T  K  G    P  I  A    T  T  L  L    W  A  D    D  P  T    R  I  F  H
3221 GCTTGATGGT CGGAAGAGGC ATAAATTCCG TCAGCCAGTT TAGTCTGACC ATCTCATCTG TAACATCATT
854 K  I  T    P  L  P    M  F  E  T    L  W  N    L  R  V    M  E  D  T    V  D  N
3291 GGCAACGCTA CCTTTGCCAT GTTTCAGAAA CAACTCTGGC GCATCGGGCT TCCCATACAA TCGATAGATT
624 A  V  S    G  K  G  H    K  L  F    L  E  P    A  D  P  K    G  Y  L    R  Y  I
3361 GTCGCACCTG ATTGCCCGAC ATTATCGCGA GCCCATTTAT CCCATATAA ATCAGCATCC ATGTTGGAAT
384 T  A  G  S    Q  G  V    N  D  R    A  W  K  Y    G  Y  L    D  A  D    M  N  S  N
                                                                               kanamycin gene
3431 TTAATCGCGG CCTCGAGCAA GACGTTTCCC GTTGAATATG GCTCATAACA CCCCTTGTAT TACTGTTTAT
154 L  R  P    R  S  C    S  T  E  R    Q  I  H  S  M

Figure 18A

```
3641 GTGAAAAAAA TGCTTTATTT GTGAAATTTG TGATGCTATT GCTTTATTTG TAACCATTAT AAGCTGCAAT

3711 AAACAAGTTA ACAACAACAA TTGCATTCAT TTTATGTTTC AGGTTCAGGG GGAGGTGTGG GAGGTTTTTT
                                                                    polylinker
                                                    SV40 pA signal          BamHI (3843)
3781 AAAGCAAGTA AAACCTCTAC AAATGTGGTA TGGCTGATTA TGATCGTCGA GGATCTGGAT CTGGATCCGG
                                                                    ◀
                      HincII (3873)
                      SalI (3871)
            PmeI (3866)
    XbaI (3857)      AccI (3872)
3851 CGCGCCTCTA GAGTTTAAAC GTCGACACTC GACAGATCCA AACGCTCCTC CGACGTCCCC AGGCAGAATG
                                          ◀
3921 GCGGTTCCCT AAACGAGCAT TGCTTATATA GACCTCCCAT TAGGCACGCC TACCGCCCAT TTACGTCAAT 3991 GGAACGCCCA TTTGCGTCAT TGCCCCTCCC CATTGACGTC AATGGGGATG TACTTGGCAG CCATCGCGGG 4061 CCATTTACCG CCATTGACGT CAATGGGAGT ACTGCCAATG TACCCTGGCG TACTTCCAAT AGTAATGTAC 4131 TTGCCAAGTT ACTATTAATA GATATTGATG TACTGCCAAG TGGGCCATTT ACCGTCATTG ACGTCAATAG 4201 GGGGCGTGAG AACGGATATG AATGGGCAAT GAGCCATCCC ATTGACGTCA ATGGTGGGTG GTCCTATTGA 4271 CGTCAATGGG CATTGAGCCA GGCGGGCCAT TTACCGTAAT TGACGTCAAT GGGGGAGGCG CCATATACGT
                                                    Simian CMV promoter (4380)
4341 CAATAGGACC GCCCATATGA CGTCAATAGG AAAGACCATG AGGCCCTTTC GTCTCGCGCG TTTCGGTGAT 4411 GACGGTGAAA ACCTCTGACA CATGCAGCTC CCGGAGACGG TCACAGCTTG TCTGTAAGCG GATGCCGGGA
4481 GCAGACAAGC CCGTCAGGGC GCGTCAGCGG GTGTTGGCGG GTGTCGGGGC TGGCTTAACT ATGCGGCATC
4551 AGAGCAGATT GTACTGAGAG TGCACCATAT GCGGTGTGAA ATACCGCACA GATGCGTAAG GAGAAAATAC
4621 CGCATCAGAT TGGCTATTGG
```

IL-12 FOR EXPRESSION IN MAMMALIAN CELL

CROSS-REFERENCE TO RELATED APPLICATIONS

The present application is the U.S. National Stage entry of International Application No. PCT/US07/000825, filed Jan. 12, 2007, which claims the benefit of U.S. Provisional Patent Application No. 60/758,680, filed on Jan. 13, 2006, the entire contents of each of which are hereby incorporated herein by reference for all purposes.

FIELD OF THE INVENTION

The present invention relates to improved cytokine expression in mammalian cells by optimizing all steps of gene expression of the cytokine.

BACKGROUND OF THE INVENTION

Interleukin-12 (IL-12) is a proinflammatory cytokine that induces the production of interferon-gamma (IFN-γ), promotes the differentiation of T helper-1 (Th1) cells and connects innate and adaptive immune response pathways (Trinchieri, Nat Rev Immunol (2003) 3:133). IL-12 is produced by dendritic cells (DC) and phagocytes (e.g., macrophages, neutrophils, immature dendritic cells) in response to pathogens during infection (Id.). Structurally, IL-12 is a heterodimeric protein comprised of two polypeptide chains, a p35 chain and a p40 chain (Airoldi, et al., Haematologica (2002) 87:434-42). IL-12 is structurally related to at least two other heterodimeric proinflammatory cytokines, interleukin-23 (IL-23) and interleukin-27 (IL-27) (Hunter, Nat Rev Immunol (2005) 5:521; and Vandenbroeck, et al., J Pharm Pharmacol (2004) 56:145).

Cytokines, including IL-12, play a critical role as molecular adjuvants for vaccines to induce improved immune responses. IL-12 has been shown to increase the magnitude of vaccine-induced immune responses (see, for example, Tomioka, Curr Pharm Des (2004) 10:3297; El-Aneed, Eur J Pharmacol (2004) 498:1; Stevceva, Curr Pharm Des (2005) 11:801; and Toka, et al, Immunol Rev (2004)199:100). To provide IL-12 as molecular adjuvant, it is important to develop efficient expression vectors and efficiently expressing coding nucleic acid sequences for this cytokine. The present invention addresses this need.

BRIEF SUMMARY OF THE INVENTION

The present invention provides nucleic acid sequences, expression vectors and mammalian cells for the high-level expression of interleukin-12. The invention further provides methods for the high-level expression of interleukin-12 in mammalian cells.

Accordingly, in a first aspect, the invention provides a nucleic acid sequence pair encoding an interleukin-12 (IL-12) protein heterodimer comprised of an IL-12p35 and an IL-12p40, the IL-12p35 and the IL-12p40 each having at least 95%, 96%, 97%, 98%, 99% sequence identity to a native mammalian IL-12 protein heterodimer, wherein the nucleic acid sequence encoding the IL-12p35 differs from a nucleic acid sequence encoding the native IL-12p35 by at least 50% of the 136 changed codons identified in FIG. 6 (e.g., at least about 68 of 136), wherein the nucleic acid sequence encoding the IL-12p40 differs from a nucleic acid sequence encoding the native IL-12p40 by at least 50% of the 197 changed codons identified in FIG. 8 (e.g., at least about 98 of 197). The native mammalian IL-12 heterodimer can be any mammalian IL-12, including human IL-12, a primate IL-12, a porcine IL-12, a murine IL-12, and the like.

In some embodiments, the nucleic acid sequence encoding the IL-12p35 differs from a nucleic acid sequence encoding the native IL-12p35 by at least about 55% (e.g. 75 codons), 60% (e.g., 82 codons), 65% (e.g., 89 codons), 70% e.g., (95 codons), 75% (e.g., 102 codons), 80% (e.g., 109 codons), 85% (e.g., 116 codons), 90% (e.g., 122 codons), 95% (e.g., 129 codons) of the 136 changed codons identified in FIG. 6, and the nucleic acid sequence encoding the IL-12p40 differs from a nucleic acid sequence encoding the native IL-12p40 by at least about 55% (e.g., 108 codons), 60% (e.g., 118 codons), 65% (e.g., 128 codons), 70% (e.g., 138 codons), 75% (e.g., 147 codons), 80% (e.g., 157 codons), 85% (e.g., 167 codons), 90% (e.g., 177 codons), 95% (e.g., 187 codons) of the 197 changed codons identified in FIG. 8.

In some embodiments, the nucleic acid sequence encoding the IL-12p35 differs from a nucleic acid sequence encoding the native IL-12p35 at codon numbers 2, 3, 6, 7, 8, 9, 11, 12, 15, 16, 19, 20, 21, 22, 23, 25, 26, 28, 29, 30, 32, 33, 36, 38, 41, 42, 46, 47, 48, 49, 52, 55, 56, 57, 58, 59, 60, 61, 63, 65, 66, 67, 69, 70, 71, 72, 73, 75, 76, 77, 78, 81, 84, 85, 86, 87, 88, 89, 90, 91, 93, 95, 97, 98, 99, 100, 102, 103, 105, 106, 107, 109, 112, 113, 114, 116, 117, 118, 121, 124, 125, 126, 127, 128, 129, 131, 140, 142, 143, 145, 148, 149, 151, 154, 155, 156, 157, 161, 162, 163, 164, 166, 169, 170, 171, 174, 176, 178, 179, 180, 181, 182, 183, 184, 185, 187, 188, 189, 190, 191, 192, 197, 198, 199, 200, 203, 204, 206, 208, 209, 210, 211, 214, 215, 217 and 219, wherein the codon numbers are as identified in FIG. 6, and wherein the nucleic acid sequence encoding the IL-12p40 differs from a nucleic acid sequence encoding the native IL-12p40 at codon numbers 2, 6, 9, 11, 12, 13, 15, 16, 17, 18, 19, 20, 21, 25, 26, 28, 29, 30, 31, 32, 33, 34, 35, 36, 38, 39, 40, 41, 42, 43, 44, 46, 48, 49, 50, 52, 53, 54, 55, 56, 57, 59, 61, 62, 65, 66, 69, 71, 73, 74, 75, 76, 78, 80, 82, 83, 84, 85, 89, 90, 92, 93, 96, 97, 99, 100, 102, 104, 106, 108, 109, 110, 111, 113, 114, 115, 116, 117, 121, 122, 123, 124, 125, 128, 129, 130, 133, 136, 137, 138, 139, 141, 145, 146, 147, 149, 150, 151, 152, 153, 155, 157, 158, 159, 160, 162, 163, 166, 169, 171, 172, 173, 174, 175, 176, 177, 179, 180, 181, 182, 187, 190, 191, 197, 198, 200, 201, 202, 205, 207, 208, 210, 212, 213, 214, 215, 218, 220, 221, 224, 225, 226, 230, 234, 235, 237, 238, 241, 245, 246, 248, 249, 252, 255, 259, 261, 263, 264, 265, 266, 267, 270, 272, 275, 276, 277, 281, 283, 284, 286, 287, 288, 289, 291, 294, 295, 296, 298, 301, 302, 303, 304, 305, 306, 307, 310, 313, 315, 316, 317, 318, 320, 321, 323, 324, 326 and 328, wherein the codon numbers are as identified in FIG. 8.

The codons can differ in any way such that an identical or similar amino acid is encoded. In some embodiments, the codons are changed to increase GC content. In some embodiments, the improved IL-12p35 and IL-12p40 nucleic acid sequences each comprise at least about 55%, 60%, 65%, 70% or 75% or more GC content (e.g., deoxyguanosine and deoxycytidine deoxyribonucleoside residues or guanosine and cytidine ribonucleoside residues) over the length of the sequence.

In some embodiments, the nucleic acid sequence encoding the IL-12p35 differs from a nucleic acid sequence encoding the native IL-12p35 as identified in FIG. 6 (SEQ ID NO:3). In some embodiments, the nucleic acid sequence encoding the IL-12p40 differs from a nucleic acid sequence encoding the native IL-12p40 as identified in FIG. 8 (SEQ ID NO:6).

In a further aspect, the invention further includes expression vectors and mammalian cells comprising the nucleic acid sequences of the invention, including the embodiments described above.

In some embodiments, the nucleic acid sequence pair further includes pharmaceutical excipients for use as a vaccine adjuvant.

In another aspect, the invention provides methods for expressing IL-12 in a mammalian cell, the method comprising introducing a recombinant vector into a mammalian cell to express a nucleic acid sequence pair encoding an IL-12 protein heterodimer comprised of an IL-12p35 and an IL-12p40, the IL-12p35 and the IL-12p40 each having at least 95%, 96%, 97%, 98%, 99% sequence identity to a native mammalian IL-12 protein heterodimer, wherein the nucleic acid sequence encoding the IL-12p35 differs from a nucleic acid sequence encoding the native IL-12p35 by at least 50% of the codons identified in FIG. 6, wherein the nucleic acid sequence encoding the IL-12p40 differs from a nucleic acid sequence encoding the native IL-12p40 by at least 50% of the codons identified in FIG. 8. The embodiments for the methods are the same as described above for the nucleic acid sequences.

DEFINITIONS

The terms "IL-12 protein heterodimer" or "IL-12 heterodimer" or "IL-12p70" refer to an IL-12 cytokine protein composed of its two monomeric polypeptide subunits, an IL-12p35 chain and an IL-12p40 chain. See, for example, Airoldi, et al., *Haematologica* (2002) 87:434-42.

The term "native mammalian IL-12" refers to any naturally occurring interleukin-12 nucleic acid and amino acid sequences of the IL-12 monomeric sequences, IL-12p35 and IL-12p40 from a mammalian species. Those of skill in the art will appreciate that interleukin-12 sequences are publicly available in gene databases, for example, GenBank through the National Center for Biotechnological Information on the worldwideweb at ncbi.nlm.nih.gov/entrez/query.fcgi?db=Nucleotide and ncbi.nlm.nih.gov/entrez/query.fcgi?db=Protein. Exemplified native mammalian IL-12 nucleic acid or amino acid sequences can be from, for example, human, primate, canine, feline, porcine, equine, bovine, ovine, rodentia, murine, rat, hamster, guinea pig, etc. Accession numbers for exemplified native mammalian IL-12 nucleic acid sequences include NM_002187 (human p40, SEQ ID NO:4), NM_000882 (human p35, SEQ ID NO:1), AY234218 (baboon p40), AY234219 (baboon p35); U19841 (rhesus monkey p40, SEQ ID NO:10), U19842 (rhesus monkey p35, SEQ ID NO:7); NM_022611 (rat p40), NM_053390 (rat p35), and NM_008352 (mouse p40), NM_008351 (mouse p35). Accession numbers for exemplified native mammalian IL-12 amino acid sequences include NP_002178 (human p40, SEQ ID NO:5), NP_000873 (human p35), AAK84425 or AAD56385 (human p35, SEQ ID NO:2); AAA86707 (rhesus monkey p35; SEQ ID NO:8); P48095 (rhesus monkey p40, SEQ ID NO:11); NP_072133 (rat p40), AAD51364 (rat p35), and NP_032378 (mouse p35), NP_032377 (mouse p40).

The term "interleukin-12" or "IL-12" refers to a polypeptide that has at least 90%, 91%, 92%, 93%, 94%, 95%, 96%, 97%, 98% or 99% sequence identity to a native mammalian IL-12 amino acid sequence, or a nucleotide encoding such a polypeptide, is biologically active, meaning the mutated protein ("mutein") has functionality similar (75% or greater) to that of a native IL-12 protein in at least one functional assay. Exemplified functional assays of an IL-12 polypeptide include inducing the production of interferon-gamma (IFN-γ), for example, by T cells or natural killer (NK) cells, and promoting the differentiation of T helper-1 (Th1) cells. A T helper cell differentiated into a Th1 cell can be identified by secretion of IFN-γ. IFN-γ secreted by IL-12 stimulated T cells or NK cells can be conveniently detected, for example, in serum or cell culture supernatant using ELISA. ELISA methods and techniques are well known in the art, and kits for detecting IFN-γ are commercially available (e.g., R&D Systems, Minneapolis, Minn.; Peprotech, Rocky Hill, N.J.; and Biosource Intl., Camarillo, Calif.) See also, Coligan, et al., Current Methods in Immunology, 1991-2006, John Wiley & Sons; Harlow and Lane, *Using Antibodies: A Laboratory Manual,* 1998, Cold Spring Harbor Laboratory Press; and *The ELISA Guidebook*, Crowther, ed., 2000, Humana Press.

The term "nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Degenerate codon substitutions can be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

Degenerate codon substitutions for naturally occurring amino acids are in Table 1.

TABLE 1

| 1st position | 2nd position | | | | 3rd position |
|---|---|---|---|---|---|
| (5' end) | U(T) | C | A | G | (3' end) |
| U(T) | Phe | Ser | Tyr | Cys | U(T) |
| | Phe | Ser | Tyr | Cys | C |
| | Leu | Ser | STOP | STOP | A |
| | Leu | Ser | STOP | Trp | G |
| C | Leu | Pro | His | Arg | U(T) |
| | Leu | Pro | His | Arg | C |
| | Leu | Pro | Gln | Arg | A |
| | Leu | Pro | Gln | Arg | G |
| A | Ile | Thr | Asn | Ser | U(T) |
| | Ile | Thr | Asn | Ser | C |
| | Ile | Thr | Lys | Arg | A |
| | Met | Thr | Lys | Arg | G |
| G | Val | Ala | Asp | Gly | U(T) |
| | Val | Ala | Asp | Gly | C |
| | Val | Ala | Glu | Gly | A |
| | Val | Ala | Glu | Gly | G |

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, 91%, 92%, 93%, 94%, 95%, 96%, 97%, 98%, 99%, or higher identity over a specified region (e.g., any one of SEQ ID NOs:1-23), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or can be applied to, the compliment of a test sequence. The definition also includes sequences that have deletions and/or additions, as well as those that have substitutions. As described below, the preferred algorithms can account for gaps and the like. Preferably, identity exists over a region that is at least about 25, 50, 75, 100, 150, 200 amino acids or nucleotides in length, and oftentimes over a region that is 225, 250, 300, 350, 400, 450, 500 amino acids or nucleotides in length or over the full-length of am amino acid or nucleic acid sequences.

For sequence comparison, typically one sequence acts as a reference sequence, to which test sequences are compared (here, an entire "native mammalian" IL-12 p35 or IL-12 p40 amino acid or nucleic acid sequence). When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A preferred example of algorithm that is suitable for determining percent sequence identity and sequence similarity are the BLAST algorithms, which are described in Altschul et al., *Nuc. Acids Res.* 25:3389-3402 (1977) and Altschul et al., *J. Mol. Biol.* 215:403-410 (1990), respectively. BLAST software is publicly available through the National Center for Biotechnology Information on the worldwide web at ncbi.nlm.nih.gov/. Both default parameters or other non-default parameters can be used. The BLASTN program (for nucleotide sequences) uses as defaults a wordlength (W) of 11, an expectation (E) of 10, M=5, N=-4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=-4, and a comparison of both strands.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

"Conservatively modified variants" as used herein applies to amino acid sequences. One of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins (1984)).

The term "GC content" refers to the percentage of a nucleic acid sequence comprised of deoxyguanosine (G) and/or deoxycytidine (C) deoxyribonucleosides, or guanosine (G) and/or cytidine (C) ribonucleoside residues.

The terms "mammal" or "mammalian" refer to any animal within the taxonomic classification mammalia. A mammal can refer to a human or a non-human primate. A mammal can refer to a domestic animal, including for example, canine, feline, rodentia, including lagomorpha, murine, rattus, Cricetinae (hamsters), etc. A mammal can refer to an agricultural animal, including for example, bovine, ovine, porcine, equine, etc.

BRIEF DESCRIPTION OF THE DRAWINGS

FIG. 5 illustrates an alignment of human IL-12p35, comparing a wild-type IL-12p35 sequence (huIL12p35, SEQ ID NO:1) to an improved IL-12p35 nucleic acid sequence (huIL12p35opt, SEQ ID NO:3). The exemplified improved IL-12p35 nucleic acid sequence shares about 75% sequence identity (i.e., 75.9%) with the wild-type IL-12p35 sequence, or identity of 501 of 660 nucleotide bases.

FIG. 6 illustrates a codon usage comparison between human wild-type IL-12p35 (SEQ ID NO:1) and improved IL-12p35 (SEQ ID NO:3) nucleic acid sequences. The improved human IL-12p35 sequence was changed at 136 of 219 codons. The boxed codons indicate codons changed to "more preferred" codons according to the method of Seed (U.S. Pat. No. 5,786,464) (65 codons). The underlined codons indicate codons changed to "less preferred" codons according to the classification of Seed (8 codons), in contradiction to the method of Seed. The grey highlighted codons indicate codons "not preferred" according to the method of Seed (63 codons), also in contradiction to the method of Seed.

FIGS. 7A and 7B illustrate an alignment of human IL-12p40, comparing a wild-type IL-12p40 sequence (huIL12p40, SEQ ID NO:4) to an improved IL-12p40 nucleic acid sequence (huIL12p40opt, SEQ ID NO:6). The exemplified improved IL-12p40 nucleic acid sequence shares about 75% sequence identity (i.e., 75.7%) with the wild-type IL-12p35 sequence, or identity of 747 of 987 nucleotide bases.

FIG. 8 illustrates a codon usage comparison between human wild-type IL-12p40 (SEQ ID NO:4) and improved IL-12p40 (SEQ ID NO:6) nucleic acid sequences. The improved human IL-12p40 sequence was changed at 199 of 328 codons. The boxed codons indicate codons changed to more preferred codons according to the method of Seed (U.S. Pat. No. 5,786,464) (92 codons). The underlined codons indicate codons changed to less preferred codons according to the method of Seed (10 codons). The grey highlighted codons indicate codons not preferred according to the method of Seed (94 codons).

FIG. 10 illustrates an alignment of Rhesus monkey (i.e., *Macaca mulatta*) IL-12p35, comparing a wild-type IL-12p35 sequence (rhIL12p35, SEQ ID NO:7) to an improved IL-12p35 nucleic acid sequence (rhIL12p35opt, SEQ ID NO:9). The exemplified improved IL-12p35 nucleic acid sequence shares about 77% sequence identity with the wild-type IL-12p35 sequence.

FIG. 11 illustrates an alignment of Rhesus monkey IL-12p40, comparing a wild-type IL-12p40 sequence (p40 wt, SEQ ID NO:10) to an improved IL-12p40 nucleic acid sequence (p40opt, SEQ ID NO:12). The exemplified improved IL-12p40 nucleic acid sequence shares about 80% sequence identity with the wild-type IL-12p40 sequence.

FIG. 13 shows 100% sequence identity between the human IL-12p35 amino acid sequences encoded by the human wild-type IL-12p35 (p35 wt) and improved IL-12p35 (p35opt) nucleic acid sequences (SEQ ID NO:2). The underlined sequence indicates the signal peptide sequence for human IL-12p35. See, SEQ ID NOs:14-18.

FIG. 14 shows 100% sequence identity between the human IL-12p40 amino acid sequences encoded by the human wild-type IL-12p40 (p40 wt) and improved IL-12p40 (p40opt) nucleic acid sequences (SEQ ID NO:5). The underlined sequence indicates the signal peptide sequence for human IL-12p40. See, SEQ ID NOs:19-23.

FIG. 15 shows 100% sequence identity between the Rhesus monkey IL-12p35 amino acid sequences encoded by the Rhesus monkey wild-type IL-12p35 (rhp35w) and improved IL-12p35 (rhp35o) nucleic acid sequences (SEQ ID NO:8).

FIG. 16 shows 100% sequence identity between the Rhesus monkey IL-12p40 amino acid sequences encoded by the Rhesus monkey wild-type IL-12p40 (rhp40w) and improved IL-12p40 (rhp40o) nucleic acid sequences (SEQ ID NO:11).

FIGS. 17A and 17B illustrate a nucleic acid sequence of a dual promoter vector of the invention (SEQ ID NO:13).

FIGS. 18A and 18B illustrate a sequence map of a dual promoter vector of the invention (SEQ ID NO:24). Kanamycin marker=SEQ ID NO:25.

DETAILED DESCRIPTION

1. Introduction

Figure 1:
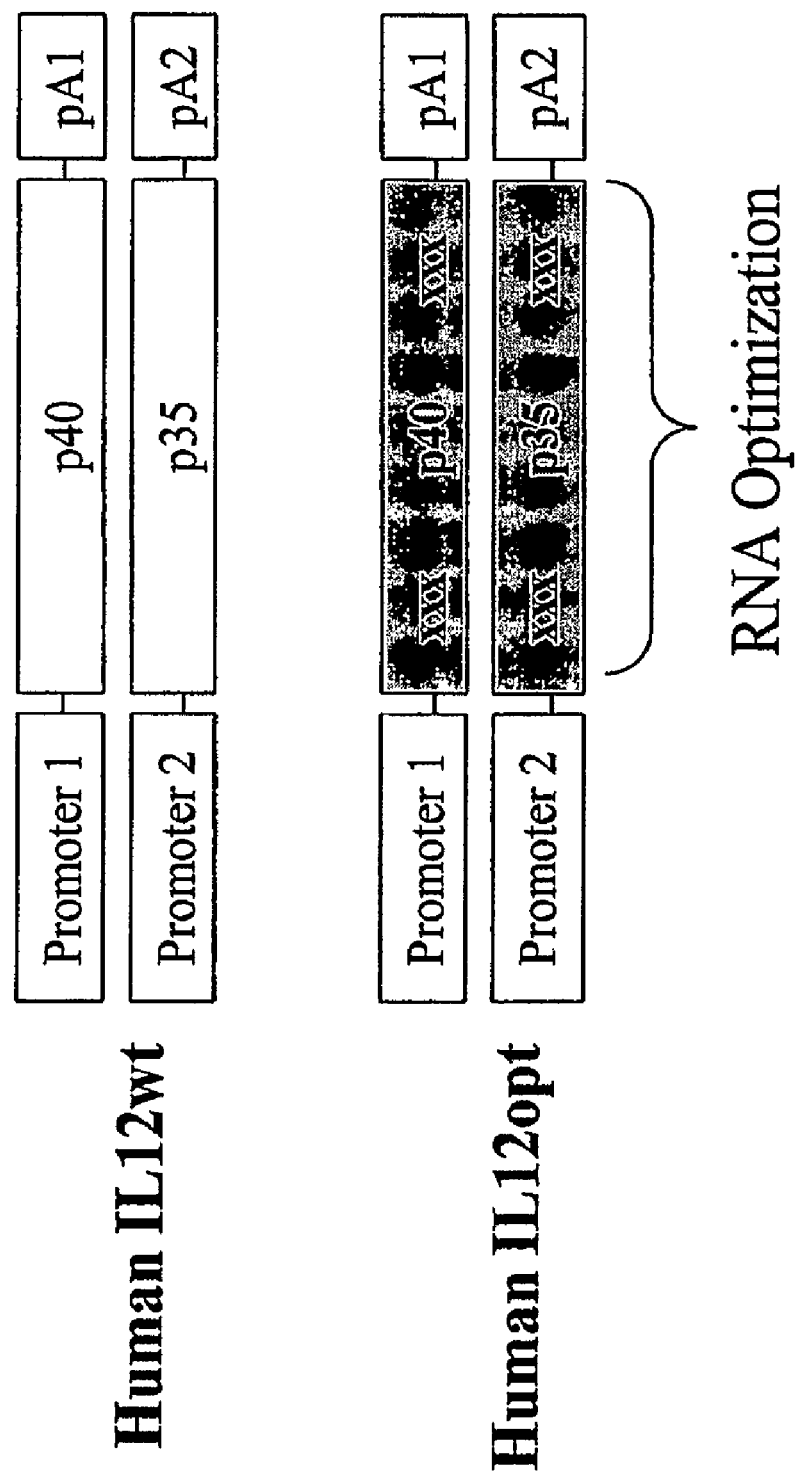
FIG. 1 illustrates a schematic of optimization and modulation of human IL-12. Both chains (i.e. IL-12p35 and IL-12p40) are expressed from a dual promoter plasmid utilizing distinct promoters and polyadenylation signals.

The cytokine interleukin-12 finds use as a vaccine adjuvant, particularly when co-administered with antigen as a nucleic acid that expresses IL-12. Native IL-12 sequences do not express IL-12 heterodimer optimally because of several different reasons, including signals within the RNA sequence such as potential splice sites and low stability determinants (oftentimes A/T or A/U rich) sequences embedded within the coding sequences. By minimizing potential splice sites and low stability sequences from IL-12 sequences, expression of IL-12 heterodimeric protein can be increased as much as 3-fold, 4-fold, 5-fold, 6-fold, or more in comparison to expression from native mammalian IL-12 sequences. A general method has been established for this purpose, comprising changing several codons of the encoded mRNA to alternative codons encoding the same amino acid (see, e.g., U.S. Pat. Nos. 5,965,726; 5,972,596; 6,174,666; 6,291,664; 6,414,132; and 6,794,498, the disclosures of each of which are hereby incorporated herein by reference in their entirety for all purposes). This results in the change of any negatively acting signals embedded into the RNA without altering the produced protein (see, FIG. 1).

2. Nucleic Acid Sequences

The improved high expressing IL-12 nucleic acid sequences of the invention are usually based on a native mammalian interleukin-12 coding sequence as a template. Nucleic acids sequences encoding native interleukin-12 can be readily found in publicly available databases including nucleotide, protein and scientific databases available on the worldwide web through the National Center for Biotechnology Information at ncbi.nlm.nih.gov. Native IL-12 nucleic acid sequences can be conveniently cloned from mammalian B-lymphoblastoid cells, macrophages or monocytes following appropriate stimulation (Brunda, *J Leukoc Biol.* (1994) 55:280-8). Protocols for isolation and stimulation of desired immune cell populations are well known in the art. See, for example, *Current Protocols in Immunology*, Coligan, et al., eds., 1991-2005, John Wiley & Sons.

The sequences are modified according to methods that simultaneously rectify several factors affecting mRNA traffic, stability and expression. Codons are altered to change the overall mRNA AT(AU)-content, to minimize or remove all potential splice sites, and to alter any other inhibitory sequences and signals affecting the stability and processing of mRNA such as runs of A or T/U nucleotides, AATAAA, ATTTA and closely related variant sequences, known to negatively affect mRNA stability. The methods applied to IL-12 coding nucleic acid sequences in the present application have been described in U.S. Pat. Nos. 6,794,498; 6,414,132; 6,291, 664; 5,972,596; and 5,965,726 the disclosures of each of which are hereby incorporated herein by reference in their entirety for all purposes.

Generally, the changes to the nucleotide bases or codons of a coding IL-12 sequence do not alter the amino acid sequence of the translated monomers comprising an IL-12 heterodimer from the native IL-12 p35 and p40 subunit polypeptides (see, FIGS. 13-16). The changes are based upon the degeneracy of the genetic code, utilizing an alternative codon for an identical amino acid, as summarized in Table 1, above. In certain embodiments, it will be desirable to alter one or more codons to encode a similar amino acid residue rather than an identical amino acid residue. Applicable conservative substitutions of coded amino acid residues are described above.

Oftentimes, in carrying out the present methods for increasing the stability of an IL-12 coding sequence, a relatively more A/T-rich codon of a particular amino acid is replaced with a relatively more G/C rich codon encoding the same amino acid (see, for example, FIGS. 3-8, 10-11). For example, amino acids encoded by relatively more A/T-rich and relatively more G/C rich codons are shown in Table 2.

TABLE 2

| Amino Acid | relatively more A/T-rich codon(s) | relatively more G/C-rich codon(s) |
|---|---|---|
| Ala | GCA, GCT | GCC, GCG |
| Asn | AAT | AAC |
| Asp | GAT | GAC |
| Arg | CGA, CGT, AGA | CGC, CGG, AGG |
| Cys | TGT | TGC |
| Gln | CAA | CAG |
| Glu | GAA | GAG |
| Gly | GGA, GGT | GGC, GGG |
| His | CAT | CAC |
| Ile | ATA, ATT | ATC |
| Leu | TTA, CTA, CTT | TTG, CTC, CTG |
| Lys | AAA | AAG |
| Phe | TTT | TTC |
| Pro | CCA, CCT | CCC, CCG |
| Ser | TCA, TCT, AGT | TCC, TCG, AGC |
| Thr | ACA, ACT | ACC, ACG |
| Tyr | TAT | TAC |
| Val | GTA, GTT | GTC, GTG |

Depending on the number of changes introduced, the improved IL-12 nucleic acid sequences of the present invention can be conveniently made as completely synthetic sequences. Techniques for constructing synthetic nucleic acid sequences encoding a protein or synthetic gene sequences are well known in the art. Synthetic gene sequences can be commercially purchased through any of a number of service companies, including DNA 2.0 (Menlo Park, Calif.), Geneart (Toronto, Ontario, Canada), CODA Genomics (Irvine, Calif.), and GenScript, Corporation (Piscataway, N.J.). Alternatively, codon changes can be introduced using techniques well known in the art. The modifications also can be carried out, for example, by site-specific in vitro mutagenesis or by PCR or by any other genetic engineering methods known in art which are suitable for specifically changing a nucleic acid sequence. In vitro mutagenesis protocols are described, for example, in *In Vitro Mutagenesis Protocols*, Braman, ed., 2002, Humana Press, and in Sankaranarayanan, *Protocols in Mutagenesis*, 2001, Elsevier Science Ltd.

High level expressing improved IL-12 sequences can be constructed by altering select codons throughout a native IL-12 nucleic acid sequence, or by altering codons at the 5'-end, the 3'-end, or within a middle subsequence. It is not necessary that every codon be altered, but that a sufficient number of codons are altered so that the expression (i.e., transcription and/or translation) of the improved IL-12 nucleic acid sequence is at least about 10%, 20%, 30%, 40%, 50%, 60%, 70%, 80%, 90%, 1-fold, 2-fold, 3-fold, 4-fold, 5-fold, 6-fold, or more abundant in comparison to expression from a native IL-12 nucleic acid sequence under the same conditions. Expression can be detected over time or at a designated endpoint, using techniques known to those in the art, for example, using gel electrophoresis or anti-IL-12 antibodies in solution phase or solid phase binding reactions (e.g., ELISA, immunohistochemistry). Interleukin-12 ELISA kits for detecting either the p35 or p40 subunits polypeptides, or the p70 heterodimer, are commercially available from, for example, R & D Systems (Minneapolis, Minn.), and Pepro-Tech, Rocky Hill, N.J.

Figure 6:
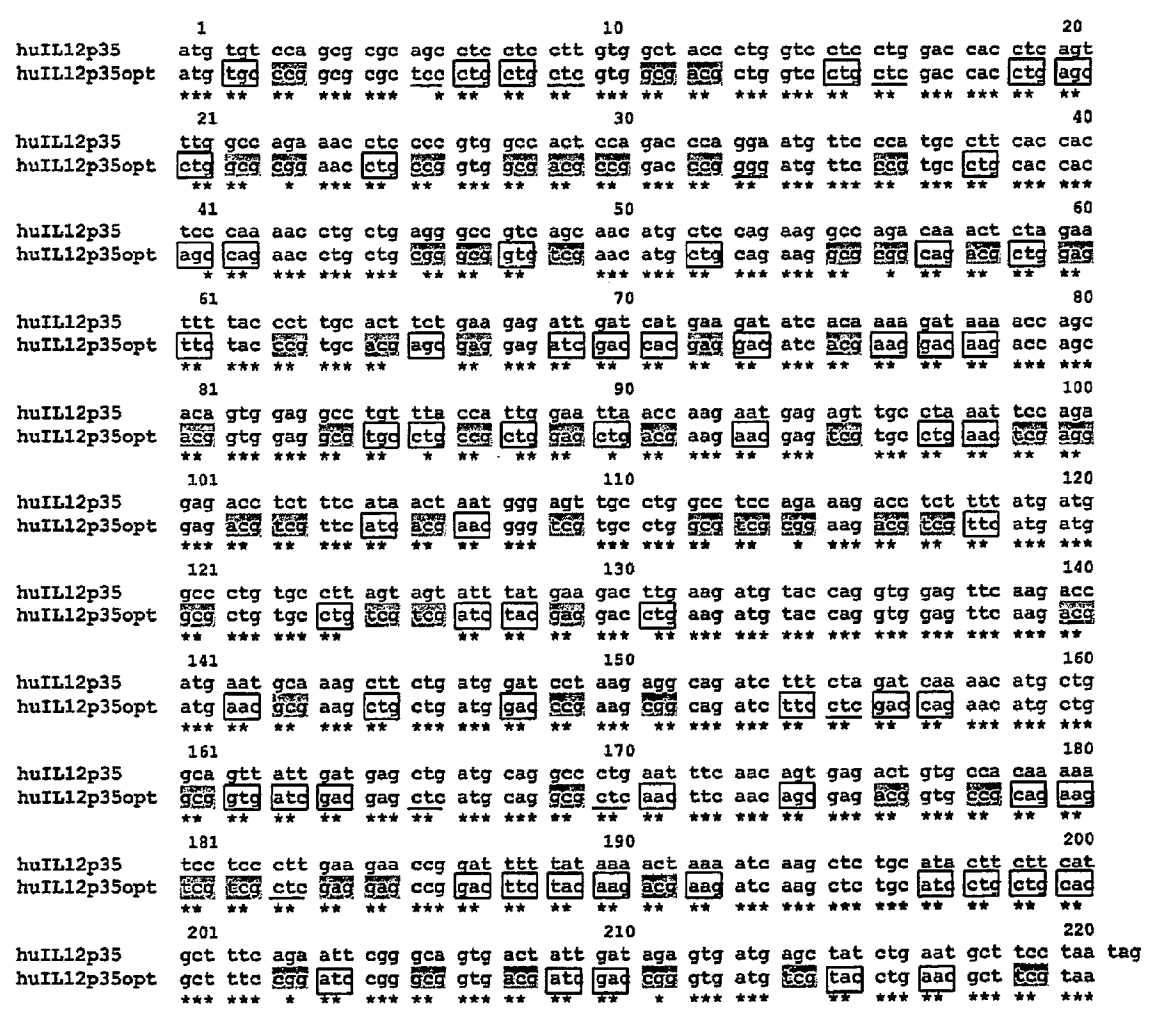
Figure 8:
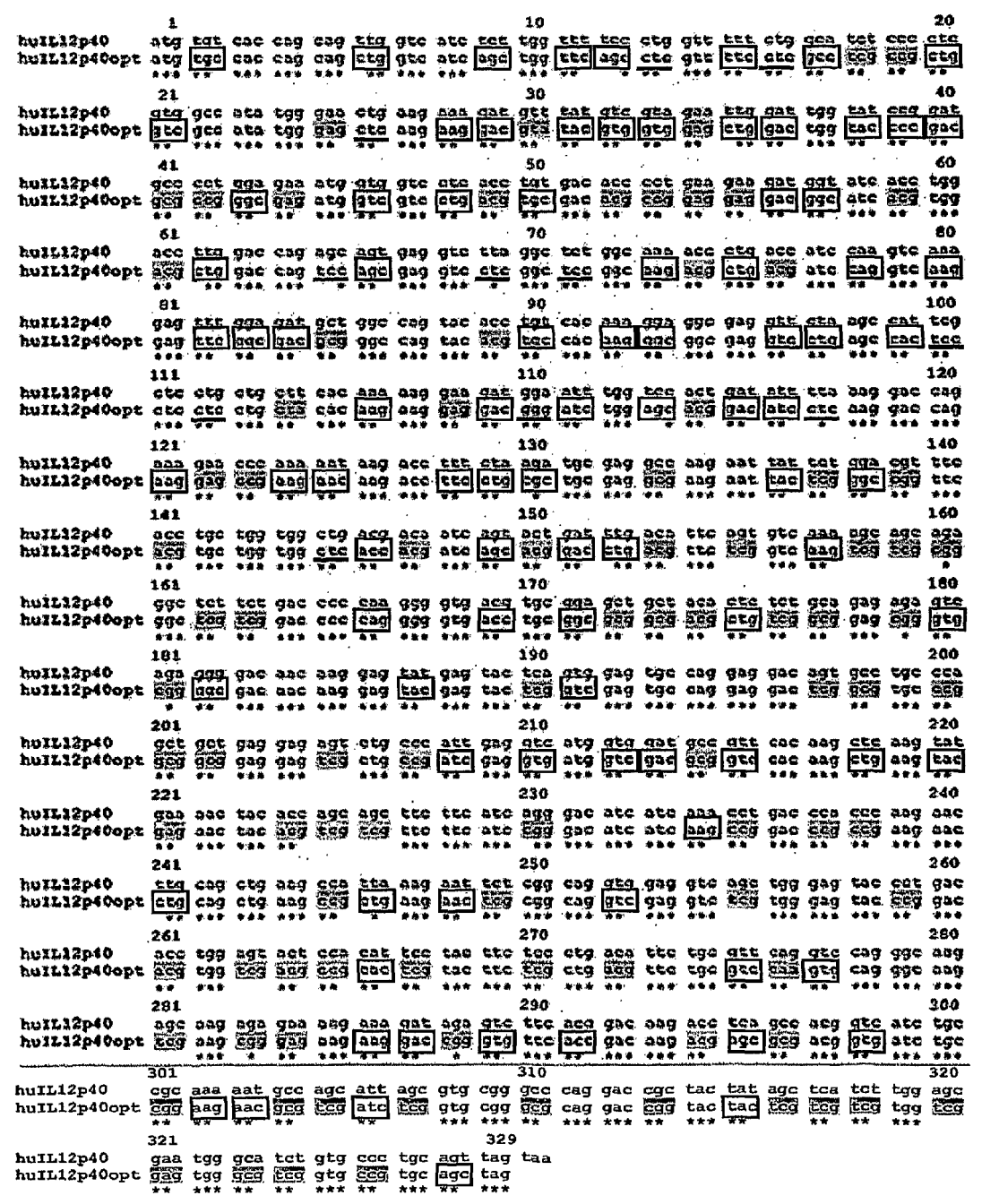

Usually at least about 50% of the changed codons identified in FIG. 6 for IL-12p35 and in FIG. 8 for IL-12p40 are changed to another codon encoding the same or a similar amino acid residue. In other embodiments, at least about 60%, 65%, 70%, 75%, 80%, 85%, 90%, 95%, 95%, 97%, 98%, 99% of the changed codons identified in FIG. 6 for IL-12p35 and in FIG. 8 for IL-12p40 are changed to another codon encoding the same or a similar amino acid residue.

The codon positions that can be changed for an improved IL-12 p35 nucleic acid sequence as identified in FIG. 6 are 2 (e.g., tgt, tgc), 3 (e.g., cca, ccg, ccc, cct), 6 (e.g., agc, agt, tcc, tca, tcg, tct), 7 (e.g., ctc, ctg, cta, ctc, tta, ttg), 8 (e.g., ctc, ctg, cta, ctc, tta, ttg), 9 (e.g., ctt, ctc, cta, ctg, tta, ttg), 11 (e.g., gct, gcg, gca, gcc), 12 (e.g., acc, acg, aca, act), 15 (e.g., ctc, ctg, cta, ctt, tta, ttg), 16 (e.g., ctg, ctc, cta, ctt, tta, ttg), 19 (e.g., ctc, ctg, cta, ctt, tta, ttg), 20 (e.g., agt, agc), 21 (e.g., ttg, ctg, tta, cta, ctc, ctt), 22 (e.g., gcc, gcg, gca, gct), 23 (e.g., aga, cgg, agg, cga, cgc, cgt), 25 (e.g., ctc, ctg, cta, ctt, tta, ttg), 26 (e.g., ccc, ccg, cca, cct), 28 (e.g., gcc, gcg, gca, gct), 29 (e.g., act, acg, aca, act), 30 (e.g., cca, ccg, ccc, cct), 32 (e.g., cca, ccg, ccc, cct), 33 (e.g., gga, ggg, ggc, ggt), 36 (e.g., cca, ccg, ccc, cct), 38 (e.g., ctt, ctg, cta, ctc, tta, ttg), 41 (e.g., tcc, agc, tca, tcg, tct, agt), 42 (e.g., caa, cag), 46 (e.g., agg, cgg, aga, cga, cgc, cgt), 47 (e.g., gcc, gcg, gca, gct), 48 (e.g., gtc, gtg, gta, gtt), 49 (e.g., agc, tcg, agt, tca, tcc, tct), 52 (e.g., ctc, ctg, cta, ctt, tta, ttg), 55 (e.g., gcc, gcg, gca, gct), 56 (e.g., aga, cgg, agg, cga, cgc, cgt), 57 (e.g., caa, cag), 58 (e.g., act, acg, aca, acc), 59 (e.g., cta, ctg, ctc, ctt, tta, ttg), 60 (e.g., gaa, gag), 61 (e.g., ttt, ttc), 63 (e.g., cct, ccg, cca, ccc), 65 (e.g., act, acg, aca, acc), 66 (e.g., tct, agc, tca, tcg, tcc, agt), 67 (e.g., gaa, gag), 69 (e.g., att, atc, ata), 70 (e.g., gat, gac), 71 (e.g., cat, cac), 72 (e.g., gaa, gag), 73 (e.g., gat, gac), 75 (e.g., aca, acg, acc, act), 76 (e.g., aaa, aag), 77 (e.g., gat, gac), 78 (e.g., aaa, aag), 81 (e.g., aca, acg, acc, act), 84 (e.g. gcc, gcg, gca, gct), 85 (e.g., tgt, tgc), 86 (e.g., tta, ctg, ttg, cta, ctc, ctt), 87 (e.g., cca, ccg, ccc, cct), 88 (e.g., ttg, ctg, tta, cta, ctc, ctt), 89 (e.g., gaa, gag), 90 (e.g., tta, ctg, ttg, cta, ctc, ctt), 91 (e.g., acc, acg, aca, act), 93 (e.g., aat, aac), 95 (e.g., agt, tcg, agc, tca, tcc, tct), 97 (e.g., cta, ctg, ctc, ctt, tta, ttg), 98 (e.g., aat, aac), 99 (e.g., tcc, tcg, tca, tct, agt, agc), 100 (e.g., aga, agg, cga, cgg, cgc, cgt), 102 (e.g., acc, acg, aca, act), 103 (e.g., tct, tcg, tca, tcc, agt, agc), 105 (e.g., ata, atc, att), 106 (e.g., act, acg, aca, acc), 107 (e.g., aat, aac), 109 (e.g., agt, tcg, agc, tca, tcc, tct), 112 (e.g., gcc, gcg, gca, gct), 113 (e.g., tcc, tcg, tca, tct, agc, agt), 114 (e.g., aga, cgg, agg, cga, cgc, cgt), 116 (e.g., acc, acg, aca, act), 117 (e.g., tct, tcg, tca, tcc, agc, agt), 18 (e.g., ttt, ttc), 121 (e.g., gcc, gcg, gca, gct), 124 (e.g., ctt, ctg, cta, ctc, tta, ttg), 125 (e.g., agt, tcg, agc, tca, tcc, tct), 126 (e.g., agt, tcg, agc, tca, tcc, tct), 127 (e.g., att, atc, ata), 128 (e.g., tat, tac), 129 (e.g., gaa, gag), 131ttg, ctg, tta, cta, ctc, ctt), 140 (e.g., acc, acg, aca, act), 142 (e.g., aat, aac), 143 (e.g., gca, gcg, gcc, gct), 145 (e.g., ctt, ctg, cta, ctc, tta, ttg), 148 (e.g., gat, gac), 149 (e.g., cct, ccg, cca, ccc), 151 (e.g., agg, cgg, aga, cga, cgc, cgt), 154 (e.g., ttt, ttc), 155 (e.g., cta, ctc, ctg, ctt, tta, ttg), 156 (e.g., gat, gac), 157 (e.g., caa, cag), 161 (e.g. gca, gcg, gcc, gct), 162 (e.g., gtt, gtg, gta, gtc), 163 (e.g., att, atc, ata), 164 (e.g., gat, gac), 166 (e.g., ctg, ctc, cta, ctt, tta, ttg), 169 (e.g., gcc, gcg, gca, gct), 170 (e.g., ctg, ctc, cta, ctt, tta, ttg), 171 (e.g., aat, aac), 174 (e.g., agt, agc, tca, tcg, tcc, tct), 176 (e.g., act, acg, aca, acc), 178 (e.g., cca, ccg, ccc, cct), 179 (e.g., caa, cag), 180 (e.g., aaa, aag), 181 (e.g., tcc, tcg, tca, tct, agt, agc), 182 (e.g., tcc, tcg, tca, tct, agc, agt), 183 (e.g., ctt, ctc, cta, ctg, tta, ttg), 184 (e.g., gaa, gag), 185 (e.g., gaa, gag), 187 (e.g., gat, gac), 188 (e.g., ttt, ttc), 189 (e.g., tat, tac), 190 (e.g., aaa, aag), 191 (e.g., act, acg, aca, acc), 192 (e.g., aaa, aag), 197 (e.g., ata, atc, att), 198 (e.g., ctt, ctg, cta, ctc, tta, ttg), 199 (e.g., ctt, ctg, cta, ctc, tta, ttg), 200 (e.g., cat, cac), 203 (e.g., aga, cgg, agg, cga, cgc, cgt), 204 (e.g., att, atc, ata), 206 (e.g., gca, gcg, gcc, gct), 208 (e.g., act, acg, aca, acc), 209 (e.g., att, atc, ata), 210 (e.g., gat, gac), 211 (e.g., aga, cgg, agg, cga, cgc, cgt), 214 (e.g., agc, tcg, agt, tca, tcc, tct), 215 (e.g., tat, tac), 217 (e.g., aat, aac) and 219 (e.g., tcc, tcg, tca, tct, agc, agt).

The codon positions that can be changed for an improved IL-12 p40 nucleic acid sequence as identified in FIG. 8 are 2 (e.g., tgt, tgc), 6 (e.g., ttg, ctg, tta, cta, ctc, ctt), 9 (e.g., tct, agc, tca, tcg, tcc, agt), 11 (e.g., ttt, ttc), 12 (e.g., tcc, agc, tca, tcg, tct, agt), 13 (e.g., ctg, ctc, cta, ctt, tta, ttg), 15 (e.g., ttt, ttc), 16 (e.g., ctg, ctc, cta, ctt, tta, ttg), 17 (e.g., gca, gcc, gcg, gct), 18 (e.g., tct, tcg, tca, tcc, agc, agt), 19 (e.g., ccc, ccg, cca, cct), 20 (e.g., ctc, ctg, cta, ctt, tta, ttg), 21 (e.g., gtg, gtc, gta, gtt), 25 (e.g., gaa, gag), 26 (e.g., ctg, ctc, cta, ctt, tta, ttg), 28 (e.g., aaa, aag), 29 (e.g., gat, gac), 30 (e.g., gtt, gta, gtg, gtc), 31 (e.g., tat, tac), 32 (e.g., gtc, gtg, gta, gtt), 33 (e.g., gta, gtg, gtc, gtt), 34 (e.g., gaa, gag), 35 (e.g., ttg, ctg, tta, cta, ctc, ctt), 36 (e.g., gat, gac), 38 (e.g., tat, tac), 39 (e.g., ccg, ccc, cca, cct), 40 (e.g., gat, gac), 41 (e.g., gcc, gcg, gca, gct), 42 (e.g., cct, ccg, cca, ccc), 43 (e.g., gga, ggc, ggg, ggt), 44 (e.g., gaa, gag), 46 (e.g., gtg, gtc, gta, gtt), 48 (e.g., ctc, ctg, cta, ctt, tta, ttg), 49 (e.g., acc, acg, aca, act), 50 (e.g., tgt, tgc), 52 (e.g., acc, acg, aca, act), 53 (e.g., cct, ccg, cca, cc), 54 (e.g., gaa, gag), 55 (e.g., gaa, gag), 56 (e.g., gat, gac), 57 (e.g., ggt, ggc, gga, ggg), 59 (e.g., acc, acg, aca, act), 61 (e.g., acc, acg, aca, act), 62 (e.g., ttg, ctg, tta, cta, ctc, ctt), 65 (e.g., agc, tcc, agt, tca, tcg, tct), 66 (e.g., agt, agc, tca, tcg, tcc, tct), 69 (e.g., tta, ctc, ttg, cta, ctg, ctt), 71 (e.g., tct, tcc, tca, tcg, agc, agt, 73 (e.g., aaa, aag), 74 (e.g., acc, acg, aca, act), 75 (e.g., ctg, cta, ctc, ctt, tta, ttg), 76 (e.g., acc, acg, aca, act), 78 (e.g., caa, cag), 80 (e.g., aaa, aag), 82 (e.g., ttt, ttc), 83 (e.g., gga, ggc, ggg, ggt), 84 (e.g., gat, gac), 85 (e.g., gct, gcg, gca, gcc), 89 (e.g., acc, acg, aca, act), 90 (e.g., tgt, tgc), 92 (e.g., aaa, aag), 93 (e.g., gga, ggc, ggg, ggt), 96 (e.g., gtt, gtc, gta, gtg), 97 (e.g., cta, ctg, ctc, ctt, tta, ttg), 99 (e.g., cat, cac), 100 (e.g., tcg, tcc, tca, tct, agc, agt), 102 (e.g., ctg, ctc, cta, ctt, tta, ttg), 104 (e.g., ctt, cta, ctg, ctc, tta, ttg), 106 (e.g., aaa, aag), 108 (e.g., gaa, gag), 109 (e.g., gat, gac), 110 (e.g., gga, ggg, ggc, ggt), 111 (e.g., att, atc, ata), 113 (e.g., tcc, agc, tca, tcg, tct, agt), 114 (e.g., act, acg, aca, acc), 115 (e.g., gat, gac), 116 (e.g. att, atc, ata), 117 (e.g., tta, ctc, ttg, cta, ctg, ctt), 121 (e.g., aaa, aag), 122 (e.g., gaa, gag), 123 (e.g., ccc, ccg, cca, cct), 124 (e.g., aaa, aag), 125 (e.g., aat, aac), 128 (e.g., ttt, ttc), 129 (e.g., cta, ctg, ctc, ctt, tta, ttg), 130 (e.g., aga, cgc, agg, cga, cgg, cgt), 133 (e.g., gcc, gcg, gca, gct), 136 (e.g., tat, tac), 137 (e.g., tct, tcg, tca, tcc, agc, agt), 138 (e.g., gga, ggc, ggg, ggt), 139 (e.g., cgt, cgg, cga, cgc, aga, agg), 141 (e.g., acc, acg, aca, act), 145 (e.g., ctg, ctc, cta, ctt, tta, ttg), 146 (e.g., acg, acc, aca, act), 147 (e.g., aca, acg, acc, act), 149 (e.g., agt, agc, tca, tcg, tcc, tct), 150 (e.g., act, acg, aca, acc), 151 (e.g., gat, gac), 152 (e.g., ttg, ctg, tta, cta, ctc, ctt), 153 (e.g., aca, acg, acc, act), 155 (e.g., agt, tcg, agc, tca, tcc, tct), 157 (e.g., aaa, aag), 158 (e.g., agc, tcg, agt, tca, tcc, tct), 159 (e.g., agc, tcg, agt, tea, tcc, tct), 160 (e.g., aga, cgg, agg, cga, cgc, cgt), 162 (e.g., tct, tcg, tca, tcc, agc, agt), 163 (e.g., tct, tcg, tea, tcc, agc, agt), 166 (e.g., caa, cag), 169 (e.g., acg, acc, aca, act), 171 (e.g., gga, ggc, ggg, ggt), 172 (e.g., gct, gcg, gca, gcc), 173 (e.g., gct, gcg, gca, gcc), 174 (e.g., aca, acg, acc, act), 175 (e.g., ctc, ctg, cta, ctt, tta, ttg), 176 (e.g., tct, tcg, tca, tcc, agc, agt), 177 (e.g., gca, gcg, gcc, gct), 179 (e.g., aga, cgg, agg, cga, cgc, cgt), 180 (e.g., gtc, gtg, gta, gtt), 181 (e.g., aga, cgg, agg, cga, cgc, cgt), 182 (e.g., ggg, ggc, gga, ggt), 187 (e.g., tat, tac), 190 (e.g., tca, tcg, tcc, tct, agc, agt), 191 (e.g., gtg, gtc, gta, gtt), 197 (e.g., agt, tcg, agc, tca, tcc, tct), 198 (e.g., gcc, gcg, gca, gct), 200 (e.g., cca, ccg, ccc, cct), 201 (e.g., gct, gcg, gca, gcc), 202 (e.g., gct, gcg, gca, gcc), 205 (e.g., agt, tcg, agc, tca, tcc, tct), 207 (e.g., ccc, ccg, cca, cct), 208 (e.g., att, atc, ata), 210 (e.g., gtc, gtg, gta, gtt), 212 (e.g., gtg, gtc, gta, gtt), 213 (e.g., gat, gac), 214 (e.g., gcc, gcg, gca, gtt), 215 (e.g., gtt, gtc, gta, gtg), 218 (e.g., ctc, ctg, cta, ctt, tta, ttg), 220 (e.g., tat, tac), 221 (e.g., gaa, gag), 224 (e.g., acc, acg, aca, act), 225 (e.g., agc, tcg, agt, tca, tcc, tct), 226 (e.g., agc, tcg, agt, tca, tcc, tct), 230 (e.g., agg, cgg, aga, cga, cgc, cgt), 234 (e.g., aaa, aag), 235 (e.g., cct, ccg, cca, ccc), 237 (e.g., cca, ccg, ccc, cct), 238 (e.g., ccc, ccg, cca, cct), 241 (e.g., ttg, ctg, tta, cta, ctc, ctt), 245 (e.g., cca, ccg, ccc, cct), 246 (e.g., tta, ctg, ttg, cta, ctc, ctt), 248 (e.g. aat, aac), 249 (e.g., tct, tcg, tca, tcc, agc, agt), 252 (e.g., gtg, gtc, gta, gtt), 255 (e.g., agc, tcg, agt, tca, tcc, tct), 259 (e.g., cct, ccg, cca, ccc), 261 (e.g., acc, acg, aca, act), 263 (e.g., agt, tcg, agc, tca, tcc, tct), 264 (e.g., act, acg, aca, acc), 265 (e.g., cca, ccg, ccc, cct), 266 (e.g., cat, cac), 267 (e.g., tcc, tcg, tca, tct, agc, agt), 270 (e.g., tcc, tcg, tca, tct, agc, agt), 272 (e.g., aca, acg, acc, act), 275 (e.g., gtt, gtc, gta, gtg), 276 (e.g., cag, caa), 277 (e.g., gtc, gtg, gta, gtt), 281 (e.g., agc, tcg, agt, tca, tcc, tct), 283 (e.g., aga, cgg, agg, cga, cgc, cgt), 284 (e.g., gaa, gag), 286 (e.g., aaa, aag), 287 (e.g., gat, gac), 288 (e.g., aga, cgg, agg, cga, cgc, cgt), 289 (e.g., gtc, gtg, gta, gtt), 291 (e.g., acg, acc, aca, act), 294 (e.g., acc, acg, aca, act), 295 (e.g., tca, agc, tcg, tcc, tct, agt), 296 (e.g., gcc, gcg, gca, gct), 298 (e.g., gtc, gtg, gta, gtt), 301 (e.g., cgc, cgg, cga, cgt, aga, agg), 302 (e.g., aaa, aag), 303 (e.g., aat, aac), 304 (e.g., gcc, gcg, gca, gct), 305 (e.g., agc, tcg, agt, tca, tcc, tct), 306 (e.g., att, atc, ata), 307 (e.g., agc, tcg, agt, tca, tcc, tct), 310 (e.g., gcc, gcg, gca, gct), 313 (e.g., cgc, cgg, cga, cgt, aga, agg), 315 (e.g., tat, tac), 316 (e.g., agc, tcg, agt, tca, tcc, tct), 317 (e.g., tca, tcg, tcc, tct, agc, agt), 318 (e.g., tct, tcg, tca, tcc, agc, agt), 320 (e.g., agc, tog, agt, tca, tcc, tct), 321 (e.g., gaa, gag), 323 (e.g., gca, gcg, gcc, gct), 324 (e.g., tct, tcg, tca, tcc, agc, agt), 326 (e.g., ccc, ccg, cca, cct) and 328 (e.g., agt, agc, tca, tcg, tcc, tct).

The GC-content of an improved IL-12 nucleic acid sequence is usually increased in comparison to a native IL-12 nucleic acid sequence when applying the present methods. For example, the GC-content of an improved IL-12p35 nucleic acid sequence can be at least about 50%, 51%, 52%, 53%, 54%, 55%, 56%, 57%, 58%, 59%, 60%, 61%, 62%, 63%, 64%, 65% or more. The GC-content of an improved IL-12p40 nucleic acid sequence can be at least about 55%, 56%, 57%, 58%, 59%, 60%, 61%, 62%, 63%, 64%, 65%, 66%, 67%, 68%, 69%, 70% or more.

Once a high level expressing improved IL-12 nucleic acid sequence has been constructed, it can be cloned into a cloning vector, for example a TA-cloning® vector (Invitrogen, Carlsbad, Calif.) before subjecting to further manipulations for insertion into one or more expression vectors. Manipulations of improved IL-12 nucleic acid sequences, including recombinant modifications and purification, can be carried out using procedures well known in the art. Such procedures have been published, for example, in Sambrook and Russell, *Molecular Cloning: A Laboratory Manual*, 2000, Cold Spring Harbor Laboratory Press and *Current Protocols in Molecular Biology*, Ausubel, et al., eds., 1987-2005, John Wiley & Sons.

3. Expression Vectors

Figure 2:
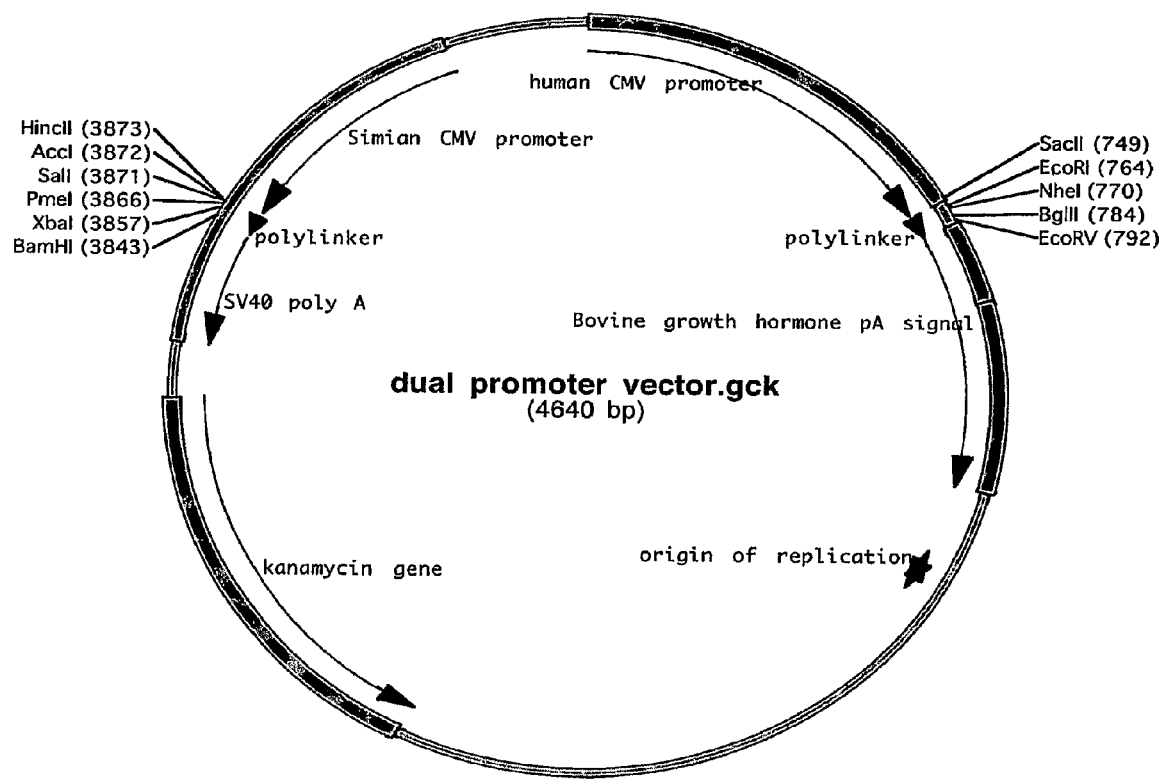
FIG. 2 illustrates a schematic of a dual promoter expression vector for expression of an IL-12 heterodimer. SiCMV and hCMV promoters are exemplified, but other promoters known in the art can be used. Bovine growth hormone (BGH) and SV40 polyadenylation sequences are exemplified, but other polyadenylation signals known in the art can be used.
Figure 3:
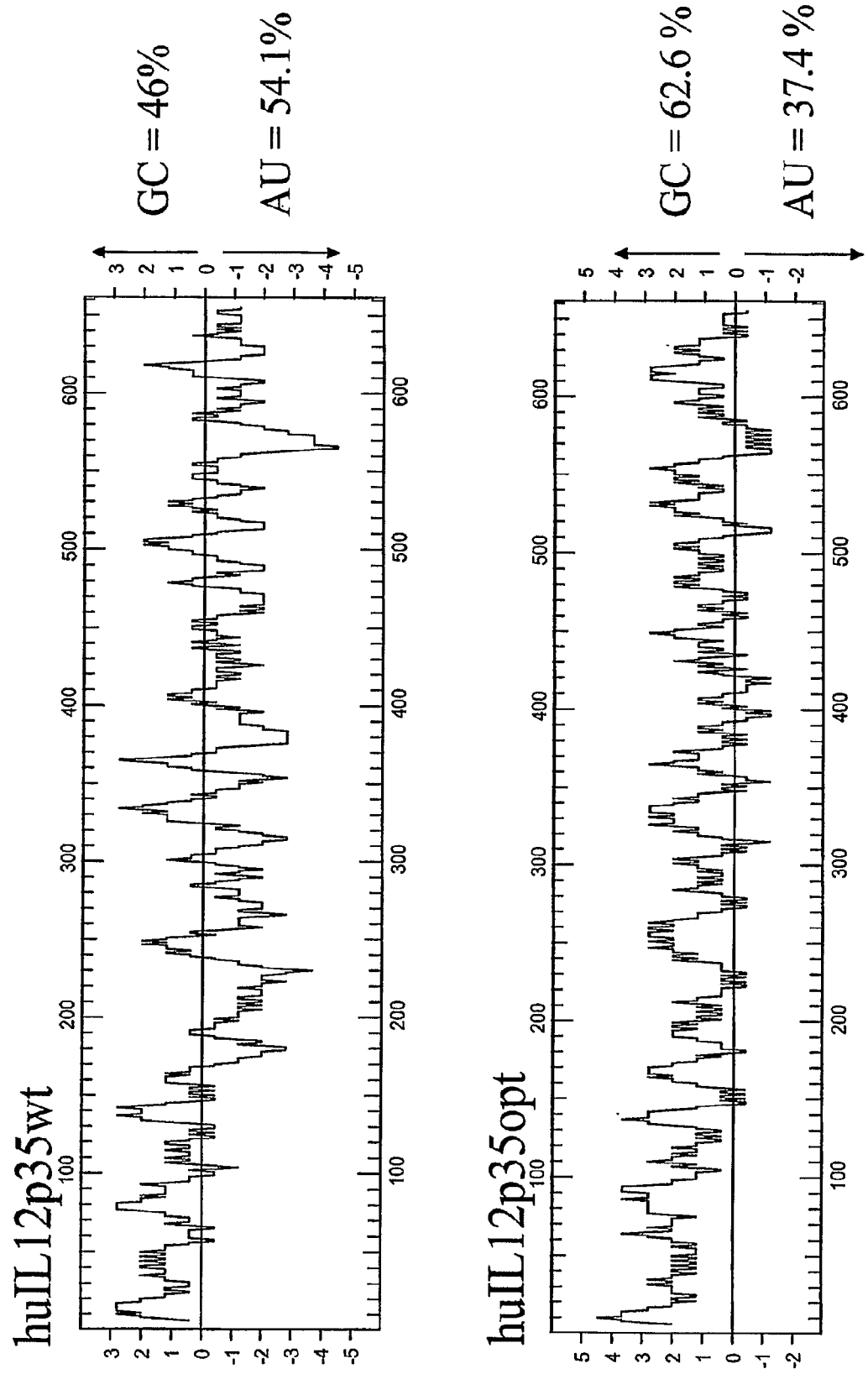
FIG. 3 illustrates increased GC content (i.e., percentage of (deoxy)guanosine and (deoxy)cytidine (deoxy)ribonucleosides) in human improved IL-12p35 (hIL-12p35-opt, bottom), as compared to human wild-type IL-12p35 (top).
Figure 4:
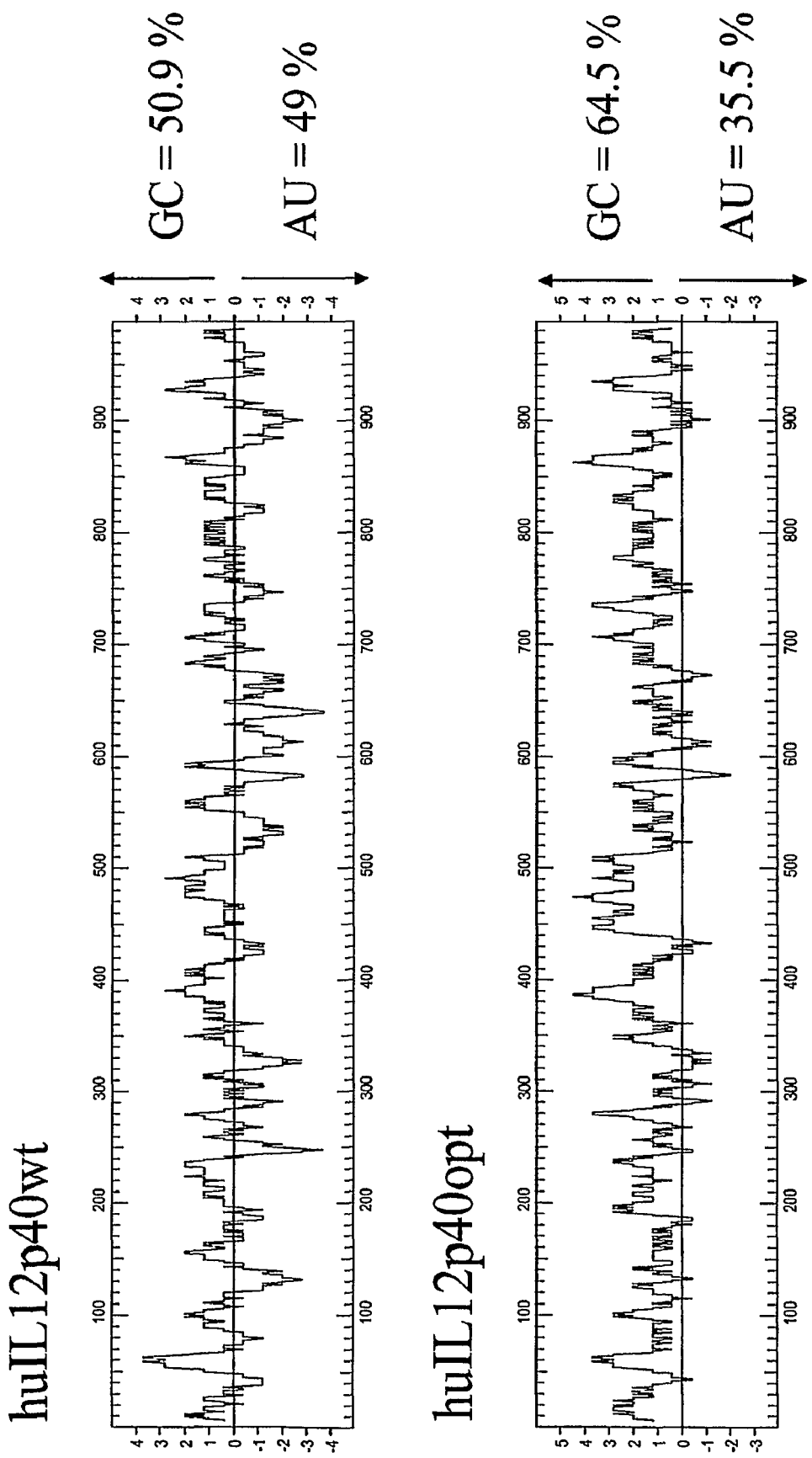
FIG. 4 illustrates increased GC content in human improved IL-12p40 (hIL-12p40-opt, bottom) as compared to human wild-type IL-12p40 (top).
Figure 9:
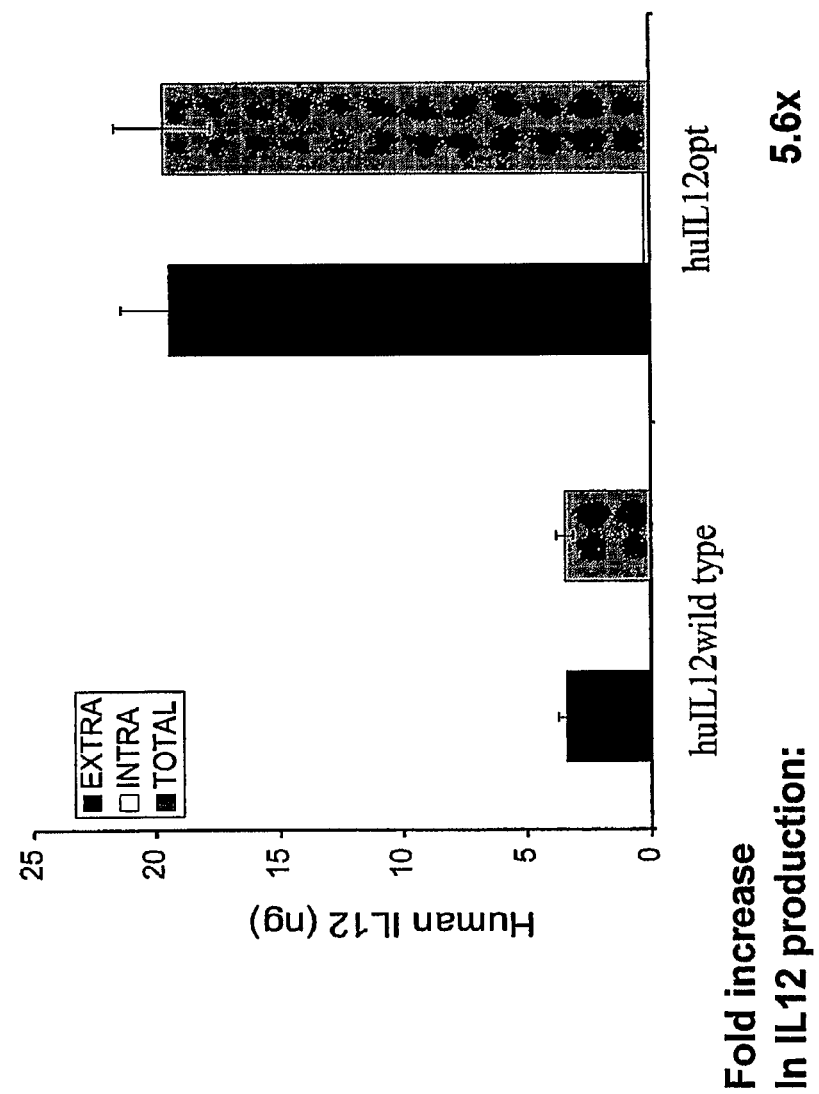
FIG. 9 illustrates an increase in human IL-12 heterodimer production from human RD (human muscle derived cell line) cells transfected with 100 ng of a plasmid having improved human IL-12p35 and human IL-12p40 coding sequences. Extracellular, intracellular, and total human IL-12 protein production was determined using a commercially available kit. Using the present methods, a 5.6 fold increase in IL-12 production was achieved using an improved IL-12 coding sequence in comparison to a wild-type IL-12 coding sequence.
Figure 12:
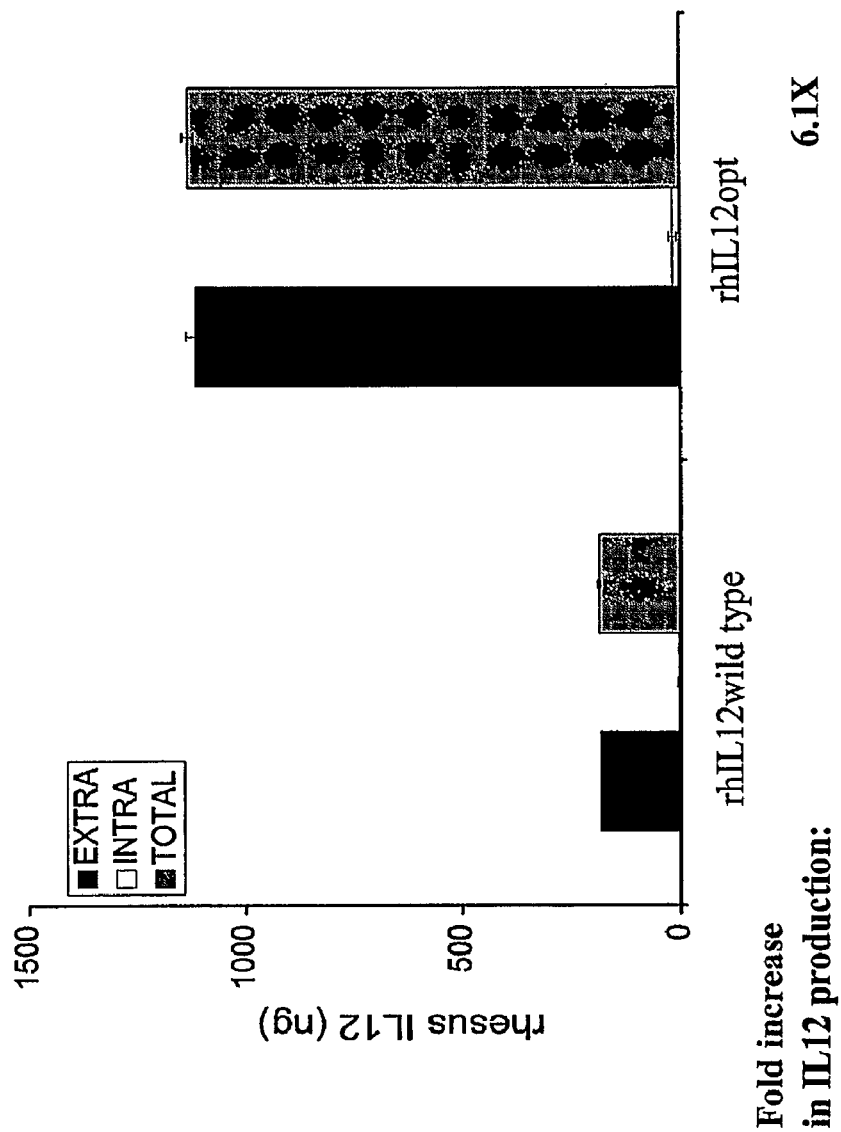
FIG. 12 illustrates an increase in Rhesus monkey IL-12 heterodimer production from human RD cells transfected with 1 microgram of a plasmid having improved Rhesus monkey IL-12p35 and Rhesus monkey IL-12p40 coding sequences. Extracellular, intracellular, and total rhesus IL12 protein production was determined using a commercially available kit. Using the present methods, a 6.1 fold increase in IL-12 production was achieved using an improved IL-12 coding sequence in comparison to a wild-type IL-12 coding sequence.

Both IL-12 subunit chains can be recombinantly expressed from a single plasmid or expression vector (see, FIG. 2). The p35 and p40 subunit chains can be expressed from a single expression cassette or independent expression cassettes. The expression vectors of the invention typically have at least two independent expression cassettes, one that will express a IL-12p35 subunit and one that will express a IL-12p40 subunit. Within each expression cassette, sequences encoding one or both IL-12 subunit chains will be operably linked to expression regulating sequences. "Operably linked" sequences include both expression control sequences that are contiguous with the nucleic acid of interest and expression control sequences that act in trans or at a distance to control the gene of interest. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., Kozak consensus sequence); sequences that enhance protein stability; and when desired, sequences that enhance protein secretion. The regulating sequences independently can be the same or different between the two expression cassettes. Usually, the regulating sequences will be different. When expressing the IL-12 subunit chains from a single expression cassette, an internal ribosome entry site (IRES) is included.

The expression vector can optionally also have a third independent expression vector for expressing a selectable marker. Selectable markers are well known in the art, and can include, for example, proteins that confer resistance to an antibiotics, fluorescent proteins, antibody epitopes, etc. Exemplified markers that confer antibiotic resistance include sequences encoding β-lactamases (against P-lactams including penicillin, ampicillin, carbenicillin), or sequences encoding resistance to tetracylines, aminoglycosides (e.g., kanamycin, neomycin), etc. Exemplified fluorescent proteins include green fluorescent protein, yellow fluorescent protein and red fluorescent protein.

The promoter(s) included in the expression cassette(s) should promote expression of one or both of the IL-12 subunit chains in a mammalian cell. The promoter or promoters can be viral, oncoviral or native mammalian, constitutive or inducible, or can preferentially regulate transcription of one or both IL-12 subunit chains in a particular tissue type or cell type (e.g., "tissue-specific").

A "constitutive" promoter is a promoter that is active under most environmental and developmental conditions. Exemplified constitutive promoters in mammalian cells include oncoviral promoters (e.g., simian cytomegalovirus (CMV), human CMV, simian virus 40 (SV40), rous sarcoma virus (RSV)), promoters for immunoglobulin elements (e.g., IgH), promoters for "housekeeping" genes (e.g., β-actin, dihydrofolate reductase).

In another embodiment, inducible promoters may be desired. An "inducible" promoter is a promoter that is active under environmental or developmental regulation. Inducible promoters are those which are regulated by exogenously supplied compounds, including without limitation, a zinc-inducible metallothionine (MT) promoter; an isopropyl thiogalactose (IPTG)-inducible promoter, a dexamethasone (Dex)-inducible mouse mammary tumor virus (MMTV) promoter; a tetracycline-repressible system (Gossen et al, *Proc. Natl. Acad. Sci. USA*, 89: 5547-5551 (1992)); the tetracycline-inducible system (Gossen et al., *Science*, 268: 1766-1769 (1995); see also Harvey et al., *Curr. Opin. Chem. Biol.*, 2: 512-518 (1998)); the RU486-inducible system (Wang et al., *Nat. Biotech.*, 15: 239-243 (1997) and Wang et al., *Gene Ther.*, 4: 432-441 (1997)); and the rapamycin-inducible system (Magari et al. *J. Clin. Invest.*, 100: 2865-2872 (1997)). Other types of inducible promoters which can be useful in this context are those which are regulated by a specific physiological state, e.g., temperature, acute phase, or in replicating cells only.

In another embodiment, the native promoter for a mammalian IL-12 can be used. The native promoter may be preferred when it is desired that expression of improved IL-12 sequences should mimic the native expression. The native promoter can be used when expression of the improved IL-12 must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic expression of native IL-12.

In another embodiment, the improved IL-12 sequences can be operably linked to a tissue-specific promoter. For instance, if expression in lymphocytes or monocytes is desired, a promoter active in lymphocytes or monocytes, respectively, should be used. Examples of promoters that are tissue-specific are known for numerous tissues, including liver (albumin, Miyatake et al. *J. Virol.*, 71: 5124-32 (1997); hepatitis B virus core promoter, Sandig et al., *Gene Ther.*, 3: 1002-9 (1996); alpha-fetoprotein (AFP), Arbuthnot et al. *Hum. Gene Ther.* 7: 1503-14 (1996)), bone (osteocalcin, Stein et al., *Mol. Biol. Rep.*, 24: 185-96 (1997); bone sialoprotein, Chen et al., *J. Bone Miner. Res.*, 11: 654-64 (1996)), lymphocytes (CD2, Hansal et al., *J. Immunol.*, 161: 1063-8 (1998); immunoglobulin heavy chain; T cell receptor a chain), neuronal (neuron-specific enolase (NSE) promoter, Andersen et al. *Cell. Mol. Neurobiol.*, 13: 503-15 (1993); neurofilament light-chain gene, Piccioli et al., *Proc. Natl. Acad. Sci. USA*, 88: 5611-5 (1991); the neuron-specific vgf gene, Piccioli et al., *Neuron*, 15: 373-84 (1995)); among others.

Dual-promoter expression vectors for the concurrent expression of two polypeptide chains in a mammalian cell are commercially available, for example, the pVITRO vector from InvivoGen (San Diego, Calif.). An exemplified dual-promoter expression vector is shown in FIGS. 2, 17 and 18.

4. Mammalian Cells

The expression vectors of the invention can be expressed in mammalian host cells. The host cells can be in vivo in a host or in vitro. For example, expression vectors containing high-level expressing IL-12 nucleic acid sequences can be transfected into cultured mammalian host cells in vitro, or delivered to a mammalian host cell in a mammalian host in vivo.

Exemplary host cells that can be used to express improved IL-12 nucleic acid sequences include mammalian primary cells and established mammalian cell lines, including COS, CHO, HeLa, NIH3T3, HEK 293-T, RD and PC12 cells. Mammalian host cells for expression of IL-12 protein from high level expressing improved IL-12 nucleic acid sequences are commercially available from, for example, the American Type Tissue Collection (ATCC), Manassas, Va. Protocols for in vitro culture of mammalian cells is also well known in the art. See, for example, *Handbook of Industrial Cell Culture: Mammalian, Microbial, and Plant Cells*, Vinci, et al., eds., 2003, Humana Press; and *Mammalian Cell Culture: Essential Techniques*, Doyle and Griffiths, eds., 1997, John Wiley & Sons.

Protocols for transfecting mammalian host cells in vitro and expressing recombinant nucleic acid sequences are well known in the art. See, for example, Sambrook and Russell, and Ausubel, et al, supra; *Gene Delivery to Mammalian Cells: Nonviral Gene Transfer Techniques*, Methods in Molecular Biology series, Heiser, ed., 2003, Humana Press; and Makrides, *Gene Transfer and Expression in Mammalian Cells*, New Comprehensive Biochemistry series, 2003, Elsevier Science. Mammalian host cells modified to express the improved IL-12 nucleic acid sequences can be transiently or stably transfected with a recombinant vector. The improved IL-12 sequences can remain epigenetic or become chromosomally integrated.

5. Vaccine Adjuvants

The high level expression improved IL-12 nucleic acid sequences are suitable for use as an adjuvant co-delivered with a vaccine antigen. The use of IL-12 as an adjuvant in antimicrobial therapy, anticancer therapy and for stimulating mucosal immunity is known in the art. See, for example, Tomioka, *Curr Pharm Des* (2004) 10:3297; El-Aneed, *Eur J Pharmacol* (2004) 498:1; Stevceva and Ferrari, *Curr Pharm Des* (2005) 11:801; and Toka, et al., *Immunol Rev* (2004) 199:100).

In a preferred embodiment, high level expressing improved IL-12 nucleic acid sequences are co-administered with one or more vaccine antigens, with at least the improved IL-12 nucleic acid sequences delivered as naked DNA. The antigen can be delivered as one or more polypeptide antigens or a nucleic acid encoding one or more antigens. Naked DNA vaccines are generally known in the art; see, Wolff, et al., *Science* (1990) 247:1465; Brower, *Nature Biotechnology* (1998) 16:1304-130; and Wolff, et al., *Adv Genet* (2005) 54:3. Methods for the use of nucleic acids as DNA vaccines are well known to one of ordinary skill in the art. See, *DNA Vaccines*, Ertl, ed., 2003, Kluwer Academic Pub and *DNA Vaccines: Methods and Protocols*, Lowrie and Whalen, eds., 1999, Humana Press. The methods include placing a nucleic acid encoding one or more antigens under the control of a promoter for expression in a patient. Co-administering high level expressing improved IL-12 nucleic acid sequences further enhances the immune response against the one or more antigens. Without being bound by theory, following expression of the polypeptide encoded by the DNA vaccine, cytotoxic T-cells, helper T-cells and antibodies are induced which recognize and destroy or eliminate cells or pathogens expressing the antigen.

The invention contemplates compositions comprising improved IL-12 nucleic acid sequences in a physiologically acceptable carrier. While any suitable carrier known to those of ordinary skill in the art may be employed in the pharmaceutical compositions of this invention, the type of carrier will vary depending on the mode of administration. For parenteral administration, including subcutaneous or intramuscular injection, the carrier preferably comprises water, saline, and optionally an alcohol, a fat, a polymer, a wax, one or more stabilizing amino acids or a buffer. General formulation technologies are known to those of skill in the art (see, for example, *Remington: The Science and Practice of Pharmacy* (20th edition), Gennaro, ed., 2000, Lippincott Williams & Wilkins; *Injectable Dispersed Systems: Formulation, Processing And Performance*, Burgess, ed., 2005, CRC Press; and *Pharmaceutical Formulation Development of Peptides and Proteins*, Frkjr et al., eds., 2000, Taylor & Francis).

Naked DNA can be delivered in solution (e.g., a phosphate-buffered saline solution) by injection, usually by an intra-arterial, intravenous, subcutaneous or intramuscular route. In general, the dose of a naked nucleic acid composition is from about 10 µg to 10 mg for a typical 70 kilogram patient. Subcutaneous or intramuscular doses for naked nucleic acid (typically DNA encoding a fusion protein) will range from 0.1 mg to 50 mg for a 70 kg patient in generally good health.

DNA vaccinations can be administered once or multiple times. In some embodiments, the improved IL-12 nucleic acid sequences are administered more than once, for example, 2, 3, 4, 5, 6, 7, 8, 10, 15, 20 or more times as needed to induce the desired response (e.g., specific antigenic response). Multiple administrations can be administered, for example, bi-weekly, weekly, bi-monthly, monthly, or more or less often, as needed, for a time period sufficient to achieve the desired response.

In some embodiments, the improved IL-12 nucleic acid compositions are administered by liposome-based methods, electroporation or biolistic particle acceleration. A delivery apparatus (e.g., a "gene gun") for delivering DNA into cells in vivo can be used. Such an apparatus is commercially available (e.g., BioRad, Hercules, Calif., Chiron Vaccines, Emeryville, Calif.). Naked DNA can also be introduced into cells by complexing the DNA to a cation, such as polylysine, which is coupled to a ligand for a cell-surface receptor (see, for example, Wu, G. and Wu, C. H. (1988) *J. Biol. Chem.* 263: 14621; Wilson et al. (1992) *J. Biol. Chem.* 267:963-967; and U.S. Pat. Nos. 5,166,320; 6,846,809; 6,733,777; 6,720,001; 6,290,987). Liposome formulations for delivery of naked DNA to mammalian host cells are commercially available from, for example, Encapsula NanoSciences, Nashville, Tenn. An electroporation apparatus for use in delivery of naked DNA to mammalian host cells is commercially available from, for example, Inovio Biomedical Corporation, San Diego, Calif.

The improved IL-12 nucleic acid vaccine compositions are administered to a mammalian host. The mammalian host usually is a human or a primate. In some embodiments, the mammalian host can be a domestic animal, for example, canine, feline, lagomorpha, rodentia, rattus, hamster, murine. In other embodiment, the mammalian host is an agricultural animal, for example, bovine, ovine, porcine, equine, etc.

6. Methods of Expressing IL-12 in Mammalian Cells

The methods of the present invention provide for expressing IL-12 in a mammalian cell by introducing a recombinant vector into the cell to express the high level improved IL-12 p35 and p40 nucleic acid sequences described herein. The modified mammalian cell can be in vitro or in vivo in a mammalian host.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

The following examples are offered to illustrate, but not to limit the claimed invention.

Example 1

The strategy for introducing nucleotide changes into IL-12 sequences is to simultaneously rectify several factors affecting mRNA traffic, stability and expression. Codons are altered to change the overall mRNA AT(AU)-content or to remove any other inhibitory signals within the RNA such as all potential splice sites (computer programs predicting potential splice sites can be found for example at web sites such as fruitfly.org/seq_tools/splice.html, or sun1.softberry.com/berry.phtml) and also to alter sequences such as runs of A or T/U nucleotides, AATAAA, ATTTA and closely related variant sequences, known to negatively affect mRNA. By substituting codons with a different codon encoding the identical amino acid, the chosen codon can be more GC-rich, or can have a different sequence that is sufficient to alter the RNA structure. This approach has been described in several patents, each of which is hereby incorporated herein by reference in their entirety: U.S. Pat. Nos. 5,965,726; 5,972,596; 6,174,666; 6,291,664; 6,414,132; and 6,794,498.

Procedures

Standard lab techniques are used to generate, purify and sequence plasmid DNAs. One microgram (1 μg) of the plasmids containing the indicated IL-12 coding sequence were transfected into human 293 or RD cells seeded into 60 mm plates the day before with $10^6$ cells using calcium coprecipitation technique (293 cells) and the SuperFect Reagent protocol (Qiagen) for RD4 cells. 2-3 days later, intracellular and extracellular and total IL-12 protein was measured using commercial kits (R&D system). Due to the high homology of the human and Rhesus IL-12 proteins, their protein levels were determined by the same commercial ELISA kit. The results of different experiments are shown in FIGS. 9 and 12.

INFORMAL SEQUENCE LISTING

Human wild-type IL-12 p35 nucleic acid sequence
SEQ ID NO: 1

```
ATGTGTCCAGCGCGCAGCCTCCTCCTTGTGGCTACCCTGGTCCTCCTGGA

CCACCTCAGTTTGGCCAGAAACCTCCCCGTGGCCACTCCAGACCCAGGAA

TGTTCCCATGCCTTCACCACTCCCAAAACCTGCTGAGGGCCGTCAGCAAC

ATGCTCCAGAAGGCCAGACAAACTCTAGAATTTTACCCTTGCACTTCTGA

AGAGATTGATCATGAAGATATCACAAAAGATAAAACCAGCACAGTGGAGG

CCTGTTTACCATTGGAATTAACCAAGAATGAGAGTTGCCTAAATTCCAGA

GAGACCTCTTTCATAACTAATGGGAGTTGCCTGGCCTCCAGAAAGACCTC

TTTTATGATGGCCCTGTGCCTTAGTAGTATTTATGAAGACTTGAAGATGT

ACCAGGTGGAGTTCAAGACCATGAATGCAAAGCTTCTGATGGATCCTAAG

AGGCAGATCTTTCTAGATCAAAACATGCTGGCAGTTATTGATGAGCTGAT

GCAGGCCCTGAATTTCAACAGTGAGACTGTGCCACAAAAATCCTCGCCTT

GAAGAACCGGATTTTTATAAAACTAAAATCAAGCTCTGCATACTTCTTCA

TGCTTTCAGAATTCGGGCAGTGACTATTGATAGAGTGATGAGCTATCTGA

ATGCTTCCTAATAG
```

Human wild-type IL-12 p35 amino acid sequence
SEQ ID NO: 2

```
M C P A R S L L L V A T L V L L D H L S L A R N L

P V A T P D P G M F P C L H H S Q N L L R A V S N
```

-continued

```
M L Q K A R Q T L E F Y P C T S E E I D H E D I T

K D K T S T V E A C L P L E L T K N E S C L N S R

E T S F I T N G S C L A S R K T S F M M A L C L S

S I Y E D L K M Y Q V E F K T M N A K L L M D P K

R Q I F L D Q N M L A V I D E L M Q A L N F N S E

T V P Q K S S L E E P D F Y K T K I K L C I L L H

A F R I R A V T I D R V M S Y L N A S
```

Human improved IL-12 p35 nucleic acid sequence
SEQ ID NO: 3

```
ATGTGCCCGGCGCGCTCCCTGCTGCTCGTGGCGACGCTGGTCCTGCTCGA

CCACCTGAGCCTGGCGCGGAACCTGCCGGTGCCGACGCCGGACCCGGGGA

TGTTCCCGTGCCTGCACCACAGCCAGAACCTGCTGCGGGCGGTGTCGAAC

ATGCTGCAGAAGGCGCGGCAGACGCTGGAGTTCTACCCGTGCACGAGCGA

GGAGATCGACCACGAGGACATCACGAAGGACAAGACCAGCACGGTGGAGG

CGTGCCTGCCGCTGGAGCTGACGAAGAACGAGTCGTGCCTGAACTCGAGG

GAGACGTCGTTCATCACGAACGGGTCGTGCCTGGCGTCGCGGAAGACGTC

GTTCATGATGGCGCTGTGCCTGTCGTCGATCTACGAGGACCTGAAGATGT

ACCAGGTGGAGTTCAAGACGATGAACGCGAAGCTGCTGATGGACCCGAAG

CGGCAGATCTTCCTCGACCAGAACATGCTGGCGGTGATCGACGAGCTCAT

GCAGGCGCTCAACTTCAACAGCGAGACGGTGCCGCAGAAGTCGTCGCTCG

AGGAGCCGGACTTCTACAAGACGAAGATCAAGCTCTGCATCCTGCTGCAC

GCTTTCCGGATCCGGGCGGTGACGATCGACCGGGTGATGTCGTACCTGAA

CGCTTCGTAA
```

Human wild-type IL-12 p40 nucleic acid sequence
SEQ ID NO: 4

```
ATGTGTCACCAGCAGTTGGTCATCTCTTGGTTTTCCCTGGTTTTTCTGGC

ATCTCCCCTCGTGGCCATATGGGAACTGAAGAAAGATGTTTATGTCGTAG

AATTGGATTGGTATCCGGATGCCCCTGGAGAAATGGTGGTCCTCACCTGT

GACACCCCTGAAGAAGATGGTATCACCTGGACCTTGGACCAGAGCAGTGA

GGTCTTAGGCTCTGGCAAAACCCTGACCATCCAAGTCAAAGAGTTTGGAG

ATGCTGGCCAGTACACCTGTCACAAAGGAGGCGAGGTTCTAAGCCATTCG

CTCCTGCTGCTTCACAAAAAGGAAGATGGAATTTGGTCCACTGATATTTT

AAAGGACCAGAAAGAACCCAAAAATAAGACCTTTCTAAGATGCGAGGCCA

AGAATTATTCTGGACGTTTCACCTGCTGGTGGCTGACGACAATCAGTACT

GATTTGACATTCAGTGTCAAAAGCAGCAGAGGCTCTTCTGACCCCCAAGG

GGTGACGTGCGGAGCTGCTACACTCTCTGCAGAGAGAGTCAGAGGGGACA

ACAAGGAGTATGAGTACTCAGTGGAGTGCCAGGAGGACAGTGCCTGCCCA

GCTGCTGAGGAGAGTCTGCCCATTGAGGTCATGGTGGATGCCGTTCACAA

GCTCAAGTATGAAAACTACACCAGCAGCTTCTTCATCAGGGACATCATCA

AACCTGACCCACCCAAGAACTTGCAGCTGAAGCCATTAAAGAATTCTCGG

CAGGTGGAGGTCAGCTGGGAGTACCCTGACACCTGGAGTACTCCACATTC

CTACTTCTCCCTGACATTCTGCGTTCAGGTCCAGGGCAAGAGCAAGAGAG
```

-continued
AAAAGAAAGATAGAGTCTTCACGGACAAGACCTCAGCCACGGTCATCTGC
CGCAAAAATGCCAGCATTAGCGTGCGGGCCCAGGACCGCTACTATAGCTC
ATCTTGGAGCGAATGGGCATCTGTGCCCTGCAGTTAGTAA Human wild-type IL-12 p40 amino acid sequence
SEQ ID NO: 5
M C H Q Q L V I S W F S L V F L A S P L V A I W E
L K K D V Y V V E L D W Y P D A P G E M V V L T C
D T P E E D G I T W T L D Q S S E V L G S G K T L
T I Q V K E F G D A G Q Y T C H K G G E V L S H S
L L L L H K K E D G I W S T D I L K D Q K E P K N
K T F L R C E A K N Y S G R F T C W W L T T I S T
D L T F S V K S S R G S S D P Q G V T C G A A T L
S A E R V R G D N K E Y E Y S V E C Q E D S A C P
A A E E S L P I E V M V D A V H K L K Y E N Y T S
S F F I R D I I K P D P P K N L Q L K P L K N S R
Q V E V S W E Y P D T W S T P H S Y F S L T F C V
Q V Q G K S K R E K K D R V C F T D K T S A T V I
C R K N A S I S V R A Q D R Y Y S S S W S E W A S
V P C S Human improved IL-12 p40 nucleic acid sequence
SEQ ID NO: 6
ATGTGCCACCAGCAGCTGGTCATCAGCTGGTTCAGCCTCGTTTTCCTCGC
CTCGCCGCTGGTCGCCATATGGGAGCTCAAGAAGGACGTATACGTGGTGG
AGCTGGACTGGTACCCCGACGCGCCGGGCGAGATGGTCGTCCTGACGTGC
GACACGCCGGAGGAGGACGGCATCACGTGGACGCTGGACCAGTCCAGCGA
GGTCCTCGGCTCCGGCAAGACGCTGACGATCCAGGTCAAGGAGTTCGGCG
ACGCGGGCCAGTACACGTGCCACAAGGGCGGCGAGGTCCTGAGCCACTCC
CTCCTCCTGCTACACAAGAAGGAGGACGGGATCTGGAGCACGGACATCCT
CAAGGACCAGAAGGAGCCGAAGAACAAGACCTTCCTGCGCTGCGAGGCGA
AGAATTACTCGGGCCGGTTCACGTGCTGGTGGCTCACCACGATCAGCACG
GACCTGACGTTCTCGGTCAAGTCGTCGCGGGGCTCGTCGGACCCCCAGGG
GGTGACCTGCGGCGGCGACGCTGTCGGCGGAGCGGGTGCGGGGCGACA
ACAAGGAGTACGAGTACTCGGTCGAGTGCCAGGAGGACTCGGCGTGCCCG
GCGGCGGAGGAGTCGCTGCCGATCGAGGTGATGGTCGACGCGGTCCACAA
GCTGAAGTACGAGAACTACACGTCGTCGTTCTTCATCCGGGACATCATCA
AGCCGGACCCGCCGAAGAACCTGCAGCTGAAGCCGCTGAAGAACTCGCGG
CAGGTCGAGGTCTCGTGGGAGTACCCGGACACGTGGTCGACGCCGCACTC
GTACTTCTCGCTGACGTTCTGCGTCCAAGTGCAGGGCAAGTCGAAGCGGG
AGAAGAAGGACCGGGTGTTCACCGACAAGACGAGCGCGACGGTGATCTGC
CGGAAGAACGCGTCGATCTCGGTGCGGGCGCAGGACCGGTACTACTCGTC
GTCGTGGTCGGAGTGGGCGTCGGTGCCGTGCAGCTAG Rhesus wild-type IL-12 p35 nucleic acid sequence
SEQ ID NO: 7
ATGTGTCCAGCGCGCAGCCTCCTCCTTGTGGCCACCCTAGTCCTCCTGGA
CTACCTCAGTTTGGCCAGAAACCTCTCCGTGGCCACCCCAGGCCCAGAAA
TGTTCCCGTGCCTTCACCACTCCCAAAACCTGCTGAAGGCCGCCAGCAAC
ACGCTTCAGAAGGCCAGACAAATTCTAGAATTTACCCTTGCACTTCTGAA
GAGATTGATCATGAAGATATCACAAAAGATAAAACCAGCACAGTAGAGGC
CTGTTTACCATTGGAATTAATCAAGAATGAGAGTTGCCTAAATTCCAGAG
AGACTTCTTTCATAACTAATGGGAGTTGCCTGGCCTCCAGAAAGACCTCT
TTTATGATGGCCCTGTGCCTTAGGAGTATTTATGAAGACTTGAAGATGTA
CCAAGTGGAGTTCAAGACCATGAATGCAAAGCTTCTGAGGGATCCTAAGA
GGCAGATCTTTCTAGATCAAAACATACTGGGAGTTATTGATGAGCTGATG
CAGGCCCTGAATTTGAACAGTGAGACTGTGCCACAAAAATCCTCCCTTGA
AGAACCGGATTTTTATAAAACTAAAATCAAGCTCTGCATACTTCTTCATG
CTTTCAGAATTCGGGCAGTGACTATTGATAGAGTGATGAGCTATCTGAAT
GCTTCCTAATAG Rhesus wild-type IL-12 p35 amino acid sequence
SEQ ID NO: 8
M C P A R S L L L V A T L V L L D Y L S L A R N L
S V A T P G P E M F P C L H H S Q N L L K A A S N
T L Q K A R Q I L E F Y P C T S E E I D H E D I T
K D K T S T V E A C L P L E L I K N E S C L N S R
E T S F I T N G S C L A S R K T S F M M A L C L R
S I Y E D L K M Y Q V E F K T M N A K L L R D P K
R Q I F L D Q N I L G V I D E L M Q A L N F N S E
T V P Q K S S L E E P D F Y K T K I K L C I L L H
A F R I R A V T I D R V M S Y L N A S Rhesus improved IL-12 p35 nucleic acid sequence
SEQ ID NO: 9
ATGTGCCCGGCGCGCTCCCTGCTGCTCGTGGCGACGCTGGTCCTGCTCGA
CTACCTGAGCCTGGCGCGGAACCTGTCGGTGGCGACCCCGGGACCGGAGA
TGTTCCCGTGCCTGCACCACAGCCAGAACCTGCTGAAGGCGGCGTCGAAC
ACGCTGCAGAAGGCGCGGCAGATCCTGGAGTTCTACCCGTGCACGAGCGA
GGAGATCGACCACGAGGACATCACGAAGGACAAGACCAGCACGGTGGAGG
CGTGCCTGCCGCTGGAGCTGATCAAGAACGAGTCGTGCCTGAACTCGAGG
GAGACCAGCTTCATCACCAACGGCAGCTGCCTGGCCAGCAGAAAGACCTC
CTTCATGATGGCCCTGTGCCTGAGGAGCATCTACGAGGACCTGAAGATGT
ACCAGGTGGAGTTCAAGACCATGAACGCCAAGCTGCTGAGGGACCCCAAG
AGGCAGATCTTCCTGGACCAGAACATCCTGGGCGTGATCGACGAGCTGAT
GCAGGCCCTGAACTTCAACAGCGAGACCGTGCCTCAGAAGAGCAGCCTGG
AGGAGCCCGACTTCTACAAGACCAAGATCAAGCTGTGCATCCTGCTGCAC
GCCTTCCGGATCAGGGCCGTGACCATCGACAGAGTGATGAGCTACCTGAA
CGCCAGCTGATAA Rhesus wild-type IL-12 p40 nucleic acid sequence
SEQ ID NO: 10
ATGTGTCACCAGCAGCTGGTCATCTCTTGGTTTTCCCTGGTTTTTCTGGC

ATCTCCCCTCATGGCCATATGGGAACTGAAGAAAGACGTTTATGTTGTAG

AATTGGACTGGTACCCGGATGCCCCTGGAGAAATGGTGGTCCTCACCTGT

GACACCCCTGAAGAAGATGGTATCACCTGGACCTTGGACCAGAGTGGTGA

GGTCTTAGGCTCTGGCAAAACCCTGACCATCCAAGTCAAAGAGTTTGGAG

ATGCTGGCCAGTACACCTGTCACAAAGGAGGCGAGGCTCTAAGCCATTCA

CTCCTGCTGCTTCACAAAAAGGAAGATGGAATTTGGTCCACTGATGTTTT

AAAGGACCAGAAAGAACCCAAAAATAAGACCTTTCTAAGATGTGAGGCCA

AAAATTATTCTGGACGTTTCACCTGCTGGTGGCTGACGACAATCAGTACT

GATCTGACATTCAGTGTCAAAAGCAGCAGAGGCTCTTCTAACCCCCAAGG

GGTGACATGTGGAGCCGTTACACTCTCTGCAGAGAGGGTCAGAGGGGACA

ATAAGGAGTATGAGTACTCAGTGGAGTGCCAGGAGGACAGTGCCTGCCCA

GCCGCTGAGGAGAGGCTGCCCATTGAGGTCATGGTGGATGCCATTCACAA

GCTCAAGTATGAAAACTACACCAGCAGCTTCTTCATCAGGGACATCATCA

AACCCGACCCACCCAAGAACTTGCAGCTGAAGCCATTAAAGAATTCTCGG

CAGGTGGAGGTCAGCTGGGAGTACCCTGACACCTGGAGTACTCCACATTC

CTACTTCTCCCTGACATTCTGCATCCAGGTCCAGGGCAAGAGCAAGAGAG

AAAAGAAAGATAGAATCTTCACAGACAAGACCTCAGCCACGGTCATCTGC

CGCAAAAATGCCAGCTTTAGCGTGCAGGCGCAGGACCGGTACTATAGCTC

ATCTTGGAGCGAATGGGCATCTGTGCCCTGCAGTTAG

Rhesus wild-type IL-12 p40 amino acid sequence
SEQ ID NO: 11
M C H Q Q L V I S W F S L V F L A S P L M A I W E

L K K D V Y V V E L D W Y P D A P G E M V V L T C

D T P E E D G I T W T L D Q S G E V L G S G K T L

T I Q V K E F G D A G Q Y T C H K G G E A L S H S

L L L L H K K E D G I W S T D V L K D Q K E P K N

K T F L R C E A K N Y S G R F T C W W L T T I S T

D L T F S V K S S R G S S N P Q G V T C G A V T L

S A E R V R G D N K E Y E Y S V E C Q E D S A C P

A A E E R L P I E V M V D A I H K L K Y E N Y T S

S F F I R D I I K P D P P K N L Q L K P L K N S R

Q V E V S W E Y P D T W S T P H S Y F S L T F C I

Q V Q G K S K R E K K D R I F T D K T S A T V I C

R K N A S F S V Q A Q D R Y Y S S S W S E W A S V

P C S

Rhesus improved IL-12 p40 nucleic acid sequence
SEQ ID NO: 12
ATGTGCCACCAGCAGCTGGTGATCAGCTGGTTCAGCCTGGTGTTCCTGGC

CAGCCCCCTGATGGCCATCTGGGAGCTGAAGAAGGACGTATACGTGGTGG

AGCTGGACTGGTATCCCGACGCGCCTGGCGAGATGGTGGTGCTGACCTGC

GACACCCCCGAGGAGGACGGCATCACCTGGACCCTGGACCAGAGCGGCGA

AGTGCTGGGCAGCGGCAAGACCCTGACGATCCAGGTCAAGGAGTTCGGCG

ACGCCGGCCAGTACACCTGCCACAAGGGCGGCGAGGCCCTGAGCCACAGC

CTGCTGCTGCTGCACAAGAAGGAGGACGGGATCTGGAGCACCGACGTGCT

GAAGGACCAGAAGGAGCCCAAGAACAAGACCTTCCTGCGCTGCGAGGCCA

AGAATTACAGCGGCCGGTTCACCTGTTGGTGGCTGACCACCATCAGCACC

GACCTGACCTTCAGCGTGAAGAGCAGCAGAGGCAGCAGCAACCCCCAGGG

CGTGACCTGTGGCGCCGTGACCCTGAGCGCCGAGAGAGTGAGAGGCGACA

ACAAGGAGTACGAGTACAGCGTGGAGTGCCAGGAGGACAGCGCCTGCCCT

GCCGCCGAGGAGAGACTGCCCATCGAAGTGATGGTGGACGCCATCCACAA

GCTGAAGTACGAGAACTACACCAGCTCCTTCTTCATCCGGGACATCATCA

AGCCCGACCCCCCCAAGAACCTGCAGCTGAAGCCCCTGAAGAACAGCAGG

CAGGTGGAAGTGAGCTGGGAGTACCCCGACACCTGGAGCACCCCTCACAG

CTACTTCAGCCTGACCTTCTGCATCCAAGTGCAGGGCAAGAGCAAGCGGG

AGAAGAAGGACCGGATCTTCACCGATAAGACCAGCGCCACCGTGATCTGC

CGGAAGAACGCCAGCTTCAGCGTGCAGGCCGAGGACAGATACTACAGCAG

CAGCTGGAGCGAGTGGGCCAGCGTGCCTTGCAGCTGATGA

Dual promoter plasmid
SEQ ID NO: 13
CCTGGCCATTGCATACGTTGTATCCATATCATAATATGTACATTTATATT

GGCTCATGTCCAACATTACCGCCATGTTGACATTGATTATTGACTAGTTA

TTAATAGTAATCAATTACGGGGTCATTAGTTCATAGCCCATATATGGAGT

TCCGCGTTACATAACTTACGGTAAATGGCCCGCCTGGCTGACCGCCCAAC

GACCCCCGCCCATTGACGTCAATAATGACGTATGTTCCCATAGTAACGCC

AATAGGGACTTTCCATTGACGTCAATGGGTGGAGTATTTACGGTAAAGTG

CCCACTTGGCAGTACATCAAGTGTATCATATGCCAAGTACGCCCCCTATT

GACGTCAATGACGGTAAATGGCCCGCCTGGCATTATGCCCAGTACATGAC

CTTATGGGACTTTCCTACTTGGCAGTACATCTACGTATTAGTCATCGCTA

TTACCATGGTGATGCGGTTTTGGCAGTACATCAATGGGCGTGGATAGCGG

TTTGACTCACGGGGATTTCCAAGTCTCCACCCCATTGACGTCAATGGGAG

TTTGTTTTGGCACCAAAATCAACGGGACTTTCCAAAATGTCGTAACAACT

CCGCCCCATTGACGCAAATGGGCGGTAGGCGTGTACGGTGGGAGGTCTAT

ATAAGCAGAGCTCGTTTAGTGAACCGTCAGATCGCCTGGAGACGCCATCC

ACGCTGTTTTGACCTCCATAGAAGACACCGGGACCGATCCAGCCTCCGCG

GCCGCGCGTCGAGGAATTCGCTAGCGGCGCGCCAGATCTGATATCGGATC

TGCTGTGCCTTCTAGTTGCCAGCCATCTGTTGTTTGCCCCTCCCCCGTGC

CTTCCTTGACCCTGGAAGGTGCCACTCCCACTGTCCTTTCCTAATAAAAT

GAGGAAATTGCATCGCATTGTCTGAGTAGGTGTCATTCTATTCTGGGGGG

TGGGGTGGGGCAGGACAGCAAGGGGGAGGATTGGGAAGACAATAGCAGGC

ATGCTGGGGATGCGGTGGGCTCTATGGGTACCCAGGTGCTGAAGAATTGA

CCCGGTTCCTCCTGGGCCAGAAAGAAGCAGGCACATCCCCTTCTCTGTGA

-continued
```
CACACCCTGTCCACGCCCCTGGTTCTTAGTTCCAGCCCCACTCATAGGAC
ACTCATAGCTCAGGAGGGCTCCGCCTTCAATCCCACCCGCTAAAGTACTT
GGAGCGGTCTCTCCCTCCCTCATCAGCCCACCAAACCAAACCTAGCCTCC
AAGAGTGGGAAGAAATTAAAGCAAGATAGGCTATTAAGTGCAGAGGGAGA
GAAAATGCCTCCAACATGTGAGGAAGTAATGAGAGAAATCATAGAATTTC
TTCCGCTTCCTCGCTCACTGACTCGCTGCGCTCGGTCGTTCGGCTGCGGC
GAGCGGTATCAGCTCACTCAAAGGCGGTAATACGGTATCCACAGAATCAG
GGGATAACGCAGGAAAGAACATGTGAGCAAAAGGCCAGCAAAAGGCCAGG
AACCGTAAAAAGGCCGCGTTGCTGGCGTTTTTCCATAGGCTCCGCCCCCC
TGACGAGCATCACAAAAATCGACGCTCAAGTCAGAGGTGGCGAAACCCGA
CAGGACTATAAAGATACCAGGCGTTTCCCCCTGGAAGCTCCCTCGTGCGG
TCTCCTGTTCCGACCCTGCCGCTTACCGGATACCTGTCCGCCTTTCTCCC
TTCGGGAAGCGTGGCGCTTTCTCAATGCTCACGCTGTAGGTATCTCAGTT
CGGTGTAGGTCGTTCGCTCCAAGCTGGGCTGTGTGCACGAACCCCCCGTT
CAGCCCGACCGCTGCGCCTTATCCGGTAACTATCGTCTTGAGTCCAACCC
GGTAAGACACGACTTATCGCCACTGGCAGCAGCCACTGGTAACAGGATTA
GCAGAGCGAGGTATGTAGGCGGTGCTACAGAGTTCTTGAAGTGGTGGCCT
AACTACGGCTACACTAGAAGGACAGTATTTGGTATCTGCGCTCTGCTGAA
GCCAGTTACCTTCGGAAAAAGAGTTGGTAGCTCTTGATCCGGCAAACAAA
CCACCGCTGGTAGCGGTGGTTTTTTTGTTTGCAAGCAGCAGATTACGCGC
AGAAAAAAAGGATCTCAAGAAGATCCTTTGATCTTTTCTACGGGGTCTGA
CGCTCAGTGGAACGAAAACTCACGTTAAGGGATTTTGGTCATGAGATTAT
CAAAAAGGATCTTCACCTAGATCCTTTTAAATTAAAAATGAAGTTTTAAA
TCAATCTAAAGTATATATGAGTAAACTTGGTCTGACAGTTACCAATGCTT
AATCAGTGAGGCACCTATCTCAGCGATCTGTCTATTTCGTTCATCCATAG
TTGCCTGACTCGGGGGGGGGGCGCTGAGGTCTGCCTCGTGAAGAAGGT
GTTGCTGACTCATACCAGGCCTGAATCGCCCCATCATCCAGCCAGAAGT
GAGGGAGCCACGGTTGATGAGAGCTTTGTTGTAGGTGGACCAGTTGGTGA
TTTTGAACTTTTGCTTGCCACGGAACGGTCTGCGTTGTCGGGAAGATGCG
TGATCTGATCCTTCAACTCAGCAAAAGTTCGATTTATTCAACAAAGCCGC
CGTCCCGTCAAGTCAGCGTAATGCTCTGCCAGTGTTACAACCAATTAACC
AATTCTGATTAGAAAACTCATCGAGCATCAAATGAAACTGCAATTTATTC
ATATCAGGATTATCAATACCATATTTTTGAAAAAGCCGTTTCTGTAATGA
AGGAGAAAACTCACCGAGGCAGTTCCATAGGATGGCAAGATCCTGGTATC
GGTCTGCGATTCCGACTCGTCCAACATCAATACAACCTATTAATTTCCCC
TCGTCAAAAATAAGGTTATCAAGTGAGAAATCACCATGAGTGACGACTGA
ATCCGGTGAGAATGGCAAAAGCTTATGCATTTCTTTCCAGACTTGTTCAA
CAGGCCAGCCATTACGCTCGTCATCAAAATCACTCGCATCAACCAAACCG
TTATTCATTCGTGATTGCGCCTGAGCGAGACGAAATACGCGATCGCTGTT
AAAAGGACAATTACAAACAGGAATCGAATGCAACCGGCGCAGGAACACTG
```

-continued
```
CCAGCGCATCAACAATATTTTCACCTGAATCAGGATATTCTTCTAATACC
TGGAATGCTGTTTTCCCGGGGATCGCAGTGGTGAGTAACCATGCATCATC
AGGAGTACGGATAAAATGCTTGATGGTCGGAAGAGGCATAAATTCCGTCA
GCCAGTTTAGTCTGACCATCTCATCTGTAACATCATTGGCAACGCTACCT
TTGCCATGTTTCAGAAACAACTCTGGCGCATCGGGCTTCCCATACAATCG
ATAGATTGTCGCACCTGATTGCCCGACATTATCGCGAGCCCATTTATACC
CATATAAATCAGCATCCATGTTGGAATTTAATCGCGGCCTCGAGCAAGAC
GTTTCCCGTTGAATATGGCTCATAACACCCCTTGTATTACTGTTTATGTA
AGCAGACAGTTTTATTGTTCATGATGATATATTTTTATCTTGTGCAATGT
AACATCAGAGATTTTGAGACACAACGTGGATCATCCAGACATGATAAGAT
ACATTGATGAGTTTGGACAAACCACAACTAGAATGCAGTGAAAAAAATGC
TTTATTTGTGAAATTTGTGATGCTATTGCTTTATTGTAACCATTATAAGC
TGCAATAAACAAGTTAACAACAACAATTGCATTCATTTTATGTTTCAGGT
TCAGGGGGAGGTGTGGGAGGTTTTTTAAAGCAAGTAAAACCTCTACAAAT
GTGGTATGGCTGATTATGATCGTCGAGGATCTGGATCTGGATCCGGCGCG
CCTCTAGAGTTTAAACGTCGACACTGACAGATCCAAACGCTCCTCCGAC
GTCCCCAGGCAGAATGGCGGTTCCCTAAACGAGCATTGCTTATATAGACC
TCCCATTAGGCACGCCTACCGCCCATTTACGTCAATGGAACGCCCATTTG
CGTCATTGCCCCTCCCCATTGACGTCAATGGGGATGTACTTGGCAGCCAT
CGCGGGCCATTTACCGCCATTGACGTCAATGGGAGTACTGCCAATGTACC
CTGGCGTACTTCCAATAGTAATGTACTTGCCAAGTTACTATTAATAGATA
TTGATGTACTGCCAAGTGGGCCATTTTACCGTCATTGACGTCAATAGGGG
GCGTGAGAACGGATATGAATGGGCAATGAGCCATCCCATTGACGTCAATG
GTGGGTGGTCCTATTGACGTCAATGGGCATTGAGCCAGGCGGGCCATTTA
CCGTAATTGACGTCAATGGGGAGGCGCCATATACGTCAATAGGACCGCC
CATATGACGTCAATAGGAAAGACCATGAGGCCCTTTCGTCTCGCGCGTTT
CGGTGATGACGGTGAAAACCTCTGACACATGCAGCTCCCGGAGACGGTCA
CAGCTTGTCTGTAAGCGGATGCCGGGAGCAGACAAGCCCGTCAGGGCGCG
TCAGCGGGTGTTGGCGGGTGTCGGGCTGGCTTAACTATGCGGCATCAGA
GCAGATTGTACTGAGAGTGCACCATATGCGGTGTGAAATACCGCACAGAT
GCGTAAGGAGAAAATACCGCATCAGATTGGCTATTGG
```

Human IL-12 p35 signal peptide amino acid sequence
SEQ ID NO: 14
M C P A R S L L L V A T L V L L D H L S L A R Human wild-type IL-12 p35 signal peptide nucleic acid sequence
SEQ ID NO: 15
ATGTGTCCAGCGCGCAGCCTCCTCCTTGTGGCTACCCTGGTCCTCCTGGA
CCACCTCAGTTTGGCCAGA Human wild-type IL-12 p35 nucleic acid sequence without the signal peptide
SEQ ID NO: 16
AACCTCCCCGTGGCCACTCCAGACCCAGGAATGTTCCCATGCCTTCACCA
CTCCCAAAACCTGCTGAGGGCCGTCAGCAACATGCTCCAGAAGGCCAGAC -continued

AAACTCTAGAATTTTACCCTTGCACTTCTGAAGAGATTGATCATGAAGAT

ATCACAAAAGATAAAACCAGCACAGTGGAGGCCTGTTTACCATTGGAATT

AACCAAGAATGAGAGTTGCCTAAATTCCAGAGAGACCTCTTTCATAACTA

ATGGGAGTTGCCTGGCCTCCAGAAAGACCTCTTTTATGATGGCCCTGTGC

CTTAGTAGTATTTATGAAGACTTGAAGATGTACCAGGTGGAGTTCAAGAC

CATGAATGCAAAGCTTCTGATGGATCCTAAGAGGCAGATCTTTCTAGATC

AAAACATGCTGGCAGTTATTGATGAGCTGATGCAGGCCCTGAATTTCAAC

AGTGAGACTGTGCCACAAAAATCCTCCCTTGAAGAACCGGATTTTTATAA

AACTAAAATCAAGCTCTGCATACTTCTTCATGCTTTCAGAATTCGGGCAG

TGACTATTGATAGAGTGATGAGCTATCTGAATGCTTCCTAATAG

Human improved IL-12 p35 signal peptide nucleic
acid sequence
SEQ ID NO: 17
ATGTGCCCGGCGCGCTCCCTGCTGCTCGTGGCGACGCTGGTCCTGCTCGA

CCACCTGAGCCTGGCGCGG

Human improved IL-12 p35 nucleic acid sequence
without the signal peptide
SEQ ID NO: 18
AACCTGCCGGTGGCGACGCCGGACCCGGGGATGTTCCCGTGCCTGCACCA

CAGCCAGAACCTGCTGCGGGCGGTGTCGAACATGCTGCAGAAGGCGCGGC

AGACGCTGGAGTTCTACCCGTGCACGAGCGAGGAGATCGACCACGAGGAC

ATCACGAAGGACAAGACCAGCACGGTGGAGGCGTGCCTGCCGCTGGAGCT

GACGAAGAACGAGTCGTGCCTGAACTCGAGGGAGACGTCGTTCATCACGA

ACGGGTCGTGCCTGGCGTCGCGGAAGACGTCGTTCATGATGGCGCTGTGC

CTGTCGTCGATCTACGAGGACCTGAAGATGTACCAGGTGGAGTTCAAGAC

GATGAACGCGAAGCTGCTGATGGACCCGAAGCGGCAGATCTTCCTCGACC

AGAACATGCTGGCGGTGATCGACGAGCTCATGCAGGCGCTCAACTTCAAC

AGCGAGACGGTGCCGCAGAAGTCGTCGCTCGAGGAGCCGGACTTCTACAA

GACGAAGATCAAGCTCTGCATCCTGCTGCACGCTTTCCGGATCCGGGCGG

TGACGATCGACCGGGTGATGTCGTACCTGAACGCTTCGTAA

Human IL-12 p40 signal peptide amino acid sequence
SEQ ID NO: 19
M C H Q Q L V I S W F S L V F L A S P L V A Human wild-type IL-12 p40 signal peptide nucleic
acid sequence
SEQ ID NO: 20
ATGTGTCACCAGCAGTTGGTCATCTCTTGGTTTTCCCTGGTTTTTCTGGC

ATCTCCCCTCGTGGCC

Human wild-type IL-12 p40 nucleic acid sequence
without the signal peptide
SEQ ID NO: 21
ATATGGGAACTGAAGAAAGATGTTTATGTCGTAGAATTGGATTGGTATCC

GGATGCCCCTGGAGAAATGGTGGTCCTCACCTGTGACACCCCTGAAGAAG

ATGGTATCACCTGGACCTTGGACCAGAGCAGTGAGGTCTTAGGCTGTGGC

AAAACCCTGACCATCCAAGTCAAAGAGTTTGGAGATGCTGGGCAGTACAC

CTGTCACAAAGGAGGCGAGGTTCTAAGCCATTCGCTCCTGCTGCTTCACA

-continued

AAAAGGAAGATGGAATTTGGTCCACTGATATTTTAAAGGACCAGAAAGAA

CCCAAAAATAAGACCTTTCTAAGATGCGAGGCCAAGAATTATTCTGGACG

TTTCACCTGCTGGTGGCTGACGACAATCAGTACTGATTTGACATTCAGTG

TCAAAAGCAGCAGAGGCTCTTCTGACCCCCAAGGGGTGACGTGCGGAGCT

GCTAGACTCTCTGCAGAGAGAGTCAGAGGGGACAACAAGGAGTATGAGTA

CTCAGTGGAGTGCCAGGAGGACAGTGCCTGCCCAGCTGCTGAGGAGAGTC

TGCCCATTGAGGTCATGGTGGATGCCGTTCACAAGCTCAAGTATGAAAAC

TACACCAGCAGCTTCTTCATCAGGGACATCATCAAACCTGACCCACCCAA

GAACTTGCAGCTGAAGCCATTAAAGAATTCTCGGCAGGTGGAGGTCAGCT

GGGAGTACCCTGACACCTGGAGTACTCCACATTCCTACTTCTCCCTGACA

TTCTGCGTTCAGGTCCAGGGCAAGAGCAAGAGAGAAAAGAAAGATAGAGT

CTTCACGGACAAGACCTCAGCCACGGTCATCTGCCGCAAAAATGCCAGCA

TTAGCGTGCGGGCCCAGGACCGCTACTATAGCTCATCTTGGAGCGAATGG

GCATCTGTGCCCTGCAGTTAGTAA

Human improved IL-12 p40 signal peptide nucleic
acid sequence
SEQ ID NO: 22
ATGTGGCACCAGCAGGTGGTCATCAGCTGGTTCAGCCTCGTTTTCCTCGC

CTCGCCGCTGGTCGCC

Human improved IL-12 p40 nucleic acid sequence
without the signal peptide
SEQ ID NO: 23
ATATGGGAGCTCAAGAAGGACGTATACGTGGTGGAGCTGGACTGGTACCC

CGACGCGCCGGGCGAGATGGTCGTCCTGACGTGCGACACGCCGGAGGAGG

ACGGCATCACGTGGACGCTGGACCAGTCCAGCGAGGTCCTCGGGTCCGGC

AAGACGCTGACGATCCAGGTCAAGGAGTTCGGCGACGCGGGCCAGTACAC

GTGCCACAAGGGCGGCGAGGTCCTGAGCCACTCCCTCCTCCTGCTACACA

AGAAGGAGGACGGGATCTGGAGCACGGACATCCTCAAGGACCAGAAGGAG

CCGAAGAACAAGACCTTCCTGCGCTGCGAGGCGAAGAATTACTCGGGCCG

GTTCACGTGCTGGTGGCTCACCACGATCAGCACGGACCTGACGTTCTCGG

TCAAGTCGTCGCGGGGCTCGTCGGACCCCCAGGGGGTGACCTGCGGCGCG

GCGACGCTGTCGCGGAGCGGGTGCGGGCGACAACAAGGAGTACGAGTA

CTCGGTCGAGTGCCAGGAGGACTCGGCGTGCCCGGCGGCGGAGGAGTCGC

TGCCGATCGAGGTGATGGTCGACGCGGTCCACAAGCTGAAGTACGAGAAC

TACACGTCGTCGTTCTTCATCCGGGACATCATCAAGCCGGACCCGCCGAA

GAACCTGCAGCTGAAGCCGCTGAAGAACTCGCGGCAGGTCGAGGTCTCGT

GGGAGTACCCGGACACGTGGTCGACGCCGCACTCGTACTTCTCGCTGACG

TTCTGCGTCCAAGTGCAGGGCAAGTCGAAGCGGGAGAAGAAGGACCGGGT

GTTCACCGACAAGACGAGCGCGACGGTGATCTGCCGGAAGAACGCGTCGA

TCTCGGTGCGGGCGCAGGACCGGTACTACTCGTCGTCGTGGTCGGAGTGG

GCGTCGGTGCCGTGCAGCTAG

What is claimed is:

1. A nucleic acid sequence pair encoding an interleukin-12 (IL-12) protein heterodimer, the nucleic acid sequence pair comprising an IL-12p35 nucleic acid sequence and an IL-12p40 nucleic acid sequence, wherein the IL-12p35 nucleic acid sequence has at least 95% sequence identity to SEQ ID NO:3, and the IL-12p40 nucleic acid sequence has at least 95% sequence identity to SEQ ID NO:6.

2. An expression vector comprising a nucleic acid sequence pair of claim 1.

3. An isolated mammalian cell comprising a nucleic acid sequence pair of claim 1.

4. An isolated mammalian cell comprising an expression vector of claim 2.

5. A composition comprising the nucleic acid sequence pair of claim 1 and a pharmaceutically acceptable excipient.

6. A method of expressing IL-12 in a mammalian cell, the method comprising introducing a recombinant vector into a mammalian cell to express a nucleic acid sequence pair encoding an IL-12 protein heterodimer, the nucleic acid sequence pair comprising an IL-12p35 nucleic acid sequence and an IL-12p40 nucleic acid sequence, wherein the IL-12p35 nucleic acid sequence has at least 95% sequence identity to SEQ ID NO:3, and the IL-12p40 nucleic acid sequence has at least 95% sequence identity to SEQ ID NO:6.

7. A nucleic acid sequence pair encoding an interleukin-12 (IL-12) protein heterodimer, the nucleic acid sequence pair comprising an IL-12p35 nucleic acid sequence and an IL-12p40 nucleic acid sequence, wherein the IL-12p35 nucleic acid sequence has at least 80% sequence identity to SEQ ID NO:3, and the IL-12p40 nucleic acid sequence has at least 80% sequence identity to SEQ ID NO:6.

8. The nucleic acid sequence pair of claim 7, wherein expression of the IL-12 protein heterodimer from the nucleic acid sequence pair is increased by at least 2-fold in comparison to expression of the IL-12 protein heterodimer from a native mammalian IL-12 nucleic acid sequence pair.

9. The nucleic acid sequence pair of claim 7, wherein the IL-12p35 nucleic acid sequence comprises at least 55% GC content and the IL-12p40 nucleic acid sequence comprises at least 55% GC content.

10. The nucleic acid sequence pair of claim 7, wherein the IL-12p35 nucleic acid sequence has all potential splice sites removed and the IL-12p40 nucleic acid sequence has all potential splice sites removed.

11. The nucleic acid sequence pair of claim 7, wherein the nucleic acid sequence encoding the IL-12p35 has at least 80% of the non-native codons of SEQ ID NO:3 (huIL12p35opt) identified in FIG. 6, wherein the nucleic acid sequence encoding the IL-12p40 has at least 80% of the non-native codons of SEQ ID NO:6 (huIL12p40opt) identified in FIG. 8.

12. The nucleic acid sequence pair of claim 11, wherein the nucleic acid sequence encoding the IL-12p35 has non-native codons at one or more of codon numbers 2, 3, 6, 7, 8, 9, 11, 12, 15, 16, 19, 20, 21, 22, 23, 25, 26, 28, 29, 30, 32, 33, 36, 38, 41, 42, 46, 47, 48, 49, 52, 55, 56, 57, 58, 59, 60, 61, 63, 65, 66, 67, 69, 70, 71, 72, 73, 75, 76, 77, 78, 81, 84, 85, 86, 87, 88, 89, 90, 91, 93, 95, 97, 98, 99, 100, 102, 103, 105, 106, 107, 109, 112, 113, 114, 116, 117, 118, 121, 124, 125, 126, 127, 128, 129, 131, 140, 142, 143, 145, 148, 149, 151, 154, 155, 156, 157, 161, 162, 163, 164, 166, 169, 170, 171, 174, 176, 178, 179, 180, 181, 182, 183, 184, 185, 187, 188, 189, 190, 191, 192, 197, 198, 199, 200, 203, 204, 206, 208, 209, 210, 211, 214, 215, 217 and 219, wherein the codons are as identified in FIG. 6, and wherein the nucleic acid sequence encoding the IL-12p40 has non-native codons at one or more of codon numbers 2, 6, 9, 11, 12, 13, 15, 16, 17, 18, 19, 20, 21, 25, 26, 28, 29, 30, 31, 32, 33, 34, 35, 36, 38, 39, 40, 41, 42, 43, 44, 46, 48, 49, 50, 52, 53, 54, 55, 56, 57, 59, 61, 62, 65, 66, 69, 71, 73, 74, 75, 76, 78, 80, 82, 83, 84, 85, 89, 90, 92, 93, 96, 97, 99, 100, 102, 104, 106, 108, 109, 110, 111, 113, 114, 115, 116, 117, 121, 122, 123, 124, 125, 128, 129, 130, 133, 136, 137, 138, 139, 141, 145, 146, 147, 149, 150, 151, 152, 153, 155, 157, 158, 159, 160, 162, 163, 166, 169, 171, 172, 173, 174, 175, 176, 177, 179, 180, 181, 182, 187, 190, 191, 197, 198, 200, 201, 202, 205, 207, 208, 210, 212, 213, 214, 215, 218, 220, 221, 224, 225, 226, 230, 234, 235, 237, 238, 241, 245, 246, 248, 249, 252, 255, 259, 261, 263, 264, 265, 266, 267, 270, 272, 275, 276, 277, 281, 283, 284, 286, 287, 288, 289, 291, 294, 295, 296, 298, 301, 302, 303, 304, 305, 306, 307, 310, 313, 315, 316, 317, 318, 320, 321, 323, 324, 326 and 328, wherein the codons are as identified in FIG. 8.

13. An expression vector comprising a nucleic acid sequence pair of claim 7.

14. An isolated mammalian cell comprising a nucleic acid sequence pair of claim 7.

15. An isolated mammalian cell comprising an expression vector of claim 13.

16. A composition comprising the nucleic acid sequence pair of claim 7, and a pharmaceutically acceptable excipient.

17. A method of expressing IL-12 in a mammalian cell, the method comprising introducing a recombinant vector into a mammalian cell to express a nucleic acid sequence pair encoding an IL-12 protein heterodimer, the nucleic acid sequence pair comprising an IL-12p35 nucleic acid sequence and an IL-12p40 nucleic acid sequence, wherein the IL 12p35 nucleic acid sequence has at least 80% sequence identity to SEQ ID NO:3, and the IL 12p40 nucleic acid sequence has at least 80% sequence identity to SEQ ID NO:6.

18. The method of claim 17, wherein the nucleic acid sequence pair encoding the IL-12 protein heterodimer is expressed in vitro.

* * * * *

SEQUENCE LISTING

<160> NUMBER OF SEQ ID NOS: 25

<210> SEQ ID NO 1
<211> LENGTH: 663
<212> TYPE: DNA
<213> ORGANISM: Artificial Sequence
<220> FEATURE:
<223> OTHER INFORMATION: Description of Artificial Sequence:human wild-
      type interleukin-12 (IL-12) p35 nucleic acid sequence

<400> SEQUENCE: 1

```
atgtgtccag cgcgcagcct cctccttgtg gctaccctgg tcctcctgga ccacctcagt      60
ttggccagaa acctccccgt ggccactcca gacccaggaa tgttcccatg ccttcaccac     120
tcccaaaacc tgctgagggc cgtcagcaac atgctccaga aggccagaca aactctagaa     180
ttttaccctt gcacttctga agagattgat catgaagata tcacaaaaga taaaaccagc     240
acagtggagg cctgtttacc attggaatta accaagaatg agagttgcct aaattccaga     300
gagacctctt tcataactaa tgggagttgc ctggcctcca aaagaccttc ttttatgatg     360
gccctgtgcc ttagtagtat ttatgaagac ttgaagatgt accaggtgga gttcaagacc     420
atgaatgcaa agcttctgat ggatcctaag aggcagatct ttctagatca aaacatgctg     480
gcagttattg atgagctgat gcaggccctg aatttcaaca gtgagactgt gccacaaaaa     540
tcctcccttg aagaaccgga ttttttataaa actaaaatca agctctgcat acttcttcat     600
gctttcagaa ttcgggcagt gactattgat agagtgatga gctatctgaa tgcttcctaa     660
tag                                                                   663
```

<210> SEQ ID NO 2
<211> LENGTH: 219
<212> TYPE: PRT
<213> ORGANISM: Artificial Sequence
<220> FEATURE:
<223> OTHER INFORMATION: Description of Artificial Sequence:human wild-
      type interleukin-12 (IL-12) p35

<400> SEQUENCE: 2

```
Met Cys Pro Ala Arg Ser Leu Leu Leu Val Ala Thr Leu Val Leu Leu
1               5                   10                  15

Asp His Leu Ser Leu Ala Arg Asn Leu Pro Val Ala Thr Pro Asp Pro
            20                  25                  30

Gly Met Phe Pro Cys Leu His His Ser Gln Asn Leu Leu Arg Ala Val
        35                  40                  45

Ser Asn Met Leu Gln Lys Ala Arg Gln Thr Leu Glu Phe Tyr Pro Cys
    50                  55                  60

Thr Ser Glu Glu Ile Asp His Glu Asp Ile Thr Lys Asp Lys Thr Ser
65                  70                  75                  80

Thr Val Glu Ala Cys Leu Pro Leu Glu Leu Thr Lys Asn Glu Ser Cys
                85                  90                  95

Leu Asn Ser Arg Glu Thr Ser Phe Ile Thr Asn Gly Ser Cys Leu Ala
            100                 105                 110

Ser Arg Lys Thr Ser Phe Met Met Ala Leu Cys Leu Ser Ser Ile Tyr
        115                 120                 125

Glu Asp Leu Lys Met Tyr Gln Val Glu Phe Lys Thr Met Asn Ala Lys
    130                 135                 140

Leu Leu Met Asp Pro Lys Arg Gln Ile Phe Leu Asp Gln Asn Met Leu
145                 150                 155                 160
```

```
Ala Val Ile Asp Glu Leu Met Gln Ala Leu Asn Phe Asn Ser Glu Thr
            165                 170                 175

Val Pro Gln Lys Ser Ser Leu Glu Glu Pro Asp Phe Tyr Lys Thr Lys
            180                 185                 190

Ile Lys Leu Cys Ile Leu Leu His Ala Phe Arg Ile Arg Ala Val Thr
        195                 200                 205

Ile Asp Arg Val Met Ser Tyr Leu Asn Ala Ser
    210                 215

<210> SEQ ID NO 3
<211> LENGTH: 660
<212> TYPE: DNA
<213> ORGANISM: Artificial Sequence
<220> FEATURE:
<223> OTHER INFORMATION: Description of Artificial Sequence:human
      improved interleukin-12 (IL-12) p35 nucleic acid sequence

<400> SEQUENCE: 3
atgtgcccgg cgcgctccct gctgctcgtg gcgacgctgg tcctgctcga ccacctgagc    60
ctggcgcgga acctgccggt ggcgacgccg acccggggga tgttcccgtg cctgcaccac    120
agccagaacc tgctgcgggc ggtgtcgaac atgctgcaga aggcgcggca gacgctggag    180 ttctaccegt gcacgagcga ggagatcgac acgaggaca tcacgaagga caagaccagc    240
acggtggagg cgtgcctgcc gctggagctg acgaagaacg agtcgtgcct gaactcgagg    300
gagacgtcgt tcatcacgaa cgggtcgtgc ctggcgtcgc ggaagacgtc gttcatgatg    360
gcgctgtgcc tgtcgtcgat ctacgaggac ctgaagatgt accaggtgga gttcaagacg    420
atgaacgcga gctgctgat ggaccccgaag cggcagatct cctcgacca gaacatgctg    480 gcggtgatcg acgagctcat gcaggcgctc aacttcaaca gcgagacggt gccgcagaag    540
tcgtcgctcg aggagccgga cttctacaag acgaagatca gctctgcat cctgctgcac    600 gctttccgga tccgggcggt gacgatcgac cgggtgatgt cgtacctgaa cgcttcgtaa    660

<210> SEQ ID NO 4
<211> LENGTH: 990
<212> TYPE: DNA
<213> ORGANISM: Artificial Sequence
<220> FEATURE:
<223> OTHER INFORMATION: Description of Artificial Sequence:human wild-
      type interleukin-12 (IL-12) p40 nucleic acid sequence

<400> SEQUENCE: 4
atgtgtcacc agcagttggt catctcttgg ttttccctgg tttttctggc atctcccctc    60
gtggccatat gggaactgaa gaaagatgtt tatgtcgtag aattggattg gtatccggat    120
gcccctggag aaatggtggt cctcacctgt gacacccctg aagaagatgg tatcacctgg    180
accttggacc agagcagtga ggtcttaggc tctggcaaaa ccctgaccat ccaagtcaaa    240
gagtttggag atgctggcca gtacacctgt cacaaggag gcgaggttct aagccattcg    300
ctcctgctgc ttcacaaaaa ggaagatgga atttggtcca ctgatatttt aaaggaccag    360
aaagaaccca aaaataagac ctttctaaga tgcgaggcca agaattattc tggacgtttc    420
acctgctggt ggctgacgac aatcagtact gatttgacat tcagtgtcaa agcagcaga    480 ggctcttctg accccaagg ggtgacgtgc ggagctgcta cactctctgc agagagagtc    540
agaggggaca caaggagta tgagtactca gtgagtgcc aggaggacag tgcctgccca    600
gctgctgagg agagtctgcc cattgaggtc atggtggatg ccgttcacaa gctcaagtat    660
```

-continued

```
gaaaactaca ccagcagctt cttcatcagg acatcatca aacctgaccc acccaagaac    720
ttgcagctga agccattaaa gaattctcgg caggtggagg tcagctggga gtaccctgac    780
acctggagta ctccacattc ctacttctcc ctgacattct gcgttcaggt ccagggcaag    840
agcaagagag aaaagaaaga tagagtcttc acggacaaga cctcagccac ggtcatctgc    900
cgcaaaaatg ccagcattag cgtgcgggcc caggaccgct actatagctc atcttggagc    960
gaatgggcat ctgtgccctg cagttagtaa                                     990
```

<210> SEQ ID NO 5
<211> LENGTH: 328
<212> TYPE: PRT
<213> ORGANISM: Homo sapiens
<220> FEATURE:
<223> OTHER INFORMATION: human wild-type interleukin-12 (IL-12) p40

<400> SEQUENCE: 5

```
Met Cys His Gln Gln Leu Val Ile Ser Trp Phe Ser Leu Val Phe Leu
  1               5                  10                  15

Ala Ser Pro Leu Val Ala Ile Trp Glu Leu Lys Lys Asp Val Tyr Val
                 20                  25                  30

Val Glu Leu Asp Trp Tyr Pro Asp Ala Pro Gly Glu Met Val Val Leu
             35                  40                  45

Thr Cys Asp Thr Pro Glu Glu Asp Gly Ile Thr Trp Thr Leu Asp Gln
         50                  55                  60

Ser Ser Glu Val Leu Gly Ser Gly Lys Thr Leu Thr Ile Gln Val Lys
 65                  70                  75                  80

Glu Phe Gly Asp Ala Gly Gln Tyr Thr Cys His Lys Gly Gly Glu Val
                 85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300
```

```
Ser Ile Ser Val Arg Ala Gln Asp Arg Tyr Tyr Ser Ser Trp Ser
305                 310                 315                 320

Glu Trp Ala Ser Val Pro Cys Ser
                325

<210> SEQ ID NO 6
<211> LENGTH: 987
<212> TYPE: DNA
<213> ORGANISM: Artificial Sequence
<220> FEATURE:
<223> OTHER INFORMATION: Description of Artificial Sequence:human
      improved interleukin-12 (IL-12) p40 nucleic acid sequence

<400> SEQUENCE: 6
atgtgccacc agcagctggt catcagctgg ttcagcctcg ttttcctcgc ctcgccgctg        60
gtcgccatat gggagctcaa gaaggacgta tacgtggtgg agctggactg gtaccccgac       120
gcgccgggcg agatggtcgt cctgacgtgc gacacgccgg aggaggacgg catcacgtgg       180
acgctggacc agtccagcga ggtcctcggc tccggcaaga cgctgacgat ccaggtcaag       240
gagttcggcg acgcgggcca gtacacgtgc cacaagggcg cgaggtcct gagccactcc       300 ctcctcctgc tacacaagaa ggaggacggg atctggagca cggacatcct caaggaccag       360
aaggagccga gaacaagac cttcctgcgc tgcgaggcga agaattactc gggccggttc       420
acgtgctggt ggctcaccac gatcagcacg gacctgacgt tctcggtcaa gtcgtcgcgg       480
ggctcgtcgg accccaggg ggtgacctgc ggcgcggcga cgctgtcggc ggagcgggtg       540
cggggcgaca caaggagta cgagtactcg gtcgagtgcc aggaggactc ggcgtgcccg       600
gcggcggagg agtcgctgcc gatcgaggtg atggtcgacg cggtccacaa gctgaagtac       660
gagaactaca cgtcgtcgtt cttcatccgg gacatcatca gccggaccc gccgaagaac       720 ctgcagctga gccgctgaa gaactcgcgg caggtcgagg tctcgtggga gtacccggac       780
acgtggtcga cgccgcactc gtacttctcg ctgacgttct cgtccaagt gcagggcaag       840 tcgaagcggg agaagaagga ccgggtgttc accgacaaga cgagcgcgac ggtgatctgc       900
cggaagaacg cgtcgatctc ggtgcgggcg caggaccggt actactcgtc gtcgtggtcg       960
gagtgggcgt cggtgccgtg cagctag                                          987

<210> SEQ ID NO 7
<211> LENGTH: 663
<212> TYPE: DNA
<213> ORGANISM: Artificial Sequence
<220> FEATURE:
<223> OTHER INFORMATION: Description of Artificial Sequence:Macaca
      mulatta (rhesus monkey) wild-type interleukin-12 (IL-12)
      p35 nucleic acid sequence

<400> SEQUENCE: 7
atgtgtccag cgcgcagcct cctccttgtg gccaccctag tcctcctgga ctacctcagt        60
ttggccagaa acctctccgt ggccaccca ggcccagaaa tgttcccgtg ccttcaccac       120
tcccaaaacc tgctgaaggc cgccagcaac acgcttcaga aggccagaca aattctagaa       180 ttttacccttc gcacttctga agagattgat catgaagata tcacaaaaga taaaaccagc       240
acagtagagg cctgtttacc attggaatta atcaagaatg agagttgcct aaattccaga       300
gagacttctt tcataactaa tgggagttgc ctggcctcca aaagacctc ttttatgatg       360 gccctgtgcc ttaggagtat ttatgaagac ttgaagatgt accaagtgga gttcaagacc       420
atgaatgcaa agcttctgag ggatcctaag aggcagatct ttctagatca aaacatactg       480
```

-continued

```
ggagttattg atgagctgat gcaggccctg aatttcaaca gtgagactgt gccacaaaaa    540
tcctcccttg aagaaccgga tttttataaa actaaaatca agctctgcat acttcttcat    600
gctttcagaa ttcgggcagt gactattgat agagtgatga gctatctgaa tgcttcctaa    660
tag                                                                  663
```

<210> SEQ ID NO 8
<211> LENGTH: 219
<212> TYPE: PRT
<213> ORGANISM: Artificial Sequence
<220> FEATURE:
<223> OTHER INFORMATION: Description of Artificial Sequence:Macaca
      mulatta (rhesus monkey) wild-type interleukin-12 (IL-12) p35

<400> SEQUENCE: 8

```
Met Cys Pro Ala Arg Ser Leu Leu Leu Val Ala Thr Leu Val Leu Leu
 1               5                  10                  15

Asp Tyr Leu Ser Leu Ala Arg Asn Leu Ser Val Ala Thr Pro Gly Pro
            20                  25                  30

Glu Met Phe Pro Cys Leu His His Ser Gln Asn Leu Leu Lys Ala Ala
        35                  40                  45

Ser Asn Thr Leu Gln Lys Ala Arg Gln Ile Leu Glu Phe Tyr Pro Cys
    50                  55                  60

Thr Ser Glu Glu Ile Asp His Glu Asp Ile Thr Lys Asp Lys Thr Ser
65                  70                  75                  80

Thr Val Glu Ala Cys Leu Pro Leu Glu Leu Ile Lys Asn Glu Ser Cys
                85                  90                  95

Leu Asn Ser Arg Glu Thr Ser Phe Ile Thr Asn Gly Ser Cys Leu Ala
            100                 105                 110

Ser Arg Lys Thr Ser Phe Met Met Ala Leu Cys Leu Arg Ser Ile Tyr
        115                 120                 125

Glu Asp Leu Lys Met Tyr Gln Val Glu Phe Lys Thr Met Asn Ala Lys
    130                 135                 140

Leu Leu Arg Asp Pro Lys Arg Gln Ile Phe Leu Asp Gln Asn Ile Leu
145                 150                 155                 160

Gly Val Ile Asp Glu Leu Met Gln Ala Leu Asn Phe Asn Ser Glu Thr
                165                 170                 175

Val Pro Gln Lys Ser Ser Leu Glu Glu Pro Asp Phe Tyr Lys Thr Lys
            180                 185                 190

Ile Lys Leu Cys Ile Leu Leu His Ala Phe Arg Ile Arg Ala Val Thr
        195                 200                 205

Ile Asp Arg Val Met Ser Tyr Leu Asn Ala Ser
    210                 215
```

<210> SEQ ID NO 9
<211> LENGTH: 663
<212> TYPE: DNA
<213> ORGANISM: Artificial Sequence
<220> FEATURE:
<223> OTHER INFORMATION: Description of Artificial Sequence:Macaca
      mulatta (rhesus monkey) improved interleukin-12 (IL-12)
      p35 nucleic acid sequence

<400> SEQUENCE: 9

```
atgtgcccgg cgcgctccct gctgctcgtg gcgacgctgg tcctgctcga ctacctgagc     60
ctggcgcgga acctgtcggt ggcgaccccg ggaccggaga tgttcccgtg cctgcaccac    120
agccagaacc tgctgaaggc ggcgtcgaac acgctgcaga aggcgcggca gatcctggag    180
```

```
ttctacccgt gcacgagcga ggagatcgac cacgaggaca tcacgaagga caagaccagc      240
acggtggagg cgtgcctgcc gctggagctg atcaagaacg agtcgtgcct gaactcgagg      300
gagaccagct tcatcaccaa cggcagctgc ctggccagca gaaagacctc cttcatgatg      360
gccctgtgcc tgaggagcat ctacgaggac ctgaagatgt accaggtgga gttcaagacc      420
atgaacgcca agctgctgag ggaccccaag aggcagatct tcctggacca gaacatcctg      480
ggcgtgatcg acgagctgat gcaggccctg aacttcaaca cgagaccgt gcctcagaag       540 agcagcctgg aggagcccga cttctacaag accaagatca gctgtgcat cctgctgcac       600 gccttccgga tcagggccgt gaccatcgac agagtgatga gctacctgaa cgccagctga      660
taa                                                                    663
```

<210> SEQ ID NO 10
<211> LENGTH: 987
<212> TYPE: DNA
<213> ORGANISM: Artificial Sequence
<220> FEATURE:
<223> OTHER INFORMATION: Description of Artificial Sequence:Macaca
  mulatta (rhesus monkey) wild-type interleukin-12 (IL-12)
  p40 nucleic acid sequence

<400> SEQUENCE: 10

```
atgtgtcacc agcagctggt catctcttgg tttccctgg ttttctggc atctcccctc         60 atggccatat gggaactgaa gaaagacgtt tatgttgtag aattggactg gtacccggat      120
gcccctggag aaatggtggt cctcacctgt gacaccctg aagaagatgg tatcacctgg      180
accttggacc agagtggtga ggtcttaggc tctggcaaaa ccctgaccat ccaagtcaaa      240
gagtttggag atgctggcca gtacacctgt cacaaggag cgaggctct aagccattca      300 ctcctgctgc ttcacaaaaa ggaagatgga atttggtcca ctgatgtttt aaaggaccag      360
aaagaaccca aaaataagac ctttctaaga tgtgaggcca aaattattc tggacgtttc      420 acctgctggt ggctgacgac aatcagtact gatctgacat tcagtgtcaa aagcagcaga      480
ggctcttcta accccaagg ggtgacatgt ggagccgtta cactctctgc agagaggtc       540 agagggaca ataaggagta tgagtactca gtggagtgcc aggaggacag tgcctgccca      600
gccgctgagg agaggctgcc cattgaggtc atggtggatg ccattcacaa gctcaagtat      660
gaaaactaca ccagcagctt cttcatcagg gacatcatca acccgaccc acccaagaac      720 ttgcagctga agccattaaa gaattctcgg caggtggagg tcagctggga gtaccctgac     780
acctggagta ctccacattc ctacttctcc ctgacattct gcatccaggt ccagggcaag      840
agcaagagag aaaagaaaga tagaatcttc acagacaaga cctcagccac ggtcatctgc      900
cgcaaaaatg ccagctttag cgtgcaggcc caggaccgct actatagctc atcttggagc      960
gaatgggcat ctgtgccctg cagttag                                          987
```

<210> SEQ ID NO 11
<211> LENGTH: 328
<212> TYPE: PRT
<213> ORGANISM: Macaca mulatta
<220> FEATURE:
<223> OTHER INFORMATION: Macaca mulatta (rhesus monkey) wild-type
  interleukin-12 (IL-12) p40

<400> SEQUENCE: 11

```
Met Cys His Gln Gln Leu Val Ile Ser Trp Phe Ser Leu Val Phe Leu
 1               5                  10                  15

Ala Ser Pro Leu Met Ala Ile Trp Glu Leu Lys Lys Asp Val Tyr Val
```

-continued

```
                    20                  25                  30
Val Glu Leu Asp Trp Tyr Pro Asp Ala Pro Gly Glu Met Val Val Leu
            35                  40                  45

Thr Cys Asp Thr Pro Glu Glu Asp Gly Ile Thr Trp Thr Leu Asp Gln
 50                  55                  60

Ser Gly Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Ala
                85                  90                  95

Leu Ser His Ser Leu Leu Leu Leu His Lys Lys Glu Asp Gly Ile Trp
            100                 105                 110

Ser Thr Asp Val Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asn Pro Gln Gly Val Thr Cys Gly Ala Val Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Arg Leu Pro Ile
        195                 200                 205

Glu Val Met Val Asp Ala Ile His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Ile Gln Val Gln Gly Lys Ser Lys Arg Glu Lys Lys Asp Arg
        275                 280                 285

Ile Phe Thr Asp Lys Thr Ser Ala Thr Val Ile Cys Arg Lys Asn Ala
    290                 295                 300

Ser Phe Ser Val Gln Ala Gln Asp Arg Tyr Tyr Ser Ser Ser Trp Ser
305                 310                 315                 320

Glu Trp Ala Ser Val Pro Cys Ser
                325

<210> SEQ ID NO 12
<211> LENGTH: 990
<212> TYPE: DNA
<213> ORGANISM: Artificial Sequence
<220> FEATURE:
<223> OTHER INFORMATION: Description of Artificial Sequence:Macaca
      mulatta (rhesus monkey) improved interleukin-12 (IL-12)
      p40 nucleic acid sequence

<400> SEQUENCE: 12
atgtgccacc agcagctggt gatcagctgg ttcagcctgg tgttcctggc cagccccctg      60
atggccatct gggagctgaa gaaggacgta tacgtggtgg agctggactg gtatcccgac     120
gcgcctggcg agatggtggt gctgacctgc gacacccccg aggaggacgg catcacctgg     180
accctggacc agagcggcga agtgctgggc agcggcaaga ccctgacgat ccaggtcaag     240
```

```
gagttcggcg acgccggcca gtacacctgc cacaagggcg gcgaggccct gagccacagc   300
ctgctgctgc tgcacaagaa ggaggacggg atctggagca ccgacgtgct gaaggaccag   360
aaggagccca agaacaagac cttcctgcgc tgcgaggcca agaattacag cggccggttc   420
acctgttggt ggctgaccac catcagcacc gacctgacct tcagcgtgaa gagcagcaga   480
ggcagcagca accccagggg cgtgacctgt ggcgccgtga ccctgagcgc cgagagagtg   540
agaggcgaca caaggagta cgagtacagc gtggagtgcc aggaggacag cgcctgccct   600
gccgccgagg agagactgcc catcgaagtg atggtggacg ccatccacaa gctgaagtac   660
gagaactaca ccagctcctt cttcatccgg gacatcatca gcccgaccc ccccaagaac   720 ctgcagctga gcccctgaa gaacagcagg caggtggaag tgagctggga gtaccccgac   780
acctggagca cccctcacag ctacttcagc ctgaccttct gcatccaagt gcagggcaag   840
agcaagcggg agaagaagga ccggatcttc accgataaga ccagcgccac cgtgatctgc   900
cggaagaacg ccagcttcag cgtgcaggcc caggacagat actacagcag cagctggagc   960
gagtgggcca gcgtgccttg cagctgatga                                    990

<210> SEQ ID NO 13
<211> LENGTH: 4640
<212> TYPE: DNA
<213> ORGANISM: Artificial Sequence
<220> FEATURE:
<223> OTHER INFORMATION: Description of Artificial Sequence:dual
      promoter plasmid vector

<400> SEQUENCE: 13
cctggccatt gcatacgttg tatccatatc ataatatgta catttatatt ggctcatgtc    60
caacattacc gccatgttga cattgattat tgactagtta ttaatagtaa tcaattacgg   120
ggtcattagt tcatagccca tatatggagt tccgcgttac ataacttacg gtaaatggcc   180
cgcctggctg accgcccaac gacccccgcc cattgacgtc aataatgacg tatgttccca   240
tagtaacgcc aatagggact ttccattgac gtcaatgggt ggagtattta cggtaaactg   300
cccacttggc agtacatcaa gtgtatcata tgccaagtac gccccctatt gacgtcaatg   360
acggtaaatg gcccgcctgg cattatgccc agtacatgac cttatgggac tttcctactt   420
ggcagtacat ctacgtatta gtcatcgcta ttaccatggt gatgcggttt tggcagtaca   480
tcaatgggcg tggatagcgg tttgactcac ggggatttcc aagtctccac cccattgacg   540
tcaatgggag tttgttttgg caccaaaatc aacgggactt tccaaaatgt cgtaacaact   600
ccgccccatt gacgcaaatg ggcggtaggc gtgtacggtg ggaggtctat ataagcagag   660
ctcgtttagt gaaccgtcag atcgcctgga gacgccatcc acgctgtttt gacctccata   720
gaagacaccg ggaccgatcc agcctccgcg gccgcgcgtc gaggaattcg ctagcggcgc   780
gccagatctg atatcggatc tgctgtgcct tctagttgcc agccatctgt tgtttgcccc   840
tcccccgtgc cttccttgac cctggaaggt gccactccca ctgtcctttc ctaataaaat   900
gaggaaattg catcgcattg tctgagtagg tgtcattcta ttctgggggg tggggtgggg   960
caggacagca agggggagga ttgggaagac aatagcaggc atgctgggga tgcggtgggc  1020
tctatgggta cccaggtgct gaagaattga cccggttcct cctgggccag aaagaagcag  1080
gcacatcccc ttctctgtga cacaccctgt ccacgcccct ggttcttagt tccagcccca  1140
ctcataggac actcatagct caggagggct ccgccttcaa tcccacccgc taaagtactt  1200
ggagcggtct ctccctccct catcagccca ccaaaccaaa cctagcctcc aagagtggga  1260
```

```
agaaattaaa gcaagatagg ctattaagtg cagagggaga gaaaatgcct ccaacatgtg    1320
aggaagtaat gagagaaatc atagaatttc ttccgcttcc tcgctcactg actcgctgcg    1380
ctcggtcgtt cggctgcggc gagcggtatc agctcactca aaggcggtaa tacggttatc    1440
cacagaatca ggggataacg caggaaagaa catgtgagca aaaggccagc aaaaggccag    1500
gaaccgtaaa aaggccgcgt tgctggcgtt tttccatagg ctccgccccc ctgacgagca    1560
tcacaaaaat cgacgctcaa gtcagaggtg gcgaaacccg acaggactat aaagatacca    1620
ggcgtttccc cctggaagct ccctcgtgcg ctctcctgtt ccgaccctgc cgcttaccgg    1680
atacctgtcc gcctttctcc cttcgggaag cgtggcgctt tctcaatgct cacgctgtag    1740
gtatctcagt tcggtgtagg tcgttcgctc caagctgggc tgtgtgcacg aaccccccgt    1800
tcagcccgac cgctgcgcct tatccggtaa ctatcgtctt gagtccaacc cggtaagaca    1860
cgacttatcg ccactggcag cagccactgg taacaggatt agcagagcga ggtatgtagg    1920
cggtgctaca gagttcttga agtggtggcc taactacggc tacactagaa ggacagtatt    1980
tggtatctgc gctctgctga agccagttac cttcggaaaa agagttggta gctcttgatc    2040
cggcaaacaa accaccgctg gtagcggtgg tttttttgtt tgcaagcagc agattacgcg    2100
cagaaaaaaa ggatctcaag aagatccttt gatcttttct acggggtctg acgctcagtg    2160
gaacgaaaac tcacgttaag ggattttggt catgagatta tcaaaaagga tcttcaccta    2220
gatcctttta aattaaaaat gaagttttaa atcaatctaa agtatatatg agtaaacttg    2280
gtctgacagt taccaatgct taatcagtga ggcacctatc tcagcgatct gtctatttcg    2340
ttcatccata gttgcctgac tcggggggggg ggggcgctga ggtctgcctc gtgaagaagg    2400
tgttgctgac tcataccagg cctgaatcgc cccatcatcc agccagaaag tgagggagcc    2460
acggttgatg agagctttgt tgtaggtgga ccagttggtg attttgaact tttgctttgc    2520 cacgaacgg tctgcgttgt cgggaagatg cgtgatctga tccttcaact cagcaaaagt    2580
tcgatttatt caacaaagcc gccgtcccgt caagtcagcg taatgctctg ccagtgttac    2640
aaccaattaa ccaattctga ttagaaaaac tcatcgagca tcaaatgaaa ctgcaattta    2700
ttcatatcag gattatcaat accatatttt tgaaaaagcc gtttctgtaa tgaaggagaa    2760
aactcaccga gcagttcca taggatggca agatcctggt atcggtctgc gattccgact    2820
cgtccaacat caatacaacc tattaatttc ccctcgtcaa aaataaggtt atcaagtgag    2880
aaatcaccat gagtgacgac tgaatccggt gagaatggca aaagcttatg catttctttc    2940
cagacttgtt caacaggcca gccattacgc tcgtcatcaa aatcactcgc atcaaccaaa    3000
ccgttattca ttcgtgattg cgcctgagcg agacgaaata cgcgatcgct gttaaaagga    3060
caattacaaa caggaatcga atgcaaccgg cgcaggaaca ctgccagcgc atcaacaata    3120
ttttcacctg aatcaggata ttcttctaat acctggaatg ctgttttccc ggggatcgca    3180
gtggtgagta accatgcatc atcaggagta cggataaaat gcttgatggt cggaagaggc    3240
ataaattccg tcagccagtt tagtctgacc atctcatctg taacatcatt ggcaacgcta    3300
cctttgccat gtttcagaaa caactctggc gcatcgggct tcccatacaa tcgatagatt    3360
gtcgcacctg attgcccgac attatcgcga gcccatttat acccatataa atcagcatcc    3420
atgttggaat ttaatcgcgg cctcgagcaa gacgtttccc gttgaatatg gctcataaca    3480
ccccttgtat tactgtttat gtaagcagac agttttattg ttcatgatga tatattttta    3540
tcttgtgcaa tgtaacatca gagattttga gacacaacgt ggatcatcca gacatgataa    3600
gatacattga tgagtttgga caaccacaa ctagaatgca gtgaaaaaaa tgctttattt    3660
```

-continued

```
gtgaaatttg tgatgctatt gctttatttg taaccattat aagctgcaat aaacaagtta      3720
acaacaacaa ttgcattcat tttatgtttc aggttcaggg ggaggtgtgg gaggtttttt      3780
aaagcaagta aaacctctac aaatgtggta tggctgatta tgatcgtcga ggatctggat      3840
ctggatccgg cgcgcctcta gagtttaaac gtcgacactc gacagatcca aacgctcctc      3900
cgacgtcccc aggcagaatg gcggttccct aaacgagcat tgcttatata gacctcccat      3960
taggcacgcc taccgcccat ttacgtcaat ggaacgccca tttgcgtcat gcccctccc       4020 cattgacgtc aatggggatg tacttggcag ccatcgcggg ccatttaccg ccattgacgt      4080
caatgggagt actgccaatg taccctggcg tacttccaat agtaatgtac ttgccaagtt      4140
actattaata gatattgatg tactgccaag tgggccattt accgtcattg acgtcaatag      4200
ggggcgtgag aacggatatg aatgggcaat gagccatccc attgacgtca atggtgggtg      4260
gtcctattga cgtcaatggg cattgagcca ggcgggccat ttaccgtaat tgacgtcaat      4320
gggggaggcg ccatatacgt caataggacc gcccatatga cgtcaatagg aaagaccatg      4380 aggcccttc gtctcgcgcg tttcggtgat gacggtgaaa acctctgaca catgcagctc       4440
ccggagacgg tcacagcttg tctgtaagcg gatgccggga gcagacaagc ccgtcagggc      4500
gcgtcagcgg gtgttggcgg gtgtcggggc tggcttaact atgcggcatc agagcagatt      4560
gtactgagag tgcaccatat gcggtgtgaa ataccgcaca gatgcgtaag gagaaaatac      4620
cgcatcagat tggctattgg                                                 4640
```

<210> SEQ ID NO 14
<211> LENGTH: 23
<212> TYPE: PRT
<213> ORGANISM: Artificial Sequence
<220> FEATURE:
<223> OTHER INFORMATION: Description of Artificial Sequence:human
      interleukin-12 (IL-12) p35 signal peptide

<400> SEQUENCE: 14

Met Cys Pro Ala Arg Ser Leu Leu Leu Val Ala Thr Leu Val Leu Leu
1               5                   10                  15

Asp His Leu Ser Leu Ala Arg
            20

<210> SEQ ID NO 15
<211> LENGTH: 69
<212> TYPE: DNA
<213> ORGANISM: Artificial Sequence
<220> FEATURE:
<223> OTHER INFORMATION: Description of Artificial Sequence:human wild-
      type interleukin-12 (IL-12) p35 signal peptide nucleic acid
      sequence

<400> SEQUENCE: 15

```
atgtgtccag cgcgcagcct cctccttgtg gctaccctgg tcctcctgga ccacctcagt      60
ttggccaga                                                              69
```

<210> SEQ ID NO 16
<211> LENGTH: 591
<212> TYPE: DNA
<213> ORGANISM: Artificial Sequence
<220> FEATURE:
<223> OTHER INFORMATION: Description of Artificial Sequence:human wild-
      type interleukin-12 (IL-12) p35 nucleic acid sequence without the
      signal peptide

<400> SEQUENCE: 16

-continued

```
aacctccccg tggccactcc agacccagga atgttcccat gccttcacca ctcccaaaac    60
ctgctgaggg ccgtcagcaa catgctccag aaggccagac aaactctaga attttaccct   120
tgcacttctg aagagattga tcatgaagat atcacaaaag ataaaaccag cacagtggag   180
gcctgtttac cattggaatt aaccaagaat gagagttgcc taaattccag agagacctct   240
ttcataacta atgggagttg cctggcctcc agaaagacct cttttatgat ggccctgtgc   300
cttagtagta tttatgaaga cttgaagatg taccaggtgg agttcaagac catgaatgca   360
aagcttctga tggatcctaa gaggcagatc tttctagatc aaaacatgct ggcagttatt   420
gatgagctga tgcaggccct gaatttcaac agtgagactg tgccacaaaa atcctccctt   480
gaagaaccgg atttttataa aactaaaatc aagctctgca tacttcttca tgctttcaga   540
attcgggcag tgactattga tagagtgatg agctatctga atgcttccta a            591
```

<210> SEQ ID NO 17
<211> LENGTH: 69
<212> TYPE: DNA
<213> ORGANISM: Artificial Sequence
<220> FEATURE:
<223> OTHER INFORMATION: Description of Artificial Sequence:human
      improved interleukin-12 (IL-12) p35 signal peptide nucleic
      acid sequence

<400> SEQUENCE: 17

```
atgtgcccgg cgcgctccct gctgctcgtg gcgacgctgg tcctgctcga ccacctgagc    60
ctggcgcgg                                                             69
```

<210> SEQ ID NO 18
<211> LENGTH: 591
<212> TYPE: DNA
<213> ORGANISM: Artificial Sequence
<220> FEATURE:
<223> OTHER INFORMATION: Description of Artificial Sequence:human
      improved interleukin-12 (IL-12) p35 nucleic acid sequence
      without the signal peptide

<400> SEQUENCE: 18

```
aacctgccgg tggcgacgcc ggacccgggg atgttcccgt gcctgcacca cagccagaac    60
ctgctgcggg cggtgtcgaa catgctgcag aaggcgcggc agacgctgga gttctacccg   120
tgcacgagcg aggagatcga ccacgaggac atcacgaagg acaagaccag cacggtggag   180
gcgtgcctgc cgctggagct gacgaagaac gagtcgtgcc tgaactcgag ggagacgtcg   240
ttcatcacga acgggtcgtg cctggcgtcg cggaagacgt cgttcatgat ggcgctgtgc   300
ctgtcgtcga tctacgagga cctgaagatg taccaggtgg agttcaagac gatgaacgcg   360
aagctgctga tggacccgaa gcggcagatc ttcctcgacc agaacatgct ggcggtgatc   420
gacgagctca tgcaggcgct caacttcaac agcgagacgg tgccgcagaa gtcgtcgctc   480
gaggagccgg acttctacaa gacgaagatc aagctctgca tcctgctgca cgctttccgg   540
atccgggcgg tgacgatcga ccgggtgatg tcgtacctga acgcttcgta a             591
```

<210> SEQ ID NO 19
<211> LENGTH: 22
<212> TYPE: PRT
<213> ORGANISM: Artificial Sequence
<220> FEATURE:
<223> OTHER INFORMATION: Description of Artificial Sequence:human
      interleukin-12 (IL-12) p40 signal peptide

<400> SEQUENCE: 19

Met Cys His Gln Gln Leu Val Ile Ser Trp Phe Ser Leu Val Phe Leu
1               5                   10                  15

Ala Ser Pro Leu Val Ala
            20

<210> SEQ ID NO 20
<211> LENGTH: 66
<212> TYPE: DNA
<213> ORGANISM: Artificial Sequence
<220> FEATURE:
<223> OTHER INFORMATION: Description of Artificial Sequence:human wild-
      type interleukin-12 (IL-12) p40 signal peptide nucleic acid
      sequence

<400> SEQUENCE: 20
atgtgtcacc agcagttggt catctcttgg ttttccctgg ttttctggc atctcccctc    60 gtggcc                                                              66

<210> SEQ ID NO 21
<211> LENGTH: 918
<212> TYPE: DNA
<213> ORGANISM: Artificial Sequence
<220> FEATURE:
<223> OTHER INFORMATION: Description of Artificial Sequence:human wild-
      type interleukin-12 (IL-12) p40 nucleic acid sequence without the
      signal peptide

<400> SEQUENCE: 21
atatgggaac tgaagaaaga tgtttatgtc gtagaattgg attggtatcc ggatgcccct    60
ggagaaatgg tggtcctcac ctgtgacacc cctgaagaag atggtatcac ctggaccttg   120
gaccagagca gtgaggtctt aggctctggc aaaaccctga ccatccaagt caaagagttt   180
ggagatgctg gccagtacac ctgtcacaaa ggaggcgagg ttctaagcca ttcgctcctg   240
ctgcttcaca aaaaggaaga tggaatttgg tccactgata ttttaaagga ccagaaagaa   300
cccaaaaata gacctttct aagatgcgag gccaagaatt attctggacg tttcacctgc   360
tggtggctga cgacaatcag tactgatttg acattcagtg tcaaaagcag cagaggctct   420
tctgaccccc aaggggtgac gtgcggagct gctacactct ctgcagagag agtcagaggg   480
gacaacaagg agtatgagta ctcagtggag tgccaggagg acagtgcctg cccagctgct   540
gaggagagtc tgcccattga ggtcatggtg gatgccgttc acaagctcaa gtatgaaaac   600
tacaccagca gcttcttcat cagggacatc atcaaacctg acccacccaa gaacttgcag   660
ctgaagccat taagaattc tcggcaggtg gaggtcagct gggagtaccc tgacacctgg   720
agtactccac attcctactt ctccctgaca ttctgcgttc aggtccaggg caagagcaag   780
agagaaaaga agatagagt cttcacggac aagacctcag ccacggtcat ctgccgcaaa   840
aatgccagca ttagcgtgcg ggcccaggac cgctactata gctcatcttg agcgaatgg   900 gcatctgtgc cctgcagt                                                918

<210> SEQ ID NO 22
<211> LENGTH: 66
<212> TYPE: DNA
<213> ORGANISM: Artificial Sequence
<220> FEATURE:
<223> OTHER INFORMATION: Description of Artificial Sequence:human
      improved interleukin-12 (IL-12) p40 signal peptide nucleic
      acid sequence

<400> SEQUENCE: 22

```
atgtgccacc agcagctggt catcagctgg ttcagcctcg ttttcctcgc ctcgccgctg    60
gtcgcc                                                               66
```

<210> SEQ ID NO 23
<211> LENGTH: 921
<212> TYPE: DNA
<213> ORGANISM: Artificial Sequence
<220> FEATURE:
<223> OTHER INFORMATION: Description of Artificial Sequence:human
      improved interleukin-12 (IL-12) p40 nucleic acid sequence
      without the signal peptide

<400> SEQUENCE: 23

```
atatgggagc tcaagaagga cgtatacgtg gtggagctgg actggtaccc cgacgcgccg    60
ggcgagatgg tcgtcctgac gtgcgacacg ccggaggagg acggcatcac gtggacgctg   120
gaccagtcca gcgaggtcct cggctccggc aagacgctga cgatccaggt caaggagttc   180
ggcgacgcgg ccagtacac gtgccacaag ggcggcgagg tcctgagcca ctccctcctc   240
ctgctacaca agaaggagga cgggatctgg agcacggaca tcctcaagga ccagaaggag   300
ccgaagaaca agaccttcct cgcgctgcga gcgaagaatt actcgggccg gttcacgtgc   360
tggtggctca ccacgatcag cacggacctg acgttctcgg tcaagtcgtc gcggggctcg   420 tcggacccc aggggtgac ctgcggcgcg gcgacgctgt cggcggagcg ggtgcggggc   480
gacaacaagg agtacgagta ctcggtcgag tgccaggagg actcggcgtg cccggcggcg   540
gaggagtcgc tgccgatcga ggtgatggtc gacgcggtcc acaagctgaa gtacgagaac   600
tacacgtcgt cgttcttcat ccgggacatc atcaagccgg acccgccgaa gaacctgcag   660
ctgaagccgc tgaagaactc gcggcaggtc gaggtctcgt gggagtaccc ggacacgtgg   720
tcgacgccgc actcgtactt ctcgctgacg ttctgcgtcc aagtgcaggg caagtcgaag   780
cgggagaaga aggaccgggt gttcaccgac aagacgagcg cgacggtgat ctgccggaag   840
aacgcgtcga tctcggtgcg ggcgcaggac cggtactact cgtcgtcgtg gtcggagtgg   900
gcgtcggtgc cgtgcagcta g                                             921
```

<210> SEQ ID NO 24
<211> LENGTH: 4500
<212> TYPE: DNA
<213> ORGANISM: Artificial Sequence
<220> FEATURE:
<223> OTHER INFORMATION: Description of Artificial Sequence:dual
      promoter vector

<400> SEQUENCE: 24

```
cctggccatt gcatacgttg tatccatatc ataatatgta catttatatt ggctcatgtc    60
caacattacc gccatgttga cattgattat tgactagtta ttaatagtaa tcaattacgg   120
ggtcattagt tcatagccca tatatggagt tccgcgttac ataacttacg gtaaatggcc   180
cgcctggctg accgcccaac gacccccgcc cattgacgtc aataatgacg tatgttccca   240
tagtaacgcc aatagggact ttccattgac gtcaatgggt ggagtattta cggtaaactg   300
cccacttggc agtacatcaa gtgtatcata tgccaagtac gccccctatt gacgtcaatg   360
acggtaaatg gcccgcctgg cattatgccc agtacatgac cttatgggac tttcctactt   420
ggcagtacat ctacgtatta gtcatcgcta ttaccatggt gatgcggttt tggcagtaca   480
tcaatgggcg tggatagcgg tttgactcac ggggatttcc aagtctccac cccattgacg   540
tcaatgggag tttgttttgg caccaaaatc aacgggactt tccaaaatgt cgtaacaact   600
```

-continued

```
ccgcccatt gacgcaaatg ggcggtaggc gtgtacggtg ggaggtctat ataagcagag      660
ctcgtttagt gaaccgtcag atcgcctgga gacgccatcc acgctgtttt gacctccata     720
gaagacaccg ggaccgatcc agcctccgcg ggcgcgcgtc gaggaattcg ctagcggcgc     780
gccagatctg atatcggatc tgctgtgcct tctagttgcc agccatctgt tgtttgcccc    840
tcccccgtgc cttccttgac cctggaaggt gccactccca ctgtcctttc ctaataaaat    900
gaggaaattg catcgcattg tctgagtagg tgtcattcta ttctgggggg tggggtgggg    960
caggacagca aggggagga ttggaagac aatagcaggc atgctgggga tgcggtgggc    1020
tctatgggta cccaggtgct gaagaattga cccggttcct cctgggccag aaagaagcag    1080
gcacatcccc ttctctgtga cacaccctgt ccacgcccct ggttcttagt tccagcccca    1140
ctcataggac actcatagct caggagggct ccgccttcaa tcccacccgc taaagtactt    1200
ggagcggtct ctccctccct catcagccca ccaaaccaaa cctagcctcc aagagtggga    1260
agaaattaaa gcaagatagg ctattaagtg cagagggaga gaaaatgcct caacatgtg    1320 aggaagtaat gagagaaatc atagaatttc ttccgcttcc tcgctcactg actcgctgcg    1380
ctcggtcgtt cggctgcggc gagcggtatc agctcactca aaggcggtaa tacggttatc    1440
cacagaatca ggggataacg caggaaagaa catgtgagca aaaggccagc aaaaggccag    1500
gaaccgtaaa aaggccgcgt tgctggcgtt tttccatagg ctccgccccc ctgacgagca    1560
tcacaaaaat cgacgctcaa gtcagaggtg gcgaaacccg acaggactat aaagatacca    1620
ggcgtttccc cctggaagct ccctcgtgcg ctctcctgtt ccgaccctgc cgcttaccgg    1680
atacctgtcc gcctttctcc cttcgggaag cgtggcgctt tctcaatgct cacgctgtag    1740
gtatctcagt tcggtgtagg tcgttcgctc caagctgggc tgtgtgcacg aacccccgt    1800 tcagcccgac cgctgcgcct tatccggtaa ctatcgtctt gagtccaacc cggtaagaca    1860
cgacttatcg ccactggcag cagccactgg taacaggatt agcagagcga ggtatgtagg    1920
cggtgctaca gagttcttga agtggtggcc taactacggc tacactagaa ggacagtatt    1980
tggtatctgc gctctgctga agccagttac cttcggaaaa agagttggta gctcttgatc    2040
cggcaaacaa accaccgctg gtagcggtgg ttttttgtt tgcaagcagc agattacgcg    2100
cagaaaaaaa ggatctcaag aagatccttt gatcttttct acggggtctg acgctcagtg    2160
gaacgaaaac tcacgttaag ggattttggt catgagatta tcaaaaagga tcttcaccta    2220 gatccttta aattaaaaat gaagttttaa atcaatctaa agtatatatg agtaaacttg    2280
gtctgacagt taccaatgct taatcagtga ggcacctatc tcagcgatct gtctatttcg    2340
ttcatccata gttgcctgac tcgggggggg ggggcgctga gtctgcctc gtgaagaagg    2400 tgttgctgac tcataccagg cctgaatcgc cccatcatcc agccagaaag tgagggagcc    2460
acggttgatg agagctttgt tgtaggtgga ccagttggtg attttgaact tttgctttgc    2520 cacggaacg tctgcgttgt cgggaagatg cgtgatctga tccttcaact cagcaaaagt    2580
tcgatttatt caacaaagcc gccgtcccgt caagtcagcg taatgctctg ccagtgttac    2640
aaccaattaa ccaattctga ttagaaaaac tcatcgagca tcaaatgaaa ctgcaattta    2700
ttcatatcag gattatcaat accatatttt tgaaaaagcc gtttctgtaa tgaaggagaa    2760
aactcaccga ggcagttcca taggatggca agatcctggt atcggtctgc gattccgact    2820
cgtccaacat caatacaacc tattaatttc ccctcgtcaa aataaggtt atcaagtgag    2880 aaatcaccat gagtgacgac tgaatccggt gagaatggca aaagcttatg catttctttc    2940
cagacttgtt caacaggcca gccattacgc tcgtcatcaa aatcactcgc atcaaccaaa    3000
```

```
ccgttattca ttcgtgattg cgcctgagcg agacgaaata cgcgatcgct gttaaaagga    3060
caattacaaa caggaatcga atgcaaccgg cgcaggaaca ctgccagcgc atcaacaata    3120
ttttcacctg aatcaggata ttcttctaat acctggaatg ctgttttccc ggggatcgca    3180
gtggtgagta accatgcatc atcaggagta cggataaaat gcttgatggt cggaagaggc    3240
ataaattccg tcagccagtt tagtctgacc atctcatctg taacatcatt ggcaacgcta    3300
cctttgccat gtttcagaaa caactctggc gcatcgggct tcccatacaa tcgatagatt    3360
gtcgcacctg attgcccgac attatcgcga gcccatttat acccatataa atcagcatcc    3420
atgttggaat ttaatcgcgg cctcgagcaa gacgtttccc gttgaatatg gctcataaca    3480
ccccttgtat tactgtttat gtgaaaaaaa tgctttattt gtgaaatttg tgatgctatt    3540
gctttatttg taaccattat aagctgcaat aaacaagtta acaacaacaa ttgcattcat    3600
tttatgtttc aggttcaggg ggaggtgtgg gaggttttt aaagcaagta aaacctctac    3660
aaatgtggta tggctgatta tgatcgtcga ggatctggat ctggatccgg cgcgcctcta    3720
gagtttaaac gtcgacactc gacagatcca aacgctcctc cgacgtcccc aggcagaatg    3780
gcggttccct aaacgagcat tgcttatata gacctcccat taggcacgcc taccgcccat    3840
ttacgtcaat ggaacgccca tttgcgtcat tgccctcc cattgacgtc aatggggatg     3900
tacttggcag ccatcgcggg ccatttaccg ccattgacgt caatgggagt actgccaatg    3960
taccctggcg tacttccaat agtaatgtac ttgccaagtt actattaata gatattgatg    4020
tactgccaag tgggccattt accgtcattg acgtcaatag ggggcgtgag aacggatatg    4080
aatgggcaat gagccatccc attgacgtca atggtgggtg gtcctattga cgtcaatggg    4140
cattgagcca ggcgggccat ttaccgtaat tgacgtcaat ggggaggcg ccatatacgt     4200 caataggacc gcccatatga cgtcaatagg aaagaccatg aggccctttc gtctcgcgcg    4260
tttcggtgat gacggtgaaa acctctgaca catgcagctc ccgagacgg tcacagcttg     4320 tctgtaagcg gatgccggga gcagacaagc ccgtcagggc gcgtcagcgg tgttggcgg    4380 gtgtcggggc tggcttaact atgcggcatc agagcagatt gtactgagag tgcaccatat    4440
gcggtgtgaa ataccgcaca gatgcgtaag gagaaaatac cgcatcagat tggctattgg    4500
```

<210> SEQ ID NO 25
<211> LENGTH: 271
<212> TYPE: PRT
<213> ORGANISM: Artificial Sequence
<220> FEATURE:
<223> OTHER INFORMATION: Description of Artificial Sequence:kanamycin
      marker of dual promoter vector

<400> SEQUENCE: 25

```
Met Ser His Ile Gln Arg Glu Thr Ser Cys Ser Arg Pro Arg Leu Asn
  1               5                  10                  15

Ser Asn Met Asp Ala Asp Leu Tyr Gly Tyr Lys Trp Ala Arg Asp Asn
             20                  25                  30

Val Gly Gln Ser Gly Ala Thr Ile Tyr Arg Leu Tyr Gly Lys Pro Asp
         35                  40                  45

Ala Pro Glu Leu Phe Leu Lys His Gly Lys Gly Ser Val Ala Asn Asp
     50                  55                  60

Val Thr Asp Glu Met Val Arg Leu Asn Trp Leu Thr Glu Phe Met Pro
 65                  70                  75                  80

Leu Pro Thr Ile Lys His Phe Ile Arg Thr Pro Asp Asp Ala Trp Leu
                 85                  90                  95
```

-continued

```
Leu Thr Thr Ala Ile Pro Gly Lys Thr Ala Phe Gln Val Leu Glu Glu
            100                 105                 110

Tyr Pro Asp Ser Gly Glu Asn Ile Val Asp Ala Leu Ala Val Phe Leu
        115                 120                 125

Arg Arg Leu His Ser Ile Pro Val Cys Asn Cys Pro Phe Asn Ser Asp
    130                 135                 140

Arg Val Phe Arg Leu Ala Gln Ala Gln Ser Arg Met Asn Asn Gly Leu
145                 150                 155                 160

Val Asp Ala Ser Asp Phe Asp Glu Arg Asn Gly Trp Pro Val Glu
                165                 170                 175

Gln Val Trp Lys Glu Met His Lys Leu Leu Pro Phe Ser Pro Asp Ser
                180                 185                 190

Val Val Thr His Gly Asp Phe Ser Leu Asp Asn Leu Ile Phe Asp Glu
            195                 200                 205

Gly Lys Leu Ile Gly Cys Ile Asp Val Gly Arg Val Gly Ile Ala Asp
        210                 215                 220

Arg Tyr Gln Asp Leu Ala Ile Leu Trp Asn Cys Leu Gly Glu Phe Ser
225                 230                 235                 240

Pro Ser Leu Gln Lys Arg Leu Phe Gln Lys Tyr Gly Ile Asp Asn Pro
                245                 250                 255

Asp Met Asn Lys Leu Gln Phe His Leu Met Leu Asp Glu Phe Phe
                260                 265                 270
```